(12) United States Patent
Marquiss et al.

(10) Patent No.: US 6,902,703 B2
(45) Date of Patent: Jun. 7, 2005

(54) INTEGRATED SAMPLE-PROCESSING SYSTEM

(75) Inventors: Samuel A. Marquiss, Santa Clara, CA (US); Christopher G. Cesar, Sunnyvale, CA (US); Jon F. Petersen, Redwood City, CA (US); David P. Stumbo, Belmont, CA (US); Amer El-Hage, Menlo Park, CA (US); Glenn R. Edwards, Palo Alto, CA (US); Douglas N. Modlin, Palo Alto, CA (US); Lev J. Leytes, Palo Alto, CA (US); Samuel Burd, Oakland, CA (US)

(73) Assignee: LJL Biosystems, Inc., Sunnyvale, CA (US)

( * ) Notice: Subject to any disclaimer, the term of this patent is extended or adjusted under 35 U.S.C. 154(b) by 353 days.

(21) Appl. No.: 09/777,343

(22) Filed: Feb. 5, 2001

(65) Prior Publication Data

US 2001/0048899 A1 Dec. 6, 2001

Related U.S. Application Data

(63) Continuation of application No. PCT/US00/12277, filed on May 3, 2000.
(60) Provisional application No. 60/132,262, filed on May 3, 1999, provisional application No. 60/132,263, filed on May 3, 1999, provisional application No. 60/138,737, filed on Jun. 11, 1999, provisional application No. 60/138,893, filed on Jun. 11, 1999, provisional application No. 60/153,251, filed on Sep. 10, 1999, and provisional application No. 60/167,301, filed on Nov. 24, 1999.

(51) Int. Cl.[7] .................................................. B01L 3/02
(52) U.S. Cl. ........................... 422/100; 422/99; 436/54; 436/174; 436/180; 73/863; 73/863.31; 73/863.32
(58) Field of Search ....................... 422/62–66, 99–104; 436/43–47, 49, 54, 174, 180; 73/863, 863.31, 863.32, 864, 864.21

(56) References Cited

U.S. PATENT DOCUMENTS

| | | | |
|---|---|---|---|
| 4,877,745 A | 10/1989 | Hayes et al. | |
| 5,443,791 A | 8/1995 | Cathcart et al. | 422/65 |
| 5,660,792 A | 8/1997 | Koike | 422/63 |
| 5,756,304 A | 5/1998 | Jovanovich | 435/34 |
| 5,760,900 A | 6/1998 | Ito et al. | |
| 5,800,778 A | 9/1998 | Chen et al. | 422/48 |
| 5,853,894 A | 12/1998 | Brown | 428/422 |
| 5,872,010 A * | 2/1999 | Karger et al. | 436/173 |
| 5,873,394 A | 2/1999 | Meltzer | 141/130 |
| 5,897,304 A * | 4/1999 | Kaneko | 417/552 |
| 5,961,926 A | 10/1999 | Kolb et al. | 422/101 |
| 6,045,755 A | 4/2000 | Lebl et al. | 422/65 |
| 6,102,885 A * | 8/2000 | Bass | 604/22 |
| 6,113,559 A * | 9/2000 | Klopotek | 601/3 |
| 6,121,048 A * | 9/2000 | Zaffaroni et al. | 436/45 |
| 6,203,759 B1 * | 3/2001 | Pelc et al. | 422/100 |
| 6,207,031 B1 * | 3/2001 | Adourian et al. | 204/451 |
| 6,220,075 B1 * | 4/2001 | Papen et al. | 73/1.74 |

FOREIGN PATENT DOCUMENTS

| | | |
|---|---|---|
| EP | 0810438 | 12/1997 |
| WO | WO 97/44134 | 11/1997 |

* cited by examiner

*Primary Examiner*—Jill Warden
*Assistant Examiner*—Dwayne K Handy
(74) *Attorney, Agent, or Firm*—Kolisch Hartwell, P.C.

(57) ABSTRACT

The invention provides an integrated sample-processing system and components thereof for preparing and/or analyzing samples. The components may include a transport module, a fluidics module, and an analysis module, among others.

28 Claims, 32 Drawing Sheets

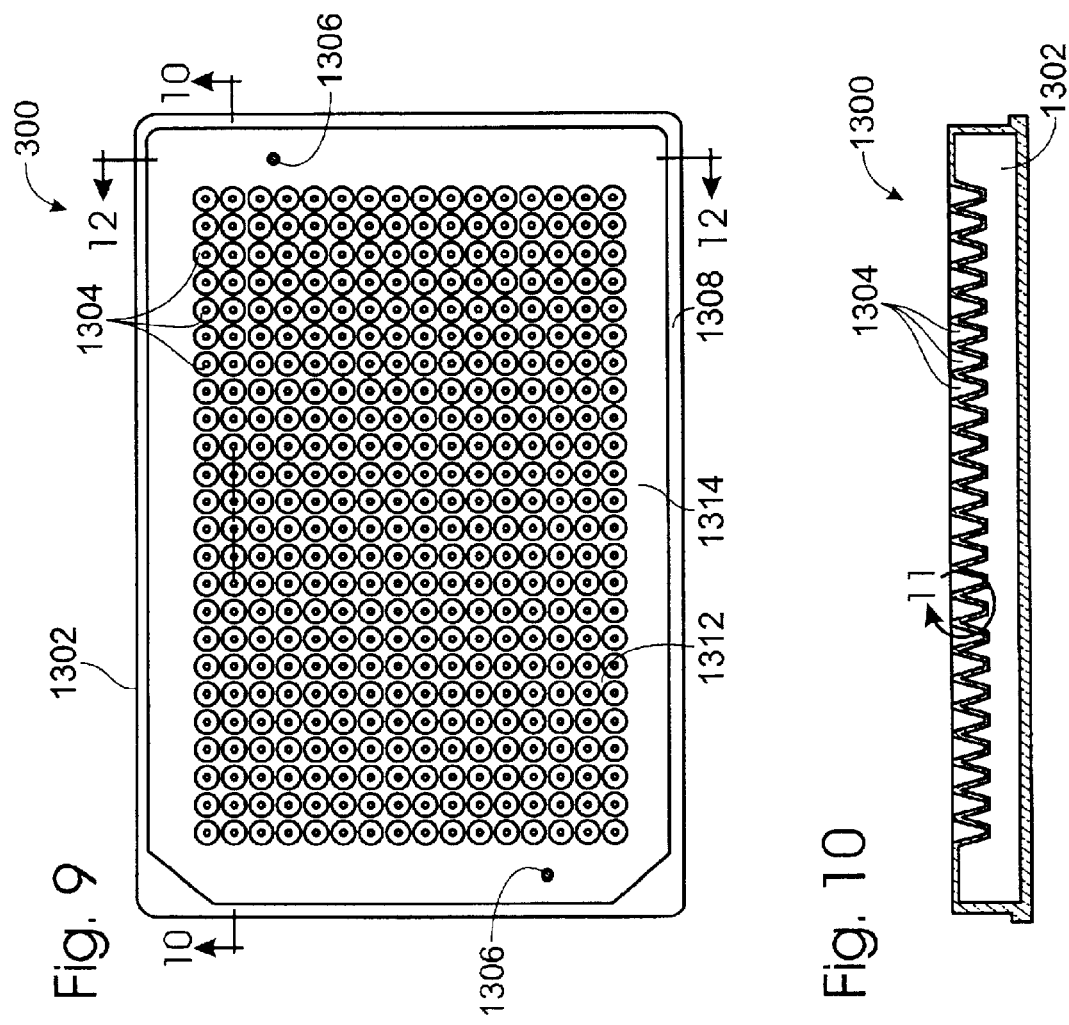

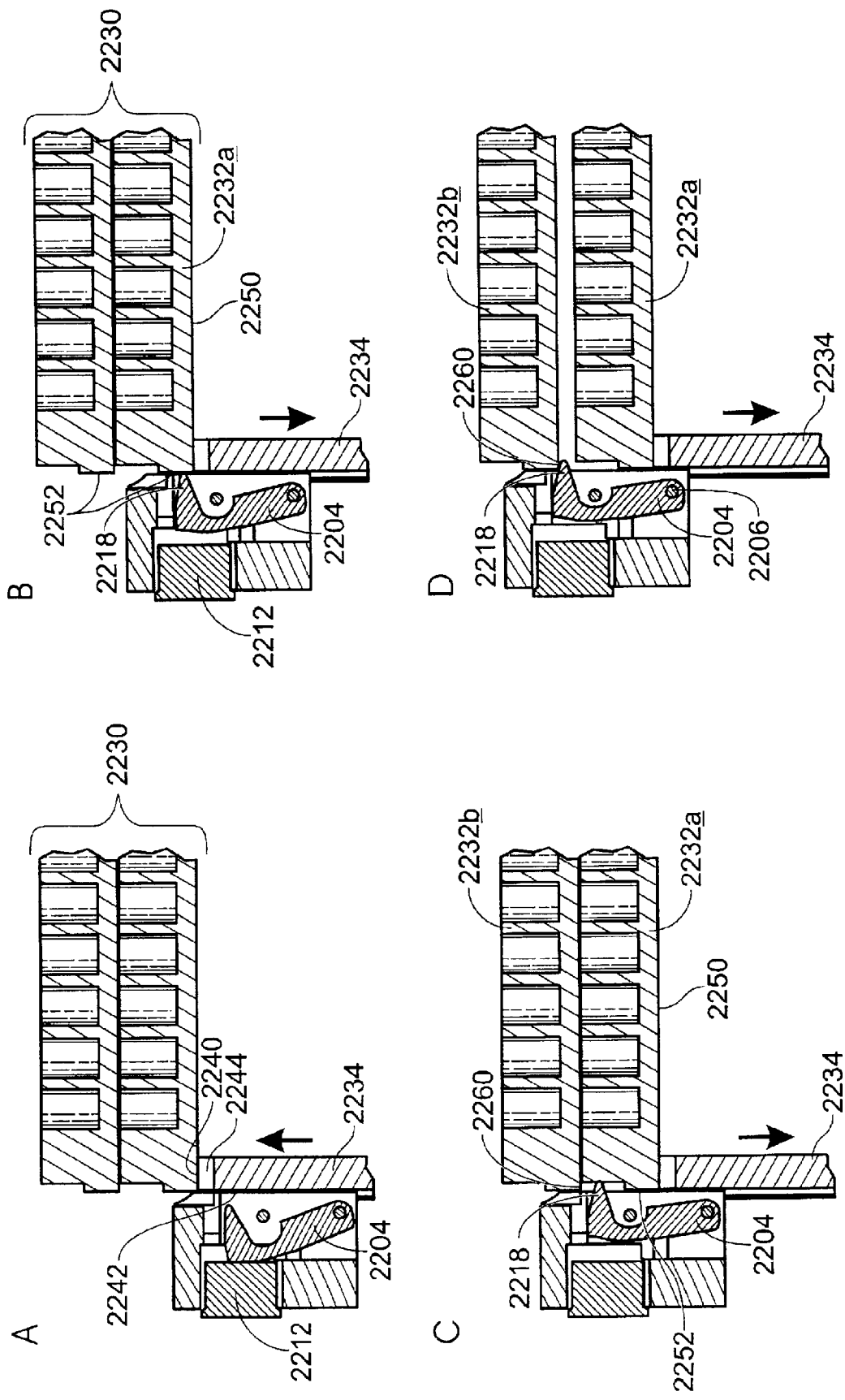

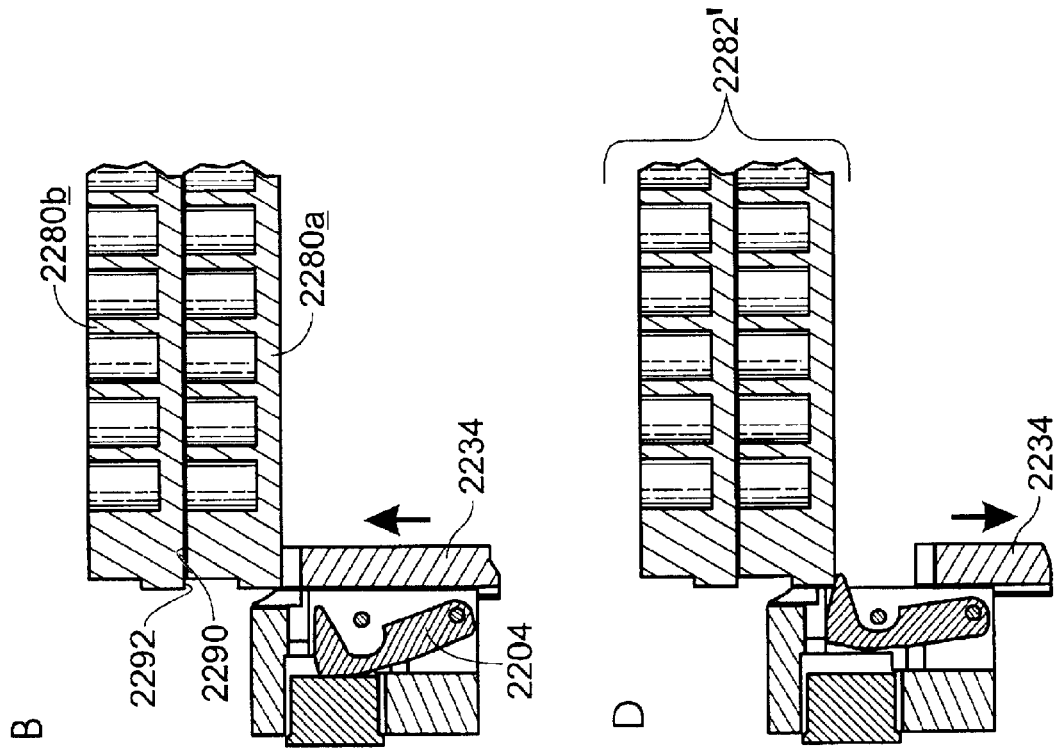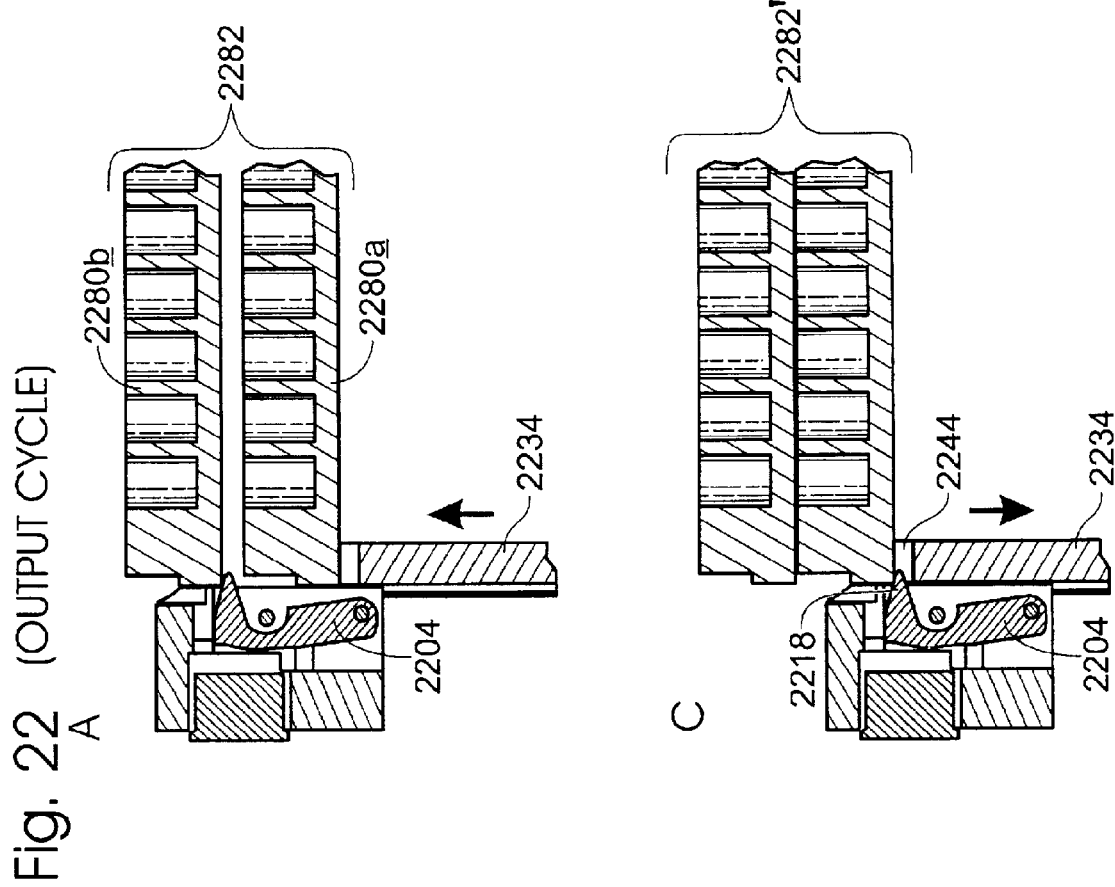
Fig. 22 (OUTPUT CYCLE)

INTEGRATED SAMPLE-PROCESSING SYSTEM

CROSS-REFERENCES

This application is a continuation of PCT Patent Application Ser. No. PCT/US00/12277, filed May 3, 2000, which is incorporated herein by reference.

This application is based upon and claims priority under 35 U.S.C. §119 from the following U.S. Provisional Patent Applications, each of which is incorporated herein by reference: Ser. No. 60/132,262, filed May 3, 1999; Ser. No. 60/132,263, filed May 3, 1999; Ser. No. 60/138,737, filed Jun. 11, 1999; Ser. No. 60/138,893, filed Jun. 11, 1999; Ser. No. 60/153,251, filed Sep. 10, 1999; and Ser. No. 60/167,301, filed Nov. 24, 1999.

This application incorporates by reference the following U.S. patent applications: Ser. No. 08/929,095, filed Sep. 15, 1997, Ser. No. 09/062,472, filed Apr. 17, 1998; Ser. No. 09/160,533, filed Sep. 24, 1998; Ser. No. 09/349,733, filed Jul. 8, 1999; Ser. No. 09/468,440, filed Dec. 21, 1999; Ser. No. 09/478,819, filed Jan. 5, 2000; Ser. No. 09/494,407, filed Jan. 28, 2000; and Ser. No. 09/556,030, filed Apr. 20, 2000.

This application also incorporates by reference the following PCT patent applications: Ser. No PCT/US99/01656, filed Jan. 25, 1999; Ser. No. PCT/US99/03678, filed Feb. 19, 1999; Ser. No. PCT/US99/08410, filed Apr. 16, 1999; Ser. No. PCT/US99/16057, filed Jul. 15, 1999; Ser. No. PCT/US99/16453, filed Jul. 21, 1999; Ser. No. PCT/US99/16621, filed Jul. 23, 1999; Ser. No. PCT/US99/16286, filed Jul. 26, 1999; Ser. No. PCT/US99/16287, filed Jul. 26, 1999; Ser. No. PCT/US99/24707, filed Oct. 19, 1999; Ser. No. PCT/US00/00895, filed Jan. 14, 2000; Ser. No. PCT/US00/03589, filed Feb. 11, 2000; Ser. No. PCT/US00/04543, filed Feb. 22, 2000, and Ser. No. PCT/US00/06841, filed Mar. 15, 2000.

This application also incorporates by reference the following U.S. provisional patent applications: Ser. No. 60/138,311, filed Jun. 9, 1999; Ser. No. 60/138,438, filed Jun. 10, 1999; Ser. No. 60/142,721, filed Jul. 7, 1999; Ser. No. 60/164,633, filed Nov. 10, 1999; 60/165,813, filed Nov. 16, 1999; Ser. No. 60/167,463, filed Nov. 24; 1999; Ser. No. 60/178,026, filed Jan. 26, 2000; Ser. No. 60/182,036, filed Feb. 11, 2000; Ser. No. 60/182,419, filed Feb. 14, 2000; Ser. No. 60/190,265, filed Mar. 17, 2000; Ser. No. 60/191,890, filed Mar. 23, 2000; Ser. No. 60/193,586, filed Mar. 30, 2000; Ser. No. 60/197,324, filed Apr. 14, 2000; Ser. No. 60/200,530, filed Apr. 27, 2000, and Ser. No. 60/200,594, filed Apr. 28, 2000.

This application also incorporates by reference the following publications: K. E. van Holde, *Physical Biochemistry* ($2^{nd}$ ed. 1985); William Bains, *Biotechnology from A to Z* (1993); Richard P. Haugland, *Handbook of Fluorescent Probes and Research Chemicals* ($6^{th}$ ed. 1996); Joseph R. Lakowicz, *Principles of Fluorescence Spectroscopy* ($2^{nd}$ ed. 1999). Bob Sinclair, *Everything's Great When It Sits on a Chip: A Bright Future for DNA Arrays*, 13 THE SCIENTIST, May 24, 1999, at 18; and Charles R. Cantor and Paul R. Schimmel, *Biophysical Chemistry* (1980).

FIELD OF THE INVENTION

The invention relates to sample-processing systems, and more particularly to integrated sample-processing systems and components thereof for preparing and/or analyzing samples.

BACKGROUND

Modern laboratory techniques such as high-throughput screening of candidate drug compounds may involve preparing and analyzing hundreds of thousands or millions of samples. Recently, the processing of such samples has been facilitated by packaging samples in high-density sample holders, such as microplates, for analysis together in an automated device. FIG. 1 shows an offset stack of microplates, illustrating the range in possible well densities and well dimensions. Plate 130 has 96 sample wells. Plate 132 has 384 wells. Plate 134 has 1536 wells. Plate 136 has 3456 wells. Plate 138 has 9600 wells.

Unfortunately, prior systems for processing large numbers of samples have significant shortcomings. For example, prior systems may not have the flexibility to process sample holders with different sample densities, or the sensitivity or accuracy to process sample holders with very small samples. Moreover, prior systems may be limited to single (unit) operations, meaning, for example, that they can dispense samples or analyze samples, but not do both. Thus, prior systems may require different apparatus for different applications, or lead to missed hits, limited research capabilities, lower throughput, and/or increased costs for compounds, assays, and reagents.

SUMMARY OF THE INVENTION

The invention provides an integrated sample-processing system and components thereof for preparing and/or analyzing samples. The components may include a transport module, a fluidics module, and an analysis module, among others.

BRIEF DESCRIPTION OF THE DRAWINGS

FIG. 9 is a top view of a 384-well microplate constructed in accordance with the invention.

FIG. 10 is a cross-sectional view of the microplate in FIG. 8, taken generally along line 10—10 in FIG. 9.

FIG. 11 is an enlarged portion of the cross-sectional view in FIG. 10, showing details of a sample well.

FIG. 12 is an enlarged cross-sectional view of the microplate in FIG. 9, taken generally along line 12—12 in FIG. 9, showing details of a reference fiducial.

FIG. 21 is a multi-panel time-lapse cross-sectional view of the latch mechanism of FIG. 20, showing the latch mechanism in use to input a plate from a stack of plates.

FIG. 22 is a multi-panel time-lapse cross-sectional view of the latch mechanism of FIG. 20, showing the latch mechanism in use to output a plate to a stack of plates.

DETAILED DESCRIPTION OF THE INVENTION

Figure 1:
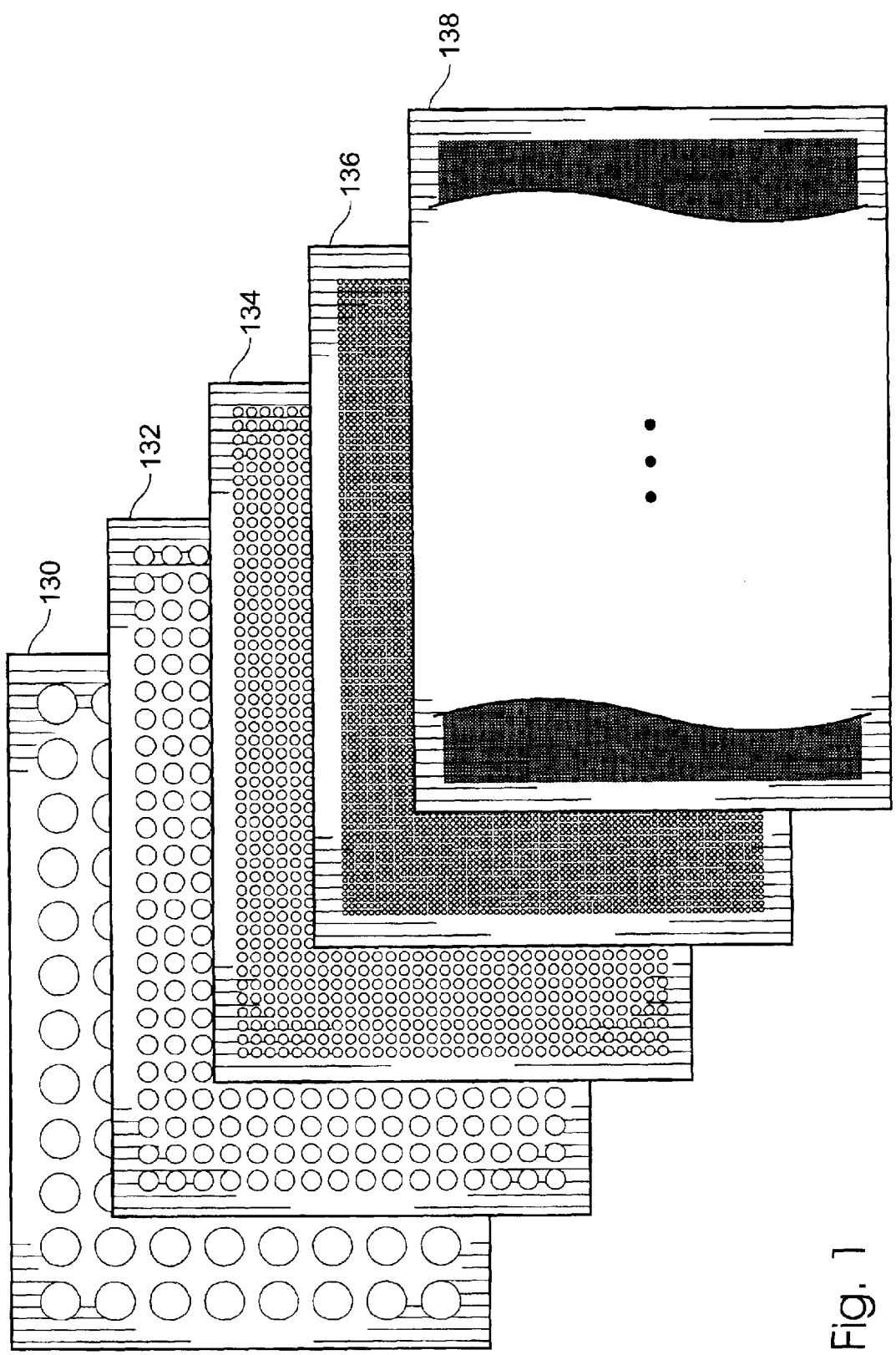
FIG. 1 is a top view of overlapping microplates showing variations in well size and well density.
Figure 2:
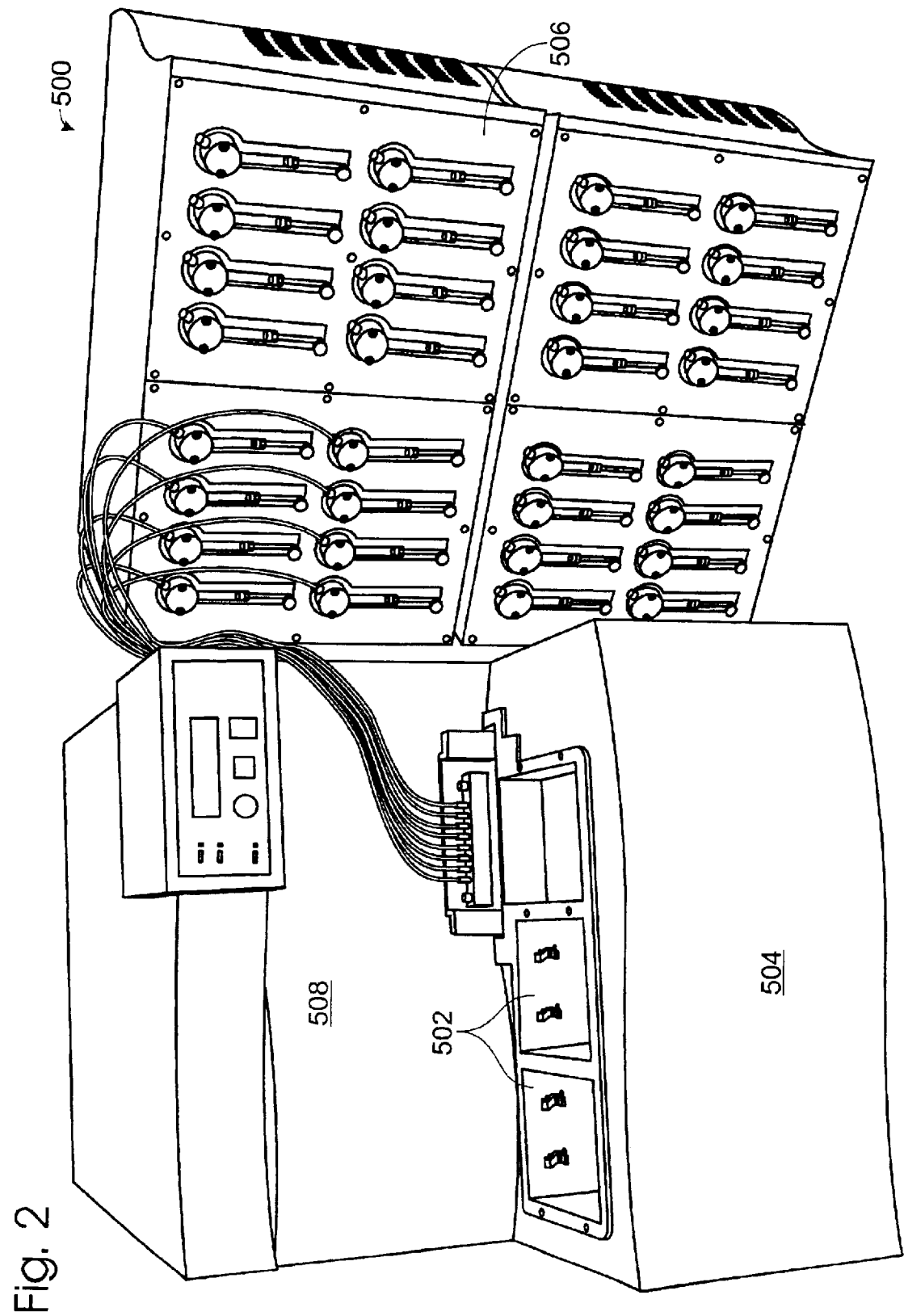
FIG. 2 is a perspective view of a system for preparing and/or analyzing samples.

FIG. 2 is a perspective view of a system 500 for preparing and/or analyzing samples. System 500 includes at least one input/output (I/O) site 502 for sample input and output, and a plurality of function modules (or stations) for performing a plurality of functions, including a transport module 504, a fluidics module 506, and an analysis module 508. The transport module participates in sample transport, for example, by shuttling a sample or sample holder between the I/O sites, fluidics module, and analysis module. The fluidics module participates in sample preparation, for example, by adding (and/or removing) a component of a sample to a sample holder. The analysis module participates in sample analysis, for example, by performing an optical analysis of a sample based on photoluminescence, chemiluminescence, absorbance, and scattering, among others. The components of system 500 may be configured to enhance function, convenience, and/or appearance.

Figure 3:
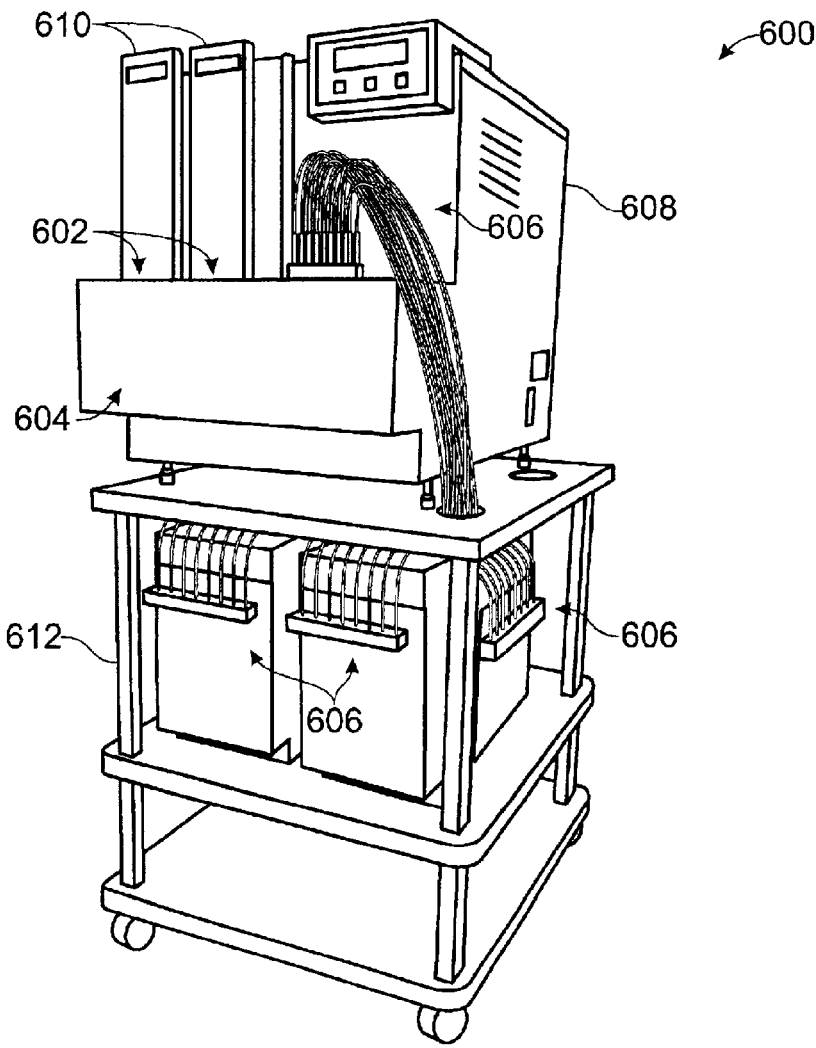
FIG. 3 is a perspective view of an alternative system for preparing and/or analyzing samples.

FIG. 3 is a perspective view of an alternative system 600 for preparing and/or analyzing samples. System 600 resembles system 500 and similarly includes at least one I/O site 602, a transport module 604, a fluidics module 606, and an analysis module 608. However, in system 600, the I/O sites include processing bins 610 to facilitate handling multiple sample holders. Moreover, the fluidics module and the transport and analysis modules are positioned on different shelves of a moveable multi-tiered cart 612, enhancing portability and reducing footprint (<1 square meter).

Figure 4:
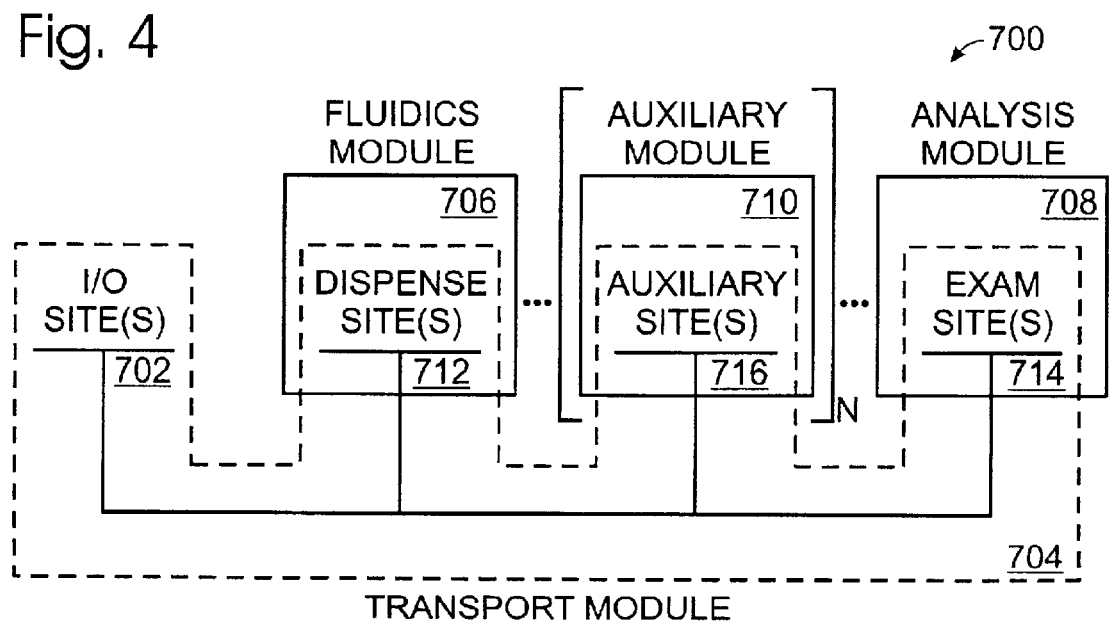
FIG. 4 is a schematic view of a generalized system for preparing and/or analyzing samples.

FIG. 4 is a schematic view of a generalized system 700 for preparing and/or analyzing samples. System 700 includes at least one I/O site 702 and a plurality of function modules, including a transport module 704, a fluidics module 706, and an analysis module 708, as above, as well as N auxiliary modules 710 associated with redundant and/or additional functionalities, such as cleaning, sealing, storage, sample preparation, etc. Here, N may range from zero to several or more. A cleaning module might include components for emptying and/or cleaning sample holders. A sealing module might include components for sealing, unsealing, and/or otherwise covering and uncovering sample holders. An incubation module might include components for incubating sample holders and their associated samples, with environmental control of atmosphere, temperature, agitation, and so on. A sample preparation module might include components for particular sample-preparation functions, such as a thermocycler for performing heating and cooling during the polymerase chain reaction (PCR).

Function modules generally include one or more function sites at which a corresponding function is performed. For example, a fluidics module may include a dispense site 712 at which a fluid is dispensed, an analysis module may include an examination ("exam") site 714 at which a sample is analyzed, and an auxiliary module may include an auxiliary site 716 at which an auxiliary function is performed, such as cleaning, sealing, storage, etc. A transport module may be connected directly or indirectly with I/O sites 702 for sample input and output, and with one or more of the function sites. If the transport module is connected indirectly to a function (or I/O) site, the transport module might hand off a sample holder at a transfer site to a separate transport mechanism associated with the respective function module. A transport module also may be connected to additional robotics for providing and removing sample holders from the I/O sites.

System 700 generally may include any desired combination of function modules. For example, a simple system may include a pair of modules, such as a fluidics module and a transport module, or an analysis module and a transport module. These systems might be used to prepare a sample or analyze a sample, respectively. A more complex system may include several modules, such as a fluidics module, an analysis module, an incubation module, and a transport module. This more complex system might be used to prepare a sample, analyze a sample, or both prepare and analyze a sample, for example, by adding a reporter to the sample using the fluidics module, incubating the sample using the incubation module, reading the sample using the analysis module, and inputting, outputting, and transporting the sample using the transport module.

The function modules generally may be accessed in any desired order. For example, a sample might be analyzed only after fluid dispensing, or both before and after fluid dispensing if a multi-step assay is being performed and/or if a background is being subtracted. The order of access may be controlled using a controller that may schedule and initiate singulation of samples to and from I/O sites, transport between sites, dispensing at a dispensing site, and/or analysis at an analysis site. The order and timing of such movements will depend on the nature of the assay and generally will differ for kinetics assays (where timing is crucial) and endpoint assays (where timing is not crucial, so long as an endpoint has been reached).

The function modules generally may be combined or integrated in any desired way. For example, a single module may perform fluidics and cleaning operations, and a single transport mechanism may access any or all of the I/O and/or function sites.

Further aspects of the invention are presented in the following sections: (A) sample holders, (B) transport module, (C) fluidics module, (D) auxiliary modules, (E) analysis module; and (F) additional examples.

A. Sample Holders

The system and its components may be used with a variety of sample holders and sample holder features. As used here, "sample holder" generally comprises any substrate or material capable of supporting a sample so that the sample holder and associated sample can be transported by an automatic transport module and subjected to a function such as fluid dispensing or optical analysis at a corresponding function module. Sample holders may be used alone, in stacks, or in combination with seals or covers, as described below. Sample holders may support samples at low, intermediate, or high density, and be designed for single or multiple use.

Exemplary sample holders include microplates, PCR plates, biochips, and chromatography plates, among others. A microplate is a multi-well sample holder, typically but not exclusively used for luminescence applications. Preferred microplates are described below. A PCR plate is a multi-well sample holder used for performing PCR. Preferred PCR plates would include a footprint, well spacing, and well shape similar to those of the preferred microplates, while possessing a stiffness adequate for automated handling and a thermal stability adequate for PCR. A biochip is a small, flat surface (such as a glass or silicon wafer) onto which biomolecules (such as nucleic acids and proteins) are immobilized in distinct spots or arrays. Biochips include DNA chips, DNA microarrays, gene arrays, and gene chips, among others. Preferred biochips are described in Bob Sinclair, *Everything's Great When It Sits on a Chip: A Bright Future for DNA Arrays,* 13 THE SCIENTIST, May 24, 1999, at 18. A chromatography plate is a flat surface used for performing chromatography, such as thin-layer chromatography.

Microplates are a preferred sample holder, and the system and its components may be designed for use with microplates having some or all of the following features. For example, suitable microplates may include microplates having any number of wells, including 96, 384, and 1536, among others. Suitable microplates also may include microplates having wells with elevated bottoms, frusto-conical shapes, and/or low volumes, or wells configured to reduce the formation and/or trapping of bubbles, as described in the following U.S. patent applications, which are incorporated herein by reference: Ser. No. 08/840,553, filed Apr. 14, 1997; and Ser. No. 09/478,819, filed Jan. 5, 2000. Suitable microplates also may include microplates having reference fiducials in or around a perimeter portion of the microplate (or elsewhere), as described in PCT Patent Application Ser. No. PCT/US99/08410, filed Apr. 16, 1999, which is incorporated herein by reference. Such reference fiducials may be molded into the plate and/or applied to the plate by silkscreen, color transfer, hot stamping, and/or application of reflective paint, among others. Suitable microplates also may include microplates having a barcode for reading by a barcode reader, as described in U.S. patent application Ser. No. 09/160,533, filed Sep. 24, 1998, which is incorporated herein by reference. Suitable microplates also may be useable in combination with seals for sealing individual wells in a microplate, and/or spacer members for separating individual microplates in a stack, as described below.

FIGS. 5–17 show a set of preferred microplates that have similar heights and footprints but that differ in well shape, well size, and/or well density. These microplates include (1) 96-well microplates, (2) 384-well microplates, (3) 1536-well microplates, and (4) miscellaneous microplates.

1. 96-Well Microplates

Figure 5:
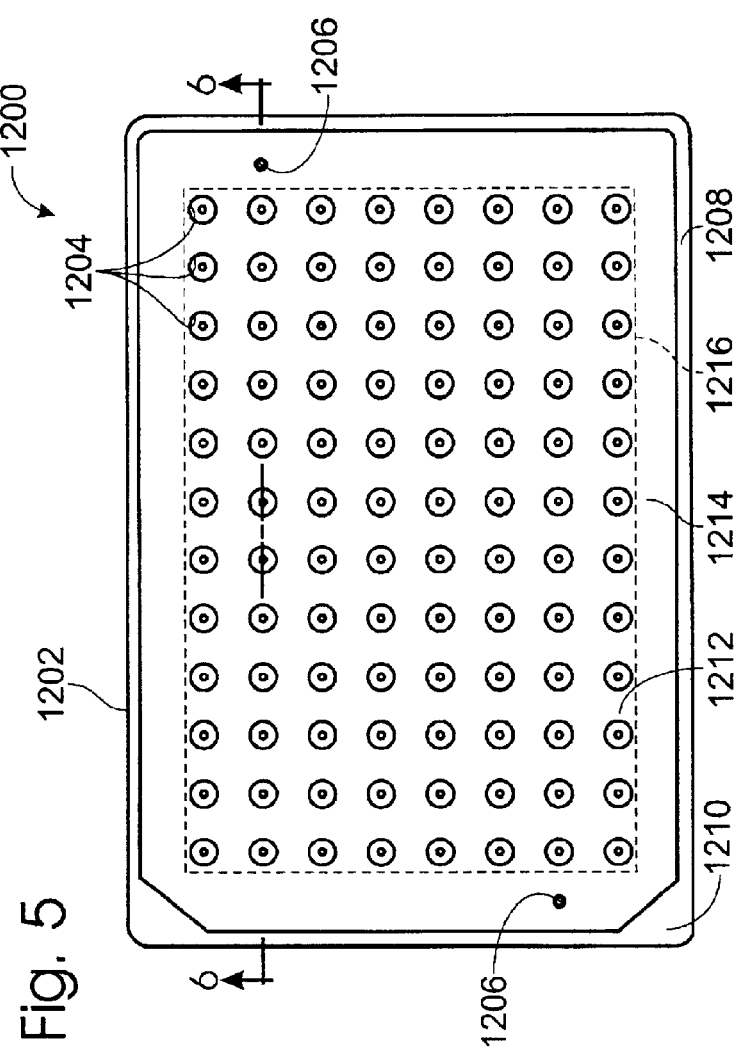
FIG. 5 is a top view of a 96-well microplate constructed in accordance with aspects of the invention.

FIG. 5 is a top view of a 96-well microplate 1200 constructed in accordance with aspects of the invention. Microplate 1200 includes a frame 1202 and a plurality of sample wells 1204 disposed in the frame. In some embodiments, microplate 1200 may include one or more reference fiducials 1206 disposed in the frame.

Frame 1202 is the main structural component of microplate 1200. The frame may have various shapes and various dimensions. In microplate 1200, frame 1202 is substantially rectangular, with a major dimension X of about 127.8 mm and a minor dimension Y of about 85.5 mm. Tolerances in plate dimensions typically are about ±0.5–1.0 mm for polystyrene plates, but may increase to about ±2 mm for polypropylene plates, especially if the polypropylene plates are produced using molds designed for polystyrene plates. Frame 1202 may be adapted for ease of use and manufacture. For example, frame 1202 may include a base 1208 to facilitate handling and/or stacking, and frame 1202 may include notches 1210 to facilitate receiving a protective lid. Frame 1202 may be constructed of a material, such as a thermoplastic, that is sturdy enough for repeated, rugged use and yet minimally photoluminescent to reduce background upon illumination.

Frame 1202 includes a sample well region 1212 and an edge region 1214 forming a perimeter 1216 around the sample well region. Sample wells may be disposed in the sample well region in various configurations. In microplate 1200, sample wells 1204 are disposed in sample well region 1212 in a substantially rectangular 8×12 array, with a pitch (i.e., center-to-center interwell spacing) along both X and Y of about 9 mm. This pitch corresponds to a density of wells of about one well per 81 mm$^2$.

Reference fiducials 1206 may be used for identification, alignment, and/or calibration of the microplate. Reference fiducials may be disposed in the sample well region and/or the edge region in various configurations. In microplate 1200, reference fiducials 1206 are disposed in edge region 1214, substantially aligned with a row of sample wells along the X dimension, although reference fiducials also may be offset from the rows of sample wells. Reference fiducials preferentially are positioned in corners of the microplate, near where optical analysis begins, so that they may quickly be identified and analyzed. Reference fiducials may be positioned in rotationally symmetric positions, so that microplates may be loaded into an optical device and analyzed backwards without difficulty. Alternatively, reference fiducials may be positioned in rotationally asymmetric positions, so that the system can ascertain which way the microplate is oriented; information on orientation is useful because samples typically are not positioned symmetrically within the microplate. Further aspects of reference fiducials are described in PCT Patent Application Ser. No. PCT/US99/08410, filed Apr. 16, 1999, which is incorporated herein by reference.

Figure 6:
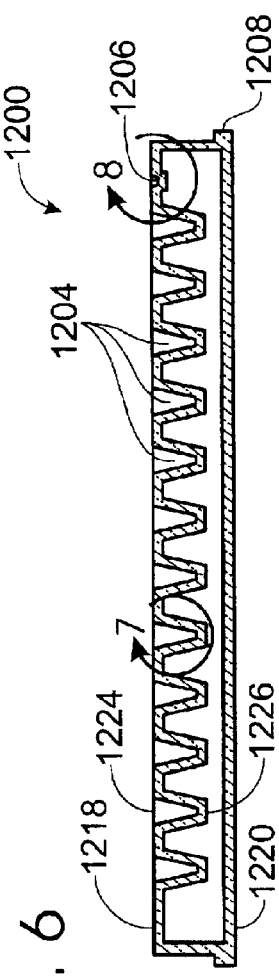
FIG. 6 is a cross-sectional view of the microplate in FIG. 5, taken generally along line 6—6 in FIG. 5.
Figure 14:
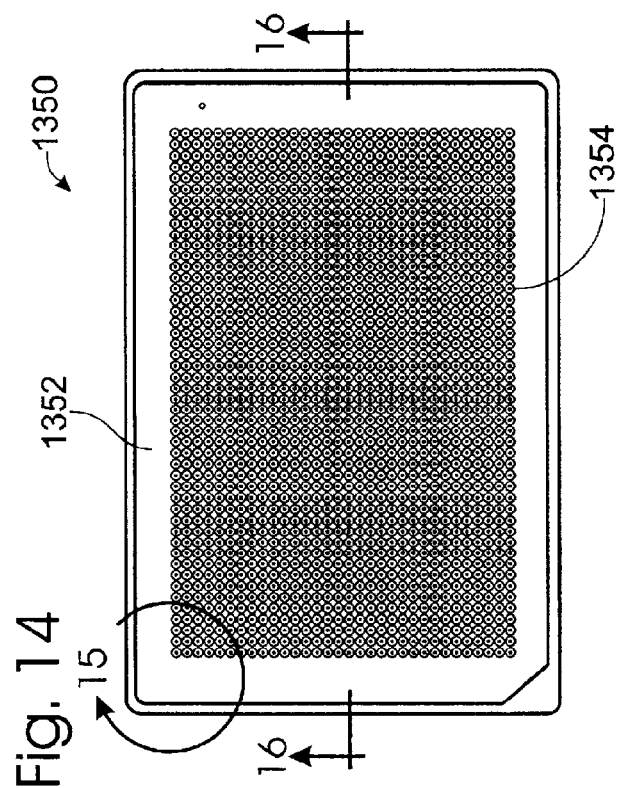
FIG. 14 is a top view of the microplate in FIG. 13.
Figure 16:
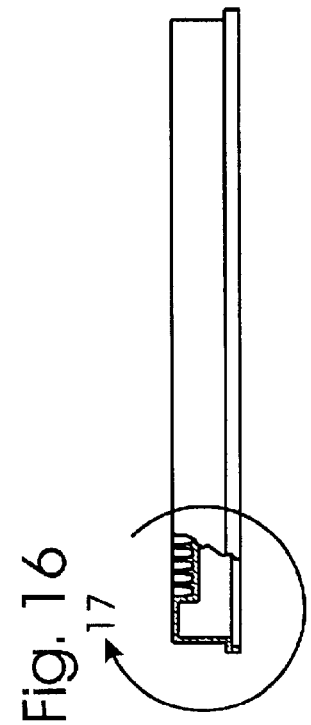
FIG. 16 is a cross-sectional view of the microplate in FIG. 14, taken generally along line 16—16 in FIG. 14.
Figure 15:
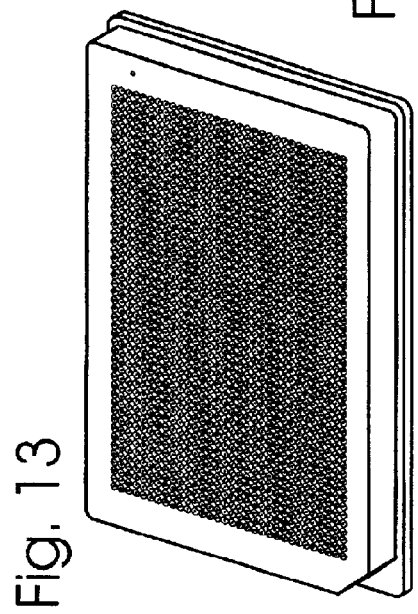
FIG. 15 is an enlarged portion of the top view in FIG. 14, showing details of the sample wells.
Figure 13:
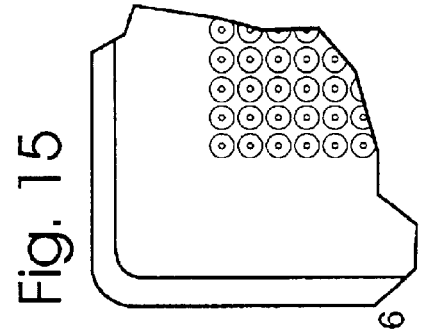
FIG. 13 is a perspective view of a 1536-well microplate constructed in accordance with the invention.
Figure 17:
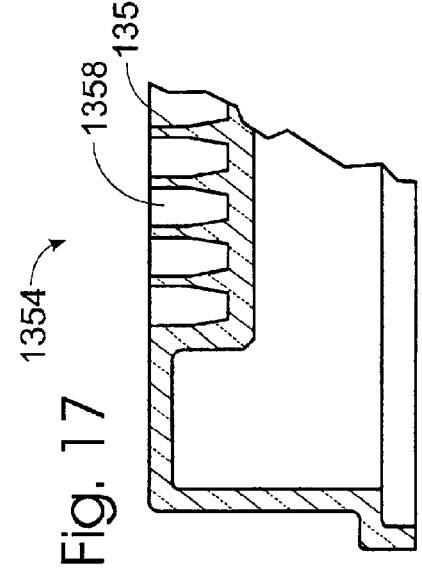
FIG. 17 is an enlarged portion of the cross-sectional view in FIG. 16, showing details of the sample wells.

FIG. 6 is a cross-sectional view of microplate 1200, showing sample wells 1204, reference fiducial 1206, and base 1208. In microplate 1200, frame 1202 has a top 1218, a substantially parallel bottom 1220, and substantially perpendicular sides 1222. Top 1218 may have various shapes, although it typically is flat. (Top 1218 may be surrounded by a raised edge to facilitate stacking.) Frame 1202 has a height H of about 12 mm, corresponding generally to the separation between top 1218 and bottom 1220. Tolerances in plate height typically are about 0.5 mm or less. Sample wells 1204 are disposed with open, optically transparent ends 1224 directed toward top 1218, and closed, optically opaque ends 1226 directed toward bottom 1220. In some embodiments, optically opaque ends 1226 may be replaced by optically transparent ends to permit bottom illumination and/or detection. Reference fiducial 1206 is disposed on top 1218, although reference fiducials also may be disposed on bottom 1220 and/or sides 1222.

The preferred plate height is determined by a variety of considerations. Generally, taller plates with elevated bottoms and/or filled wells put the samples closer to the detector for analysis, increasing numerical aperture and hence signal. Conversely, shorter plates allow more plates to be stacked into processing bins for longer periods of unattended operation. The specified height of about 12 mm generally is large enough to facilitate handling by sample handlers and/or a stage, and yet small enough to permit optical analysis of the entire well. Moreover, the specified height generally is sufficient to ensure that the microplates are sufficiently flat for analysis.

Figure 7:
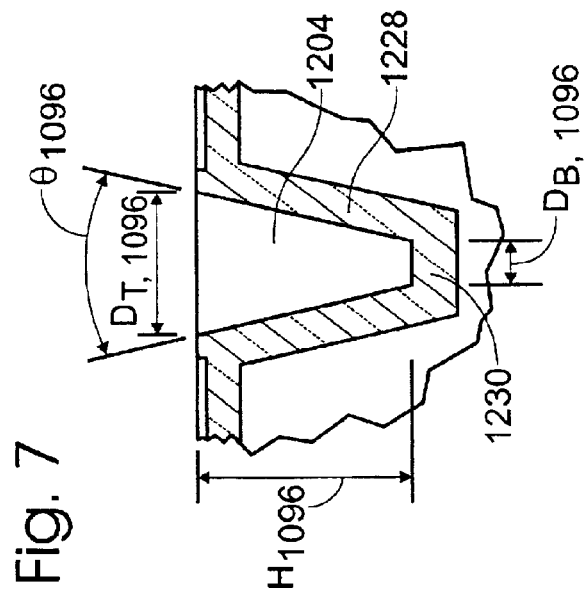
FIG. 7 is a first enlarged portion of the cross-sectional view in FIG. 6, showing details of a sample well.

FIG. 7 is a first enlarged portion of the cross-sectional view in FIG. 6, showing details of sample wells 1204. Sample wells may have various shapes and various dimensions, as described in detail in subsequent sections. In microplate 1200, sample wells 1204 are substantially frusto-conical, with substantially straight side walls 1228 and a substantially flat bottom wall 1230. In microplate 1200, optically opaque ends 1226 are positioned about 6.7 mm below top 1218, and about 5.3 mm above bottom 1220. Sample well 1204 is characterized by a top diameter $D_{T,96}$, a bottom diameter $D_{B,96}$, a height $H_{96}$, and a cone angle $\theta_{96}$. Here, $\theta_{96}$ is the included angle between side walls 1228. In microplate 1200, $D_{T,96}$ is about 4.5 mm, $D_{B,96}$ is about 1.5 mm, $H_{96}$ is about 6.7 mm, and $\theta_{96}$ is about 25.4°. Sample well 1204 has a total volume of about 50 µL, and a smallest practical working volume of about 1–40 µL.

Figure 8:
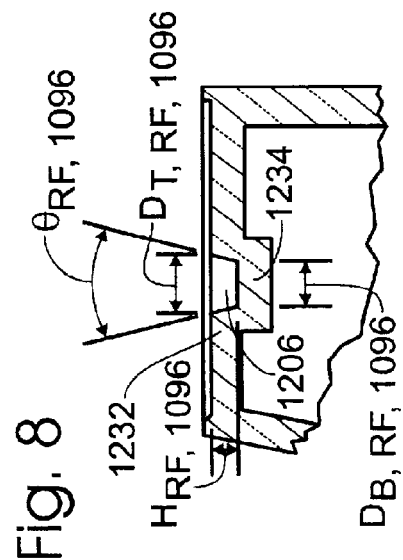
FIG. 8 is a second enlarged portion of the cross-sectional view in FIG. 6, showing details of a reference fiducial.

FIG. 8 is a second enlarged portion of the cross-sectional view in FIG. 6, showing details of reference fiducial 1206. Reference fiducials may have various shapes and various dimensions, as described in detail in subsequent sections. In microplate 1200, reference fiducial 1206 is substantially frusto-conical, with substantially straight side walls 1232 and a substantially flat bottom wall 1234. Reference fiducial 1206 is characterized by a top diameter $D_{T,RF,96}$, a bottom diameter $D_{B,RF,96}$, a height $H_{RF,96}$, and a cone angle $\theta_{RF,96}$. Here, $D_{B,RF,96}$ and $\theta_{RF,96}$ are substantially equal to $D_{B,96}$ and $\theta_{96}$, the corresponding values for sample well 1204. $H_{96}$ is about 1 mm, and $D_{T,RF,96}$ is specified by the other parameters. In some applications, the reference fiducial may contain a luminescent material or solution so that it is easier to locate. In other applications, the reference fiducial may be used as a blank for determining background, or as an additional sample well for holding an additional sample. In these applications, the reference fiducial may be located and/or analyzed using the same optical system used to analyze samples in conventional sample wells.

2. 384-Well Microplates

FIGS. 9–12 are views of a 384-well microplate 1300 constructed in accordance with aspects of the invention. Microplate 1300 is similar in many respects to microplate 1200 and includes a frame 1302 and a plurality of sample wells 1304 disposed in a sample well region 1312 of the frame. In some embodiments, microplate 1300 may include one or more reference fiducials 1306 disposed in an edge region 1314 or other region of the frame.

The external dimensions of microplate 1300 are similar to the external dimensions of microplate 1200. However, the density of sample wells in microplate 1300 is four times higher than the density of sample wells in microplate 1200. Consequently, the pitch (i.e., the center-to-center interwell spacing) in microplate 1300 is about 4.5 mm, or about one-half the pitch in microplate 1200. This pitch corresponds to a density of wells of about four wells per 81 mm$^2$. In microplate 1300, reference fiducial 1306 is positioned about midway between two rows of sample wells along the X direction; in contrast, in microplate 1200, reference fiducial 1206 is positioned about in line with a row of sample wells along the X direction. This is because the reference fiducials are positioned in approximately the same position in each microplate, but the center line of one row of sample wells in microplate 1200 because the center line between two rows of sample wells in microplate 1300 as the density of wells is quadrupled.

Sample wells 1304 in microplate 1300 are similar to sample wells 1204 in microplate 1200. Sample wells 1304 may be characterized by a top diameter $D_{T,384}$, a bottom diameter $D_{B,384}$, a height $H_{384}$, and a cone angle $\theta_{384}$. The preferred values of $D_{B,384}$ and $\theta_{384}$ for microplate 1300 are substantially similar to the preferred values of $D_{B,96}$ and $\theta_{96}$ for microplate 1200. However, the preferred value for $D_{T,384}$, which is about 4.7 mm, is smaller than the preferred value for $D_{T,384}$, which is about 6.7 mm. In microplate 1300, the upper diameter must be smaller than the upper diameter of the sample wells in microplate 1200, because the sample wells are close packed, leaving no more interwell spacing than necessary for moldability. In turn, the preferred value for $H_{384}$ is about 4.7 mm, so that the wells are elevated by about 7.3 mm. Sample well 1304 has a total volume of about 25 µL, and a smallest practical working volume of about 1–12 µL.

Reference fiducial 1306 in microplate 1300 may be essentially identical to reference fiducial 1206 in microplate 1200.

3. 1536-Well Microplates

FIGS. 13–17 are views of a 1536-well microplate 1350 constructed in accordance with aspects of the invention. Microplate 1350 is similar in many respects to microplates 1200 and 1300, and includes a frame 1352 and a plurality of sample wells 1354 disposed in the frame. The pitch in microplate 1350 is about 2.25 mm, or about one-half the pitch in microplate 1300 and about one-fourth the pitch in microplate 1200. This pitch corresponds to a density of wells of about sixteen wells per 81 mm$^2$.

Sample wells 1354 may be exclusively frusto-conical, like sample wells 1204 in microplate 1200 and sample wells 1304 in microplate 1300. However, due to spatial constraints, the volume of such wells would have to be small, about 1–2 µL. Smaller wells are easier to mold and keep within tolerances, but they provide less flexibility and place more stringent demands on fluid dispensing and analytical equipment. Alternatively, sample wells 1354 may have a frusto-conical lower portion 1306 coupled to a cylindrical upper portion 1308. The volume of such wells may be larger, for example, about 7–8 µL. Larger wells are more difficult to mold, but they permit use of a wider range of sample volumes and therefor a wider range of assay formats. Larger sample volumes may be useful if the microplate is used in conjunction with standard fluid dispensing equipment, because the standard equipment may have difficulty dispensing small volumes. Larger sample volumes also may be useful if reagents are to be added to the well from stock solutions, such as 100×DMSO or DMF stock solutions, because they make it less necessary to dispense very tiny amounts of stock solution to obtain adequate dilution. Larger sample volumes also may be useful for cell-based assays, because cells may live longer in a larger volume of medium.

Reference fiducials in microplate 1350 may be essentially identical to reference fiducials 1206 in microplate 1200 and reference fiducials 1306 in microplate 1300. However, reference fiducials in microplate 1350 may be more important than reference fiducials in plates 1200 and 1300 because the well dimensions in microplate 1350 may approach the molding tolerances, making it more likely that wells will be significantly displaced from their nominal positions.

4. Miscellaneous Microplates

The system and its components also may be designed for use with some or all of the following microplates:

(a) A microplate having a frame portion and a top portion, where an array of wells is formed in the top portion. The wells are organized in a density of at least about 4 wells per 81 mm$^2$. Each well has a bottom wall that is elevated at least about 7 millimeters above a plane defined by a bottom edge of the frame.

(b) A microplate having an array of conical wells organized in a density of at least about 4 wells per 81 mm$^2$.

(c) A microplate having an array of conical wells, where each well has a maximum volume capacity of less than about 55 microliters. A preferred small-volume well design has a volume capacity of 1–20 microliters.

(d) A microplate having an array of wells in the top portion, where each well has a maximum volume capacity of less than about 55 microliters and a well bottom that is elevated at least about 7 millimeters above a plane defined by a bottom edge of the frame.

(e) A microplate having an array of wells in a top portion, organized in a density of at 2 least about 4 wells per 81 mm$^2$, where each well has a conical portion characterized by a cone angle of at least about 8°.

(f) A microplate having an array of conical wells characterized by a cone angle $\theta$, where $\theta=2\arcsin(NA/n)$ and NA is equal to or greater than about 0.07.

(g) A microplate having an array of wells organized in a density of at least about 16 wells per 81 mm$^2$, where each well has a frusto-conical bottom portion and a substantially cylindrical upper portion.

(h) A microplate comprising a frame and a plurality of frusto-conical sample wells disposed in the frame, where the sample wells are characterized by a cone angle of at least about 8°. The microplate further may include a reference fiducial that provides information to facilitate sample analysis.

(i) A microplate having 864 sample wells, 3456 sample wells, or 9600 sample wells.
(j) A microplate formed of black, white, or clear material, or a combination thereof.
(k) A microplate suitable for performing PCR.

B. Transport Module

Figure 18:
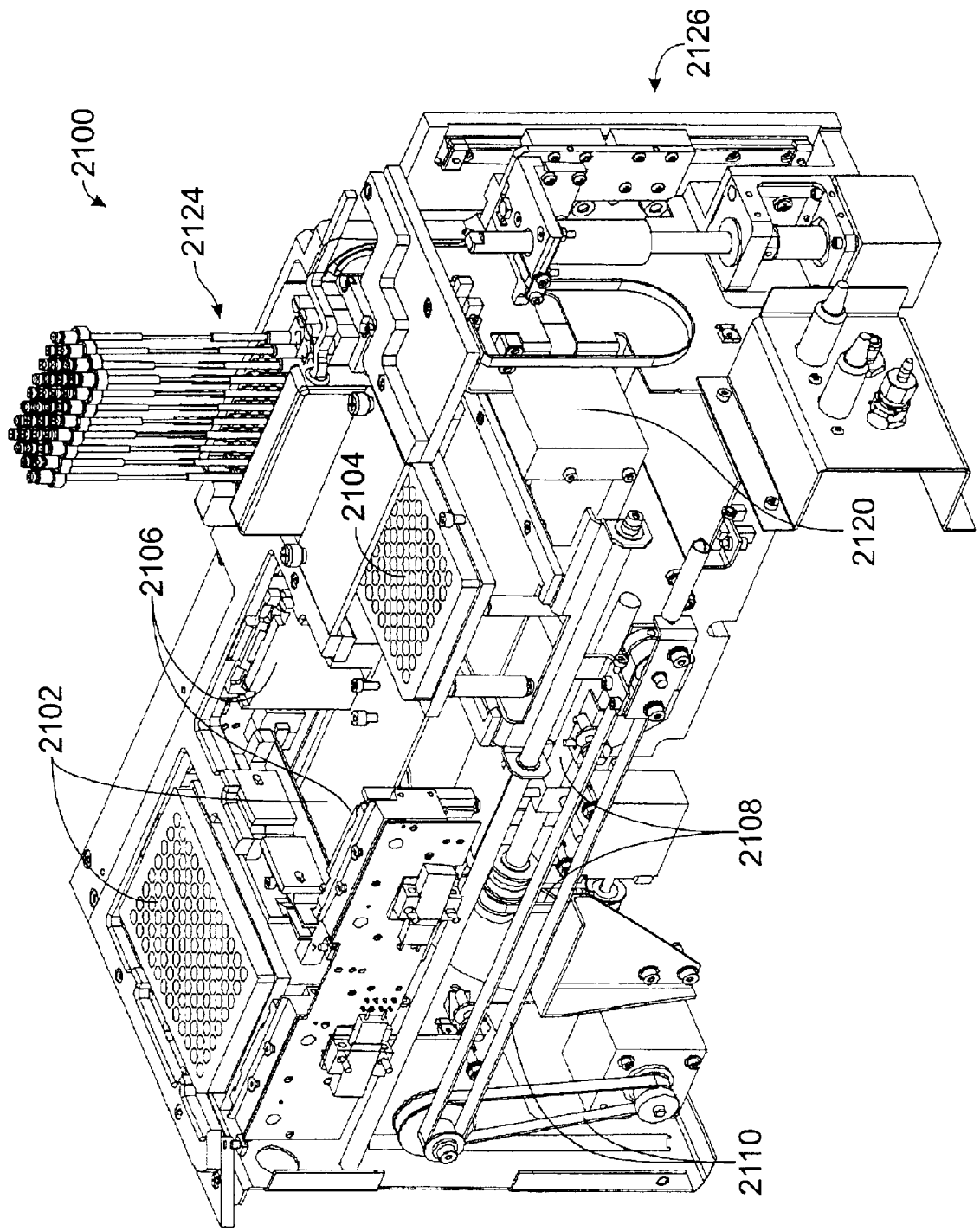
FIG. 18 is a partial perspective view of a transport module constructed in accordance with aspects of the invention.

FIG. 18 shows a transport module 2100 constructed in accordance with aspects of the invention. The transport module generally comprises any mechanism or system for automatically shuttling a plate or other sample holder between an I/O site and one or more function or transfer sites. The transport module may enhance convenience by reducing human intervention and enhance throughput by reducing the time required to process multiple samples.

The transport module may include one or more I/O sites 2102, one or more function or transfer sites 2104, and mechanisms for moving plates between the I/O and function sites. An I/O site is a site at which sample holders are input and/or output. A function site is a site at which one or more functions are performed, such as fluid dispensing, analysis, cleaning, containment, and/or incubation, among others. A transfer site is a site at which a sample holder is transferred to a transport mechanism (independently) associated with a function module. The mechanisms for moving plates may include a latch mechanism 2106, an intrasite driver 2108, and/or an intersite driver 2110. The latch mechanism may be used for singulating plates from and to stacks of plates. The intrasite and intersite drivers may be used for moving plates between and within sites, respectively. These latch mechanism and drivers may share features and/or components, or be substantially or totally independent.

The transport module also may include other features, such as a barcode reader 2120 for reading an informational barcode optionally associated with a plate, a plate sensor for detecting the presence of a plate at one or more sites within the transport module, and one or more interfaces for interactions with function modules. The plate sensors may be positioned at one or more sites and may be configured to accommodate variations in plate thickness, color, and so on. The interfaces may include mounting sites for a dispense head 2124 and/or a dispense driver 2126 associated with a fluidics function module.

The transport module may employ a variety of singulation strategies, depending in part on the number of I/O sites, the nature of the I/O sites (i.e., input, output, or both), and the location in the stack from which plates are taken and/or added (typically bottom and/or top). Transport module 2100 has two I/O sites, from which plates are taken and/or added at the bottom. Typically, but not necessarily, one of these sites is dedicated to input, and the other is dedicated to output. To input a plate, a robot (1) removes a plate from the bottom of an input stack of plates at the input site, (2) transports the plate to the transfer site, and (3) transfers the plate at the transfer site to a transport mechanism for an associated function module. To output a plate, the robot (1) takes the plate from the transport mechanism for the function module at the transfer site, (2) transports the plate to the output site, and (3) transfers the plate at the output site to the bottom of an output stack of plates at the output site. In transport module 2100, these functions are performed by the intersite and intrasite drivers, with preferred throughputs ranging from about 1 second per plate to about 5 seconds per plate.

Further aspects of the transport module are described in the following sections: (1) latch mechanisms, (2) intrasite drivers, (3) intersite drivers, (4) additional features, and (5) examples.

1. Latch Mechanisms

The latch mechanism generally comprises any mechanism for inputting a single plate from a stack of plates and/or outputting a single plate to a stack of plates. The following description addresses (a) the actuation mechanism employed by the latch mechanism, and (b) general attributes of the latch mechanism.

a. Actuation Mechanism

Figure 19:
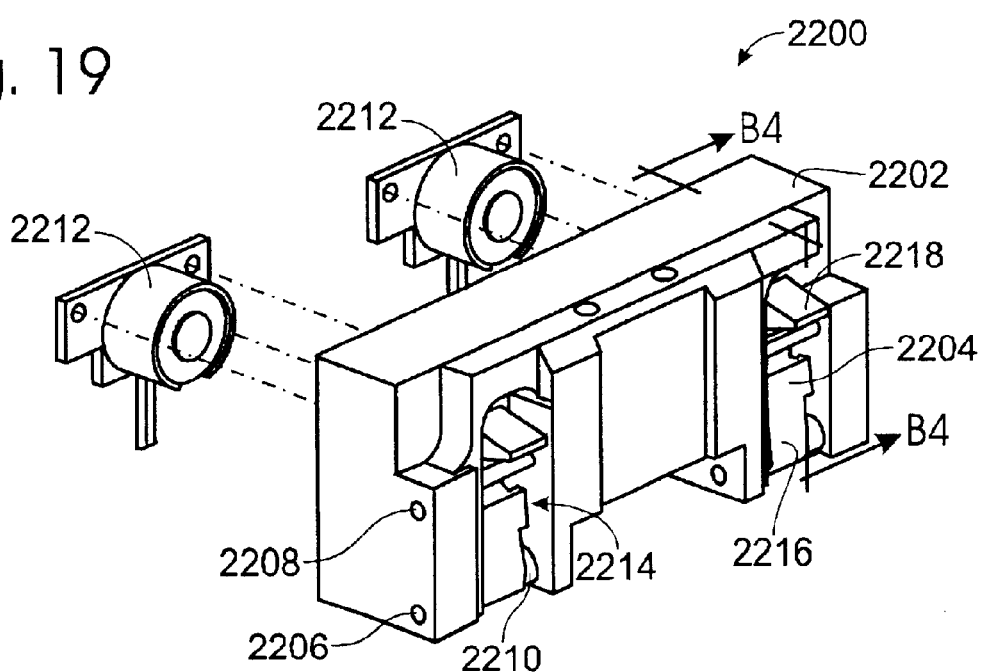
FIG. 19 is a partially exploded perspective view of a latch mechanism from the transport module of FIG. 18.

FIG. 19 shows an exemplary latch mechanism 2200 for used in the I/O sites. Latch mechanism 2200 includes a latch body 2202 and complementary pairs of latches 2204, pivot pins 2206, retaining pins 2208, torsion springs 2210, and electromagnets 2212. The latch body is an elongate substantially rectangular structure that includes an inward-facing recess 2214 adjacent each end. The latches are elongate structures that include a pivot portion 2216 and a pick portion 2218. The latches are pivotably mounted in recesses 2214 so that the pivot portion is mounted about the pivot pin and the pick portion is free to pivot through an angle determined by the retaining pin at one extreme and the electromagnet at the other extreme.

The latch mechanisms generally are used in pairs to support opposite sides of a plate, and each latch mechanism includes two latches to support opposite ends of a single side of the plate. As described below, this combination of two lifters and four latches cooperates to singulate single plates from and to the bottom of a stack of plates.

Figure 20:
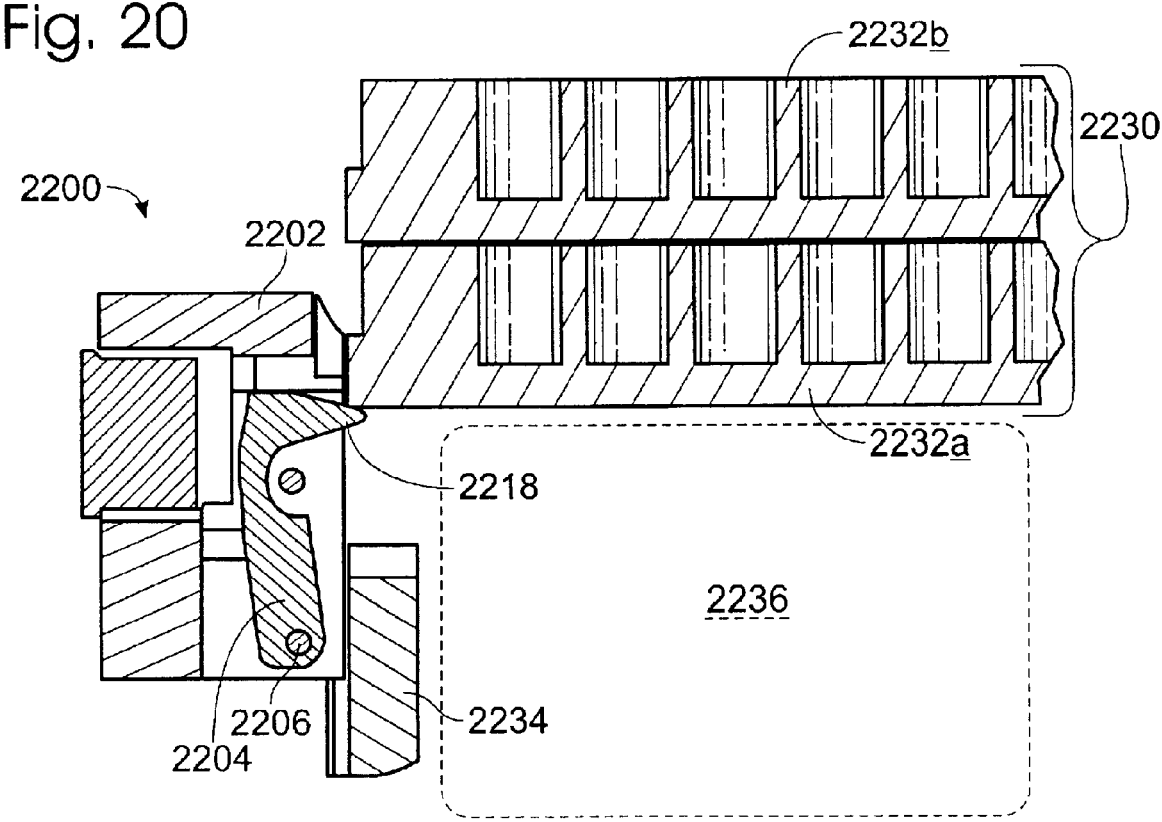
FIG. 20 is a cross-sectional view of the latch mechanism of FIG. 19, taken generally along line 20—20 in FIG. 19, showing the latch mechanism in use supporting a stack of plates.

FIG. 20 shows latch mechanism 2200 in use to support a stack 2230 of plates 2232a,b, which rest atop pick portions 2218 of latches 2204 and generally above a lifter 2234. The pick portions are biased inboard of latch body 2202 and into the cavity 2236 of the corresponding I/O site to support the plates by the torsion springs (not shown). The latch also may be biased toward this position by other mechanisms, including counterweights, electromagnets, and other types of springs. The latch also may be biased toward this position by having a center of gravity above and inward of pivot pin 2206.

FIG. 21 shows a four-step input cycle for inputting (or singulating) a plate using the transport module and associated latch mechanisms. Plates may be input from a stack before fluid dispensing and analysis, and after incubation, among others.

Step 1. The first input step (Panel A) comprises raising lifters 2234 to elevate a stack 2230 of plates 2232a,b through contact of the plates with an upper surface 2240 of the lifters and to push latches 2204 into a retracted position through contact of the latches with a side surface 2242 of the lifters. In the depicted embodiment, the lifters are raised from their resting height to their maximum height (about 5 mm), after which electromagnets 2212 behind each latch are energized to hold the latch in the retracted position. In other embodiments, the latches may be moved to and/or held in the retracted position at alternative times and/or by alternative mechanisms, such as a solenoid-actuated pin. If it is unnecessary to reverse the function of the latch (for example, because the latch is used only for input), the latch may be held in the retracted position by eliminating a notch 2244 in the lifter that otherwise permits the pick portion of the latch to move under the plates.

Step 2. The second input step (Panel B) comprises lowering lifters 2234 to lower stack of plates 2230. After pick portion 2218 of latch 2204 has passed below a bottom edge 2250 of input plate 2232a, the latches are released by de-energizing electromagnets 2212, so that the pick portion falls against and then rides along a side 2252 of the plate. The electromagnets thus control release of the latch without moving parts. The input plate is the bottommost plate in the stack of plates. Input-only latches, which lack a top notch, will ride along the side of the lifter and then fall against and ride along the side of the plate automatically.

Step 3. The third input step (Panel C) comprises further lowering lifters 2234, with pick portion 2218 of latch 2204 continuing to ride along the side of input plate 2232a. The pick portion will follow the contour of the plate, eventually falling onto the narrower upper section of the plate, where the pick portion will be positioned below a bottom surface 2260 of the second to the bottommost plate 2232b in the stack.

Step 4. The fourth input step (Panel D) comprises further lowering lifters 2234 until input plate 2232a moves below pick portion 2218 of latch 2204 and the pick portion contacts bottom surface 2260 of second to the bottommost plate 2232b. The latch thereby catches the next plate, preventing it from dropping, while the input plate remains on the lifter for further lowering. Thus, the lifter retains a single plate, and the latch retains the rest of the original stack of plates. The angle of the top of the latch may be such that the normal force from the weight of the stack is directed through pivot pin 2206, so that no additional moments are induced on the latch. At this point, a plate has been singulated for further transport to a dispense site, an analysis site, or an auxiliary site, as desired.

FIG. 22 shows a four-step output cycle for outputting a plate using the transport module and associated latch mechanism. Plates may be output after fluid dispensing and/or analysis, among others. The latch mechanism functions passively as an output latch but actively as an input latch, in that the electromagnets are not energized during the output cycle but are energized for a brief portion of the input cycle down stroke.

Step 1. The first output step (Panel A) comprises positioning an output plate 2280a (i.e., a plate to be output) on lifter 2234 and raising the lifter to elevate the plate so that it is positioned beneath the bottommost plate 2280b in a stack of plates 2282 to which it is to be added or returned. As the lifters raise the plate, latches 2204 are pushed out of the way by the outer contour of the plate.

Step 2. The second output step (Panel B) comprises further raising lifter 2234 until a top surface 2290 of output plate 2280a contacts a bottom surface 2292 of bottommost plate 2280b in stack 2282. The new stack is then lifted above latch 2204.

Step 3. The third output step (Panel C) comprises lowering lifter 2234 so that pick portion 2218 of latch 2204 can drop into notch 2244 in the lifter, thereby positioning itself beneath the new stack of plates 2282'.

Step 4. The fourth output step (Panel D) comprises further lowering lifter 2234 to its resting position, leaving output plate 2280a in stack 2282'.

Except as noted above, the output cycle generally resembles the input cycle. The lifter mechanism raises the plate by a fixed amount, thereby causing it to pass the four spring-loaded latches, which retract as the plate is raised by the lifter. Once the bottom of the plate is above the top of the latch, the latches are released, and a spring on each latch causes the latch to extend under the plate. The lifter mechanism then is lowered, causing the plate to be captured by the now extended latches. The up-stacked plate thus is added to the bottom of the output stack.

b. General Attributes of the Latch Mechanism

The latch mechanism may be configured to have a low inherent sensitivity to the exact size, shape, construction material, and surface finish of the plate. For example, the four inwardly sloping, tapered (or angled) latches may cause the stack of plates to self-center within the plate-input area to accommodate both relatively small and large plate sizes. Moreover, the mechanism may drop the plate gently onto the lifter when the singulation mechanism disengages from the edges of the plate, so that the plate may be lowered to the intrasite driver without spilling fluid from the wells. Moreover, if the ends of the latches are sufficiently smooth, the latches should not exert enough frictional force on the edges of the plate to cause the plate to tilt or otherwise hang up as the lifter mechanism is lowered and the plate is placed on the intersite driver. A flexible latch mechanism is important because it facilitates use of a wider variety of plates and other sample holders with a reduced likelihood of failure. The depicted mechanism is especially suited for use with the microplates described above.

The lifters associated with the latch mechanism generally may be activated using any suitable mechanism. In the depicted embodiment, the lifters are activated using a spring and electromagnet. In alternative embodiments, the lifters may be activated by gravity. In such an alternative embodiment, the latches may pivot on their support pins such that their centers of gravity are offset. Consequently, when the lifter mechanism is lowered, the latches are activated by gravity to return to their nonretracted or extended state, thereby preventing the next plates in the stack from dropping as the lifter mechanism is lowered. If the offset in the center of gravity of the latches is only enough to cause the latches to return to their extended positions, they should press only very lightly on the edges of the plate as it drops.

2. Intrasite Drivers

Figure 23:
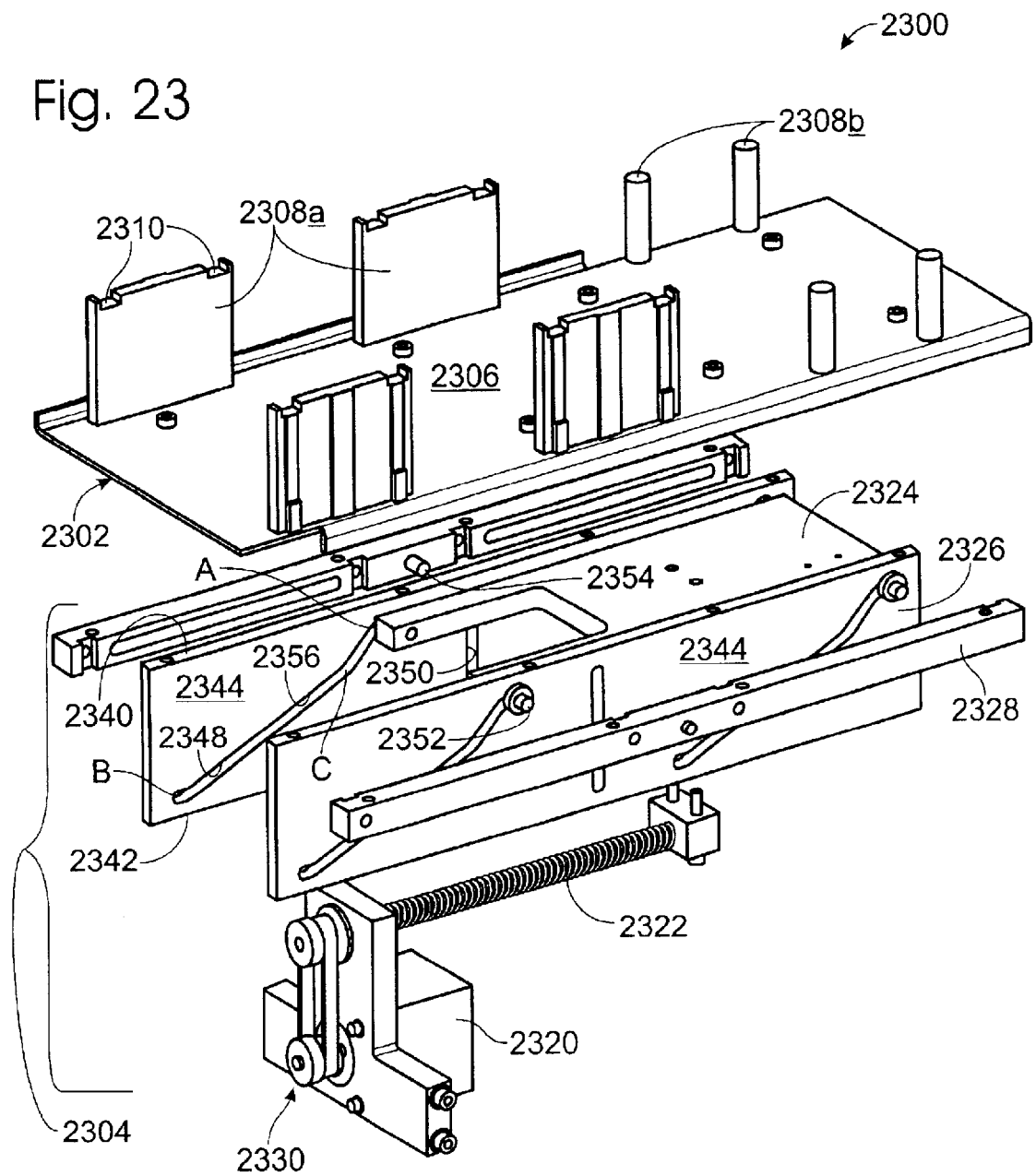
FIG. 23 is a partially exploded perspective view of an intrasite driver from the transport module of FIG. 18.

FIG. 23 shows an intrasite driver 2300, which generally comprises any mechanism for moving samples within an I/O and/or function or transfer site, especially in cooperation with a latch or singulation mechanism. Intrasite driver 2300 includes a lift platform 2302 for raising and lowering plates and a drive mechanism 2304 for raising and lowering the lift platform.

Lift platform 2302 includes a base 2306 and sets of lifters 2308a,b corresponding to each I/O and/or function site. The lifters generally comprise any mechanism configured to raise or lower a plate in cooperation with a singulation mechanism. Lifters 2308a for use in the I/O sites are substantially rectangular and include a top notch 2310 for interaction with a latch, as described above. Lifters 2308b for use in the function site are substantially cylindrical and may be used to raise and lower a plate for transfer to a transport mechanism associated with a function module, as described below.

Drive mechanism 2304 includes a rotary drive motor 2320, an Acme screw 2322, a slide 2324, a pair of opposed cam units 2326, and a pair of opposed guides 2328. These elements cooperate as described below to produce a lifting force for raising and lowering lift platform 2302 and thus raising and lowering a plate. Here, rotary motion produced by motor 2320 is converted to horizontal linear motion by Acme screw 2322, and the horizontal motion is in turn converted to variable-rate vertical motion by cam units 2326.

The rotary drive motor and Acme screw together form a linear actuator, which generally comprises any mechanism for producing a linear force or displacement, including a positioning table, a rodless cylinder, a robot module, an electric thrust cylinder, a pneumatic cylinder, a linear motor, a linear voice coil, and a solenoid. Here, the role of the rotary drive motor may be performed by any mechanism capable of producing rotary motion, including a motor, gear motor, gear reducer, manual hand crank, and micrometer, among others. Similarly, the role of the Acme screw may be performed by any mechanism capable of converting rotary motion to linear motion. An Acme screw is a preferred mechanism for converting rotary motion to linear motion because the Acme screw performs this function using direct sliding friction, which helps to hold the load in position. In contrast, a belt drive or ball screw may permit a load to back drive due to gravity when no torque is applied to the motor. The Acme screw is an elongate structure that is connected at a first end through an intermediate pulley system 2330 to drive motor 2320 and at a second end to slide 2324.

The cam units 2326 are substantially rectangular and include a top edge 2340, a bottom edge 2342, and a pair of opposed side walls 2344. The side walls include two sloped drive channels 2348, which function as the cams, and a vertical guidance channel 2350. A drive pin 2352 is inserted through each drive channel 2348, and a guide pin 2354 is inserted through the guide channel 2350. In alternative embodiments, pins and channels may be replaced with other components, including ridges, bearings, or rollers. Drive pins 2352 inserted into drive channels 2348 are connected to slide 2324 on an inner side and to guides 2328 on an outer side. In turn, slide 2324 is connected through the Acme screw and pulley system to drive motor 2320, and the guides are connected through the lift platform to lifters 2308a,b. The driver motor moves drive pins 2352 through drive channels 2348 between a top position "A" closer to top edge 2340 and a bottom position "B" closer to bottom edge 2342. The drive pins are constrained to move horizontally, so that the pins push against an interior side 2356 of drive channels 2348, urging cam unit 2326 to move both horizontally and vertically. Guide pins 2354 inserted into guidance channels 2350 are connected to relatively fixed portions of the transport module, preventing horizontal motion, but permitting vertical motion, so that cam unit 2326 only moves vertically. As pin 2352 moves between positions A and B, the pin moves a horizontal distance H and a vertical distance V. It is the vertical displacement that creates the raising and lowering motions. H and V may be optimized for particular plates and travel distances; in transport module 2100, H and V are optimized for standard microplates and are approximately 10 cm and 3.5 cm, respectively. Cam unit 2326 is raised when drive pin 2352 is close to position A, and cam unit 2326 is lowered when drive pin 2352 is close to position B.

In use, a drive motor moves pins 2352 horizontally at a substantially uniform rate; consequently, the slope of drive channel 2348 determines the mechanical advantage and the rate of vertical motion. Close to positions A and B, the slope of drive channel 2348 is substantially zero, so that there is substantially no vertical motion. Stated differently, close to positions A and B, a preselected vertical position corresponds to a range of horizontal positions. This configuration makes the vertical position relatively insensitive to motor precision or manufacturing tolerance, because the lifter will be at the same vertical position whenever it simply is near positions A or B. Between positions A and B, the slope of drive channel 2348 is nonzero, so that there is vertical motion. The slope is largest (approximately 30°) between position A and an intermediate position "C," so that the lifter raises and lowers relatively rapidly when it is farthest from the bottom of the stack of plates. The slope is smallest (approximately 15°) between positions B and C, so that the lifter raises and lowers relatively slowly when it is nearest to the bottom of the stack of plates.

The drive motor generally comprises any mechanism configured to generate a driving motion, as described above. The drive motor used in transport module 2100 is a stepper motor, which generates a constant torque. Generally, stepper motors and cams provide alternative mechanisms for performing the same function, in this case, generating a varying rate of motion. However, pairing a stepper motor and cam together in the invention provides several advantages. In particular, the cam provides mechanical advantage and positional insensitivity, and permits the stepper motor to be run at an optimal velocity profile. If the stepper motor were used alone, a much larger motor would be required to produce the required forces. Conversely, if the cam were used alone, with a nonstepper motor, a system of limit switches would be required to limit travel and provide positional feedback to release the latches.

3. Intersite Drivers

Figure 24:
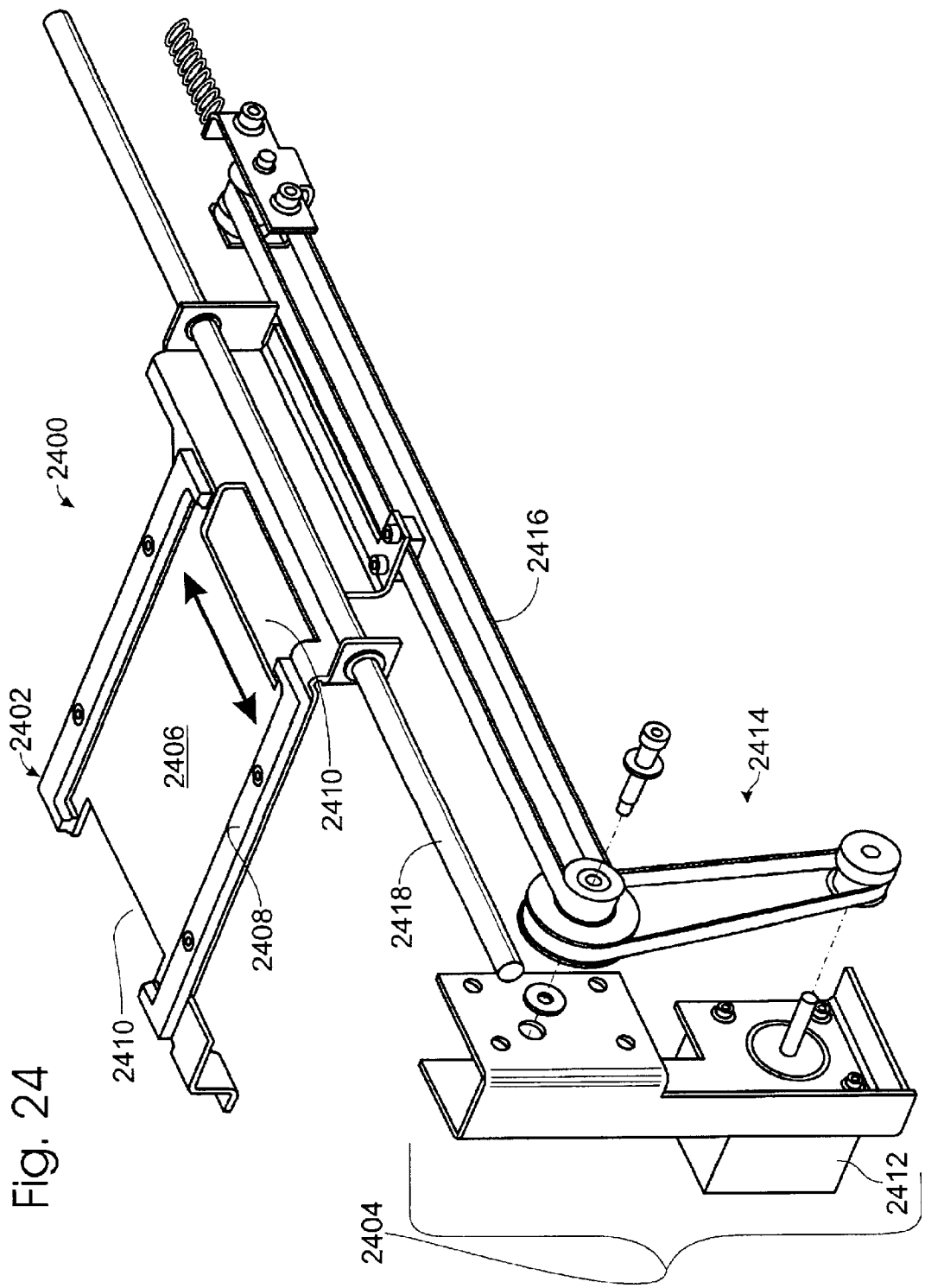
FIG. 24 is a partially exploded perspective view of an intersite driver from the transport module of FIG. 18.

FIG. 24 shows an intersite driver 2400, which generally comprises any mechanism for moving samples between different I/O and/or function sites. Intersite driver 2400 includes a tray 2402 for supporting a plate and a shuttle mechanism 2404 for moving the tray (and an associated plate) between I/O and/or function or transfer sites. The tray may include a substantially planar platform 2406 to support the plate and a rim-like plate guide 2408 that partially surrounds the platform to position and partially secure the plate. The tray also may include apertures (or recesses) 2410 for passage of a lifter (such as lifters 2308a,b in FIG. 23) from an intrasite driver for use in raising or lowering plates supported by the tray. The shuttle mechanism includes a motor 2412, a pulley system 2414, a drive belt 2416, and a guide shaft 2418. The motor is connected to the drive belt through the intermediate pulley system. The tray is connected to the drive belt and slidingly mounted about the guide shaft.

In use, the motor turns the intermediate pulley system, which in turn moves the drive belt, which in turn moves the tray, which moves along a trajectory specified by the guide shaft. Suitable motors include any mechanism for generating a force and/or torque, including but not limited to a stepper motor. The tension in the drive belt may be maintained using a tensioning spring attached to one end of the belt.

The transport module moves an input plate generally along an axis (e.g., an x-axis) from an I/O site to the transfer site and moves an output plate generally along the same axis but in the opposite direction from the transfer site to an I/O site. The input plate may be taken from the bottom of a stack of plates, and the output plate may be added to the bottom of the same or a different stack of plates, as described above.

4. Additional Features

The transport module may include additional features intended to enhance the convenience and/or functionality of the module, such as processing bins and barcode readers, among others.

The I/O sites in the transport module may accommodate a variety of commercially available plates (e.g., microplates) and are large enough so that the plates can be placed in the sites by a robot or a human hand. Moreover, as shown in FIG. 3, the I/O sites also may accommodate a variety of commercially available pre- and postprocessing plate bins (or magazines) for holding a stack of plates before and after analysis, respectively. A preprocessing bin may be removed from an I/O site and replaced with another preprocessing bin containing a new stack of plates with samples to be analyzed. Similarly, a postprocessing bin may be removed from an I/O site and replaced with another postprocessing bin to receive a new stack of plates with samples that have been analyzed. The plate bins can be used with other robotics (such as an appropriate combination of function modules) to dispense, wash, and read without restacking plates. Preferred plate bins typically accommodate zero to sixty plates.

The transport module also may include barcode readers for automatically identifying labeled plates. The barcode readers may be positioned on different sides of the transfer site, so that the readers can read barcodes mounted on different sides of a plate. The barcode readers also may be positioned to reduce specular reflection. The barcodes preferably are read as plates are being raised, typically following transport of the plate from an I/O site to the direct transporter access site. Barcode readers may be selected to read at 700 scans per second or higher and be programmed to decode a variety of symbologies, including SPC (EAN, JAN, UPC), Code 39 (3–43 digits), Codabar (3–43 digits), Standard 2 of 5 (3–43 digits), Interleaved 2 of 5 (4–43 digits), Code 93 (5digits), and MSI-Plessey (4–22 digits), among others. Information obtained from the barcode can be used for various purposes. For example, the barcode can be used to convey instructions to the analyzer relating to required changes in assay mode or optics configuration. The barcode also can be used to name a report file.

5. EXAMPLES

The following examples illustrate the potential variety of singulation strategies available in a transport module having the indicated number of I/O sites and a capability for top and/or bottom input and/or output:

One I/O Site. The transport module may take plates from the bottom or top of a stack of plates at a single I/O site and add plates to the bottom or top of the same stack. There are four possible singulation strategies:

| BI/BO | BI/TO | TI/BO | TI/TO |
|-------|-------|-------|-------|

Here, B denotes bottom, T denotes top, I denotes input, and O denotes output.

Two I/O Sites. The transport module may take plates from the bottom or top of a stack of plates in either I/O site and add plates to the bottom or top of the same stack in the same I/O site and/or another stack in the other I/O site. There are sixteen possible singulation strategies:

| BI1/BO1 | TI1/BO1 | BI2/BO1 | TI2/BO1 |
|---------|---------|---------|---------|
| BI1/TO1 | TI1/TO1 | BI2/TO1 | TI2/TO1 |
| BI1/BO2 | TI1/BO2 | BI2/BO2 | TI2/BO2 |
| BI1/TO2 | TI1/TO2 | BI2/TO2 | TI2/TO2 |

Here, 1 denotes site 1, 2 denotes site 2, and B, T, I, and O are defined as above. Significantly, if there are dedicated input and output sites, the transport module may (1) take plates from the bottom of the stack at the dedicated input site and add plates to the bottom of the stack at the dedicated output site, (2) take plates from the bottom of the stack at the dedicated input site and add plates to the top of the stack at the dedicated output site, (3) take plates from the top of the stack at the dedicated input site and add plates to the bottom of the stack at the dedicated output site, or (4) take plates from the top of the stack at the dedicated input site and add plates to the top of the stack at the dedicated output site.

Three or More I/O Sites. The transport module may take plates from the bottom or top of a stack of plates at any I/O site and add plates to the bottom or top of the same stack at the same I/O site and/or another stack at one of the other I/O sites. For a station with N I/O sites, there are generally $(2N)^2$ possible singulation strategies.

The singulation strategy used by a particular transport module may be fixed or varied from time to time or plate to plate. If there are two or more I/O sites, a given site may be used for input only, output only, or both input and output.

The I/O and function sites may be arranged to enhance convenience and/or efficiency, for both human users and the function modules. In transport module 2100, a first linear path connects the two I/O sites and the transfer site, and a second substantially perpendicular linear path connects the transfer site and the dispense and examination sites. However, the I/O and function sites also may be arranged in other ways. For example, the I/O, dispense, and examination sites all may be positioned along a single substantially linear path, which may be traversed in a single direction if plates are input at one end of the path and output at the other end of the path.

If there are separate input and output sites (or separate input and output ends at a single I/O site), a robot may deliver a plate to the input site and retrieve a (different) plate from the output site, both in the same trip. This feature is termed "process compression," because it reduces robot hand travel in servicing the transport module. In contrast, if there is only a single input/output site (with delivery and retrieval from the same side), the robot would have to remove any analyzed plates before delivering any unanalyzed plates. Thus, process compression replaces two separate robot movements with one robot movement.

C. Fluidics Module

The fluidics module generally comprises any mechanism or system for automatically dispensing fluid onto or into a sample holder. The mechanism may include reservoirs and dispense elements, and be capable of simultaneously and/or sequentially dispensing uniform and/or nonuniform fluid aliquots at one or more sample sites. The mechanism also may include a thermal regulator to control fluid temperature, thereby reducing bubble formation. Further aspects of the fluidics module are described in the following sections: (1) noncontact fluid dispensers, (2) contact fluid dispensers, (3) variable-pitch-array fluid dispensers, and (4) determination of inter-well separations.

1. Noncontact Dispensing

Fluid may be dispensed using "noncontact dispensing," which generally comprises any mechanism capable of dispensing fluid without contacting the fluid and/or sample container into which the fluid is dispensed. A simple example of a manual noncontact dispenser is an eyedropper, which can dispense drops of fluid without contacting a sample or receptacle. Further aspects of noncontact dispensing are described without limitation in the following examples:

a. Example 1

Positive-Displacement Syringe Pump with Sapphire-Tipped Nozzles

Figure 25:
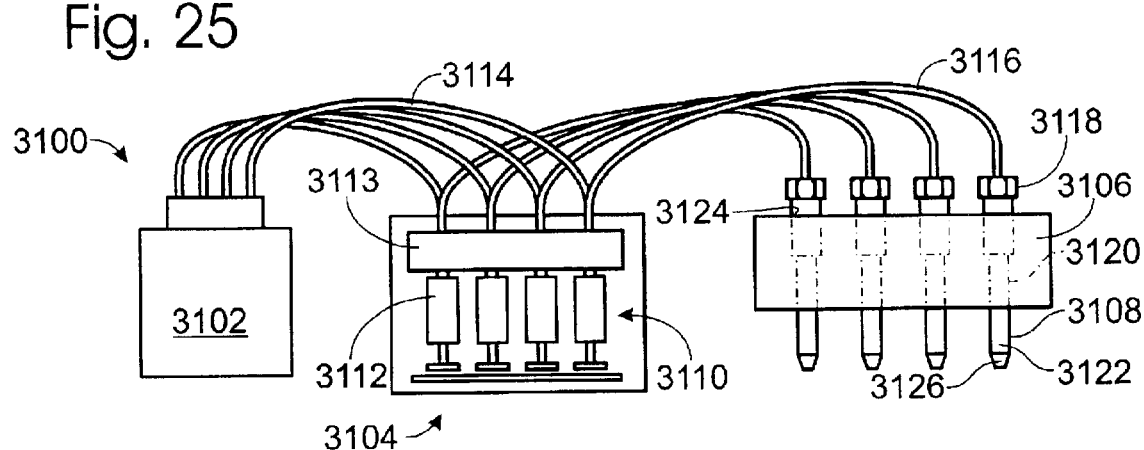
FIG. 25 is a partially schematic view of a noncontact fluid dispenser, showing a positive-displacement syringe pump with sapphire-tipped dispense elements.

FIG. 25 shows a noncontact fluid dispenser 3100 constructed in accordance with aspects of the invention. Fluid dispenser 3100 may include a fluid reservoir 3102, a pump 3104, and a dispense manifold 3106 having at least one dispense element 3108.

Fluid reservoir 3102 generally comprises any container configured to hold fluid for dispensing by dispenser 3100. Fluid reservoir 3102 may be formed of any nonreactive material, including glass and various plastics. Fluid reservoir 3102 may be configured so that it may be easily replenished with fluid and/or easily replaced with an alternative fluid reservoir.

Pump 3104 generally comprises any device or mechanism configured to move fluid between fluid reservoir 3102 and fluid manifold 3106, and to meter fluid accurately to dispense elements 3108. In FIG. 25, pump 3104 includes a (positive-displacement) microstepping syringe pump 3110 incorporating a plurality of syringes 3112 for dispensing fluid to a plurality of dispense elements 3108. The syringe pumps may operate independently using separate actuators, or the syringe pumps may be ganged together and driven using a single actuator. Using one or more aspirate/dispense valves 3113, syringe pump 3110 may aspirate fluid through aspirating tubes 3114 from fluid reservoir 3102, and dispense fluid through dispensing tubes 3116 toward dispense manifold 3106. Aspirating tubes 3114 and dispensing tubes 3116 may include any mechanism for transporting fluid between a fluid reservoir, pump, and dispense manifold, including but not limited to hollow plastic tubing.

Dispense manifold 3106 generally comprises any support configured to hold one or more dispense elements 3108. In FIG. 25, dispense manifold 3106 is a substantially elongate bar that holds a linear array of dispense elements, which may be used to dispense fluid into a linear array of sample holders, such as rows or columns in a microplate. Each dispense element can be driven by a separate pump, or two or more dispense elements can be coupled hydraulically using a manifold and driven by the same pump.

Dispense element 3108 generally comprises any element configured to dispense fluid to a surface, sample holder, or other repository, including surfaces and other fluids, without contacting such surface, sample holder, or other repository. In FIG. 25, dispense element 3108 includes (1) a receiving portion 3118 configured to receive fluid from dispensing tube 3116, (2) an anchor portion 3120 configured to connect the dispense element and dispense manifold 3106, and (3) a dispensing portion 3122 configured to dispense fluid received through dispensing tube 3116. Receiving portion 3118 generally includes a connector for connecting and securing together dispensing manifold 3106 and dispense element 3108. Anchor portion 3120 generally is joined to dispense manifold 3106 using some suitable mechanism, such as passing the anchor portion through an aperture 3124 in the dispense manifold. Anchor portion 3120 may be formed of various materials, including substantially rigid materials such as steel tubing to stabilize and reduce recoil of the dispense element during dispensing.

Dispensing portion 3122 generally includes an exit port such as a nozzle 3126 through which dispensed fluid may exit the dispense element. The exit port may include a small cross-section orifice and/or a small tapered tip and to increase the likelihood that dispensed fluid will exit the dispense element cleanly. The small cross-section orifice increases the exit velocity of the fluid, enhancing the likelihood that the fluid has sufficient kinetic energy to overcome surface tension and inertia effects at low fluid volumes to separate cleanly from the tip. Alternatively, or in addition, the positive-displacement pump may be used to provide sufficient acceleration and exit velocity to the fluid to overcome surface tension, based on dispense volume, fluid viscosity, and other factors. The small and/or tapered tip reduces the surface area capable of holding fluid, reducing the likelihood and potential size of pendant drops. In FIG. 25, dispensing portion 3122 includes a 200-micron-diameter sapphire orifice embedded in a dispense nozzle. The dispense strategy also may include a suck-back feature to control pendant drops and/or to increase predispense path length to allow a higher exit velocity to be attained.

In an exemplary embodiment, the dispense element (3108) includes FEP tubing (3116) slid over a piece of metal tubing (3122) that has a sapphire tip (3126) permanently embedded in an end. These elements are surrounded by a machined tube with a large head (3120), which further compresses the FEP tubing and acts as a locational element in the dispense manifold (3106), setting the correct height and concentric location of the dispense element (3108). A screw-on fitting (3118) presses on the large head of the machined tube, pushing the dispense element (3108) into the tapped bore of the dispense manifold (3106), securing the dispense element in place.

Fluid dispenser 3100 may be used to dispense fluid to one or more sample holders. Generally, a sample holder may be positioned beneath each dispense element, and pump 3104 may then be used to dispense a metered amount of fluid through each dispense element to each sample holder. Sample holders may be identified and sample holders and dispense elements may be aligned using any suitable mechanism. Each portion of this operation may be under computer control, including alignment of the dispense elements and sample holders, and operation of the pump, among others.

Fluid dispenser 3100 may be capable of dispensing fluids over a wide range of fluid volumes, and particularly in a preferred range between about 0.1 $\mu$L and about 100 $\mu$L. In assays, the coefficients of variation (CVs) for such dispenses preferably are about 2–10% or less for dispensed volumes down to about 0.1 $\mu$L. Fluid exit velocity may be optimized for the dispensed volume, for example, to reduce splashing as the fluid contacts the sample holder. The upper limit on dispense volume is essentially unconstrained, except by pump capacity.

b. Example 2

Figure 26:
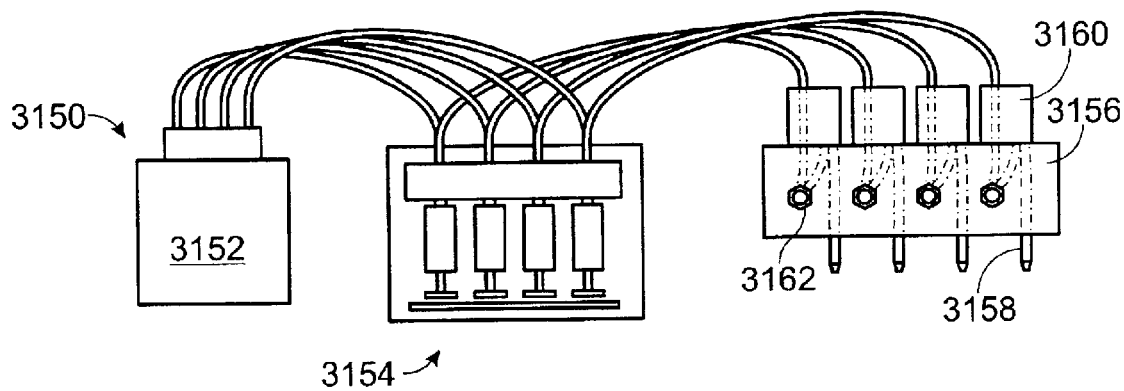
FIG. 26 is a partially schematic view of an alternative noncontact fluid dispenser, showing a positive-displacement syringe pump with solenoid valves and sapphire-tipped dispense elements.

Positive-Displacement Syringe Pump with Solenoid Valve and Sapphire-Tipped Nozzles FIG. 26 shows an alternative noncontact fluid dispenser 3150 constructed in accordance with aspects of the invention. Fluid dispenser 3150 generally includes a fluid reservoir 3152, a pump 3154, and a dispense manifold 3156 having at least one dispense element 3158. These components function essentially as described above for fluid reservoir 3102, pump 3104, dispense manifold 3106, and dispense element 3108, respectively.

Fluid dispenser 3150 also includes a pulse element 3160, which may be used to create a pressure wave as the pulse element is opened and closed to increase the energy of the fluid being dispensed. Pulse element 3160 preferably comprises a solenoid valve mounted near the dispense element, and coupled to the dispense element via an inlet fitting 3162. The pulse element may be pulsed or left open during the dispense. Each dispense element may be associated with its own pulse element, or groups of dispense elements may share a pulse element. Each pulse element may be under computer control.

c. Example 3

Positive-Pressure Pump with Solenoid Valve and Sapphire-Tipped Nozzles

Figure 27:
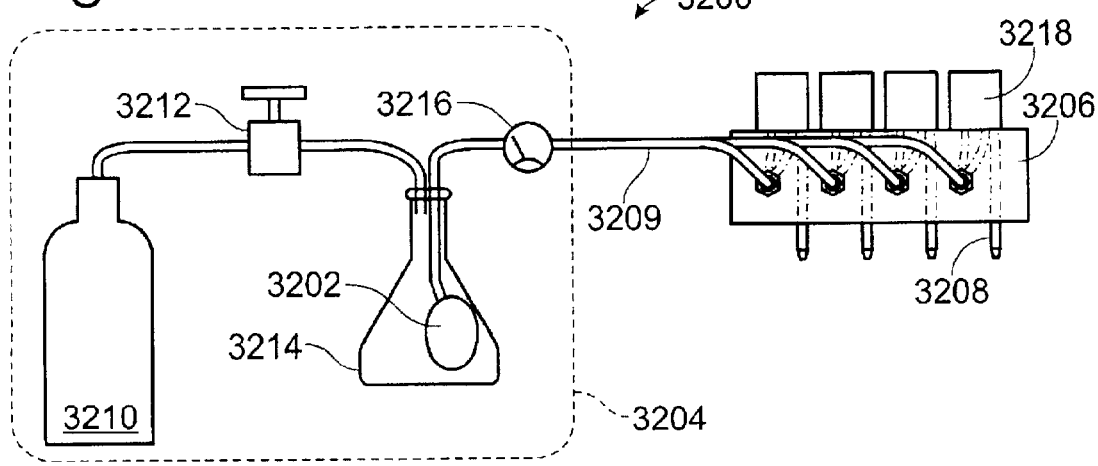
FIG. 27 is a partially schematic view of another alternative noncontact fluid dispenser, showing a positive-pressure pump with solenoid valves and sapphire-tipped dispense elements.

FIG. 27 shows another alternative noncontact fluid dispenser 3200 constructed in accordance with aspects of the invention. Fluid dispenser 3200 may include a pressure-responsive fluid reservoir 3202, a pressure pump 3204, and a dispense manifold 3206 having at least one dispense element 3208. Fluid may be dispensed from fluid reservoir 3202 to dispense elements 3208 using one or more dispense tubes 3209.

Pressure-sensitive fluid reservoir 3202 generally comprises any container configured to hold a fluid for dispensing, and to respond to an increase in pressure by dispensing a fluid. In FIG. 27, pressure-sensitive fluid reservoir 3202 comprises a fluid bladder, which responds to external pressure by decreasing in volume, concomitantly extruding or dispensing fluid.

Pressure pump 3204 generally comprises any device or mechanism configured to apply a variable but controllable positive pressure to pressure-sensitive fluid reservoir 3202. Pressure pump 3204 operates by compressing pressure-sensitive fluid reservoir 3202, forcing fluid from the reservoir through dispense tube(s) 3209 to dispense elements 3208. In FIG. 27, pressure pump 3204 includes a pressure source 3210, an upstream pressure controller 3212, a pressure vessel 3214, and a downstream pressure controller 3216. Pressure source 3210 may include any source of positive pressure, including a pump and/or a pressure tank, among others. Upstream pressure controller 3212 may include any mechanism for monitoring and/or regulating the pressure produced by the pressure source, and may be under manual or automatic control. Pressure vessel 3214 may include any container capable of enclosing pressure-sensitive fluid reservoir 3202 and maintaining a positive pressure on such reservoir. Downstream pressure controller 3216 may include any mechanism for monitoring and/or regulating the pressure of fluid in dispense tube(s) 3209.

Positive-pressure pumping preferably should be performed so that additional gases cannot go into solution in fluids being dispensed, because this could cause bubbles as the pressure is decreased during dispensing. Such additional gases may be avoided as shown above by using previously degassed fluids in a flexible bladder that is pressured externally in a pressure vessel.

Dispense manifold 3206 and dispense elements 3208 may take various forms, including forms described above for fluid dispensers 3100 and 3150. In FIG. 27, a single dispensing tube 3209 is used to supply fluid to the dispense elements 3208, and the dispense elements include pulse elements 3218, as described above. The pulse element is used to meter the fluid by timing the duration of the valve opening. This requires the fluid to have a controlled and calibrated flow rate. The pulse element also aids fluid dispensing, as described above, because the pressure wave aids fluid separation from the dispense element.

Alternative fluid dispensers may use alternative combinations of components. There may be a single pressure source for each dispense element, or there may be a common pressure source for sets of dispense elements. There may be a single pulse element for each dispense elements, or there may be a common pulse element for sets of dispense elements. The pressure drop in the fluid after the pulse element for each fluid path must be approximately the same for a common pulse element. Single pulse elements for each dispense element may have individually calibrated open times or duty cycles during the open time to account for differences in pressure drop.

d. Example 4

Figure 28:
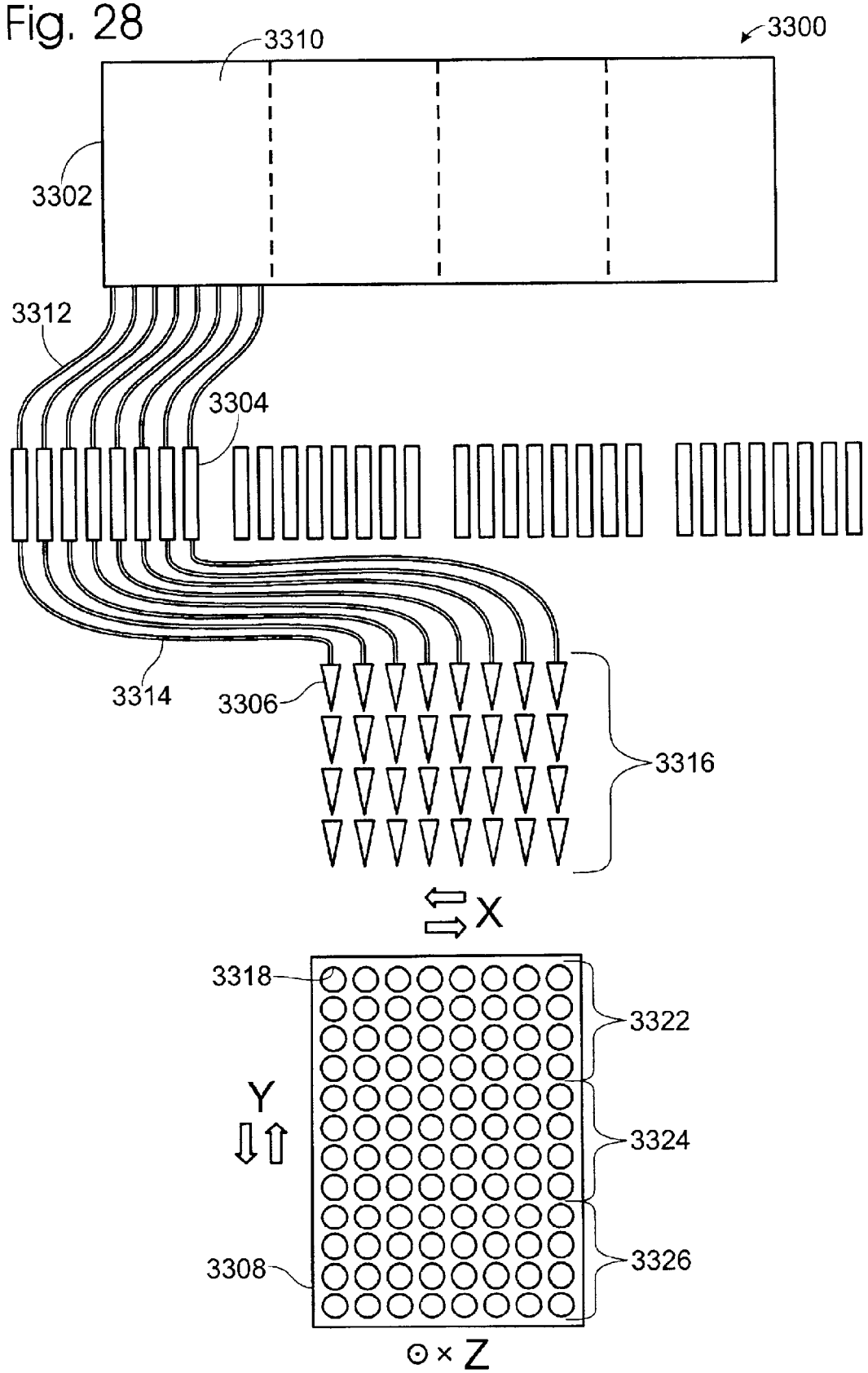
FIG. 28 is a schematic view of yet another alternative noncontact fluid dispenser, showing the relationship between fluid reservoirs, pumps, and dispense elements for the fluid dispenser shown (together with a transport module and an analysis module) in FIG. 2 as part of an integrated system for preparing and/or analyzing samples.

Positive-Displacement Syringe Pump with a Rectangular Array of PTFE Nozzles FIG. 28 shows yet another alternative noncontact fluid dispenser 3300 constructed in accordance with aspects of the invention. FIG. 28 is a schematic view of the fluid dispenser shown (together with a transport module and an analysis module) in FIG. 2 as part of an integrated system for preparing and/or analyzing samples. Fluid dispenser 3300 may include a fluid reservoir station 3302, at least one pump 3304, and at least one noncontact dispense elements 3306. These components may function essentially as described above in the context of FIGS. 25, 26, and/or 27. In use, the pumps direct fluid from the fluid reservoir station through the dispense elements and onto or into a sample holder such as a microplate 3308.

Fluid reservoir station 3302 may include bottles or fluid containers 3310 for holding buffers, reagents, samples, or other fluids for use in a particular assay. Fluid containers 3310 may vary in size, depending on fluid requirements for a particular procedure. For example, a large container may be used to dispense a buffer used in many sequentially performed assays. Alternatively, a small container may be used to dispense a tracer used in relatively small quantities and/or in a relatively small number of assays. Fluid reservoir station 3302 may be configured to facilitate easy interchange of different fluid containers for different purposes, for example, by using containers having a snap-on or screw-on connector. Fluid containers 3310 may be disposable or reusable and may be supplied independently or with a particular assay kit. The number of reservoirs that may be used simultaneously in station 3302 may range from 1 to N, where N is the number of dispense element assemblies that are connected to station 3302.

The dispenser effectively comprises an interchangeable conduit network that allows any combination of dispense elements (or tip devices) to be connected to any combination of fluid reservoirs. Dispenser 3300 may include one or more pumps 3304 such as syringe pumps and one or more dispense elements 3306. Generally, any pump may be connected to any fluid container, for example, via an aspiration tube 3312. Thus, multiple pumps may be connected to one or some fluid containers, and no pumps connected to other fluid containers. Alternatively, each pump may be connected to a different fluid container. Similarly, any pump may be connected to any dispense element, for example, via a dispense tube 3314. Thus, one pump may be connected to one or multiple dispense elements, and so on. In a preferred configuration, the dispenser includes 32 separate syringe pumps 3304 each connected one-on-one via separate dispense tubes 3314 to 32 separate dispense elements 3306.

The syringe pump may include various drivers. For example, the syringe pump may include a linear stepper motor or a linear servo motor. Alternatively, the syringe pump may include a rotary stepper motor or a rotary servo motor.

Dispense elements 3306 generally may be organized in any suitable arrangement, including linear and rectangular arrays. In most applications, it is preferable to match the organization of the dispense elements to the organization of all or part of the sample sites in the sample holder. Here, sample sites are preferred sample locations within the sample holder. Thus, a periodic (e.g., rectangular, hexagonal, etc.) arrangement of dispense elements is preferable for a sample holder such as a microplate or biochip having a periodic array of sample sites. In essence, the dispense elements are arranged to form an array of fluid dispensing channels that correspond to the sample sites. In a preferred configuration, the dispenser includes 32 dispense elements organized as a 4×8 regular array 3316, and more specifically as a 4×8 rectangular array with 9 mm separations to correspond to the 9 mm well separation in standard 96-well microplates, as described above.

Dispense-element array 3316 may be used to dispense individual measured aliquots of fluid onto or into a sample holder. For example, the array may be used to dispense into some or all of the wells 3318 in microplate 3308 by aligning the array with the wells and dispensing. If there are more sample wells than dispense elements, dispensing can occur in steps by dispensing to a first set of wells 3322, moving the dispense array and microplate relative to one another (for example, along a Y-axis), and then dispensing to a second set of wells 3324. This process may be repeated for additional sets of wells 3326 as necessary. This process is illustrated in FIG. 28, in which three sets of dispenses from a 4×8 array are used to dispense into a 96-well microplate.

A similar process may be used to dispense fluid into a microplate that has a higher density of wells, for example, 384-wells, or 1536-wells, among others. This can be accomplished by offsetting the dispense element array 3316 and/or microplate 3308 in the X direction and doing numerous passes in the Y direction. For example, two full passes in the Y direction with one adjustment in the X direction will allow dispensing in each well of a 384-well microplate. Similarly, four full passes in the Y direction with three adjustments in the X direction will allow dispensing in each well of a 1536-well microplate. The adjustment or offset should be by an integer multiple of the well-to-well spacing. Dispensing by column into 96, 384, 864, 1536, and 3456 well microplates can be accomplished using a linear array of 8 dispensing tips, since the number of rows is 8, 16, 24, 32, and 48, respectively. Dispensing by row into 96, 384, 864, 1536, and 3456-well microplates can be accomplished using a linear array of 12 dispensing tips since the number of columns is 12, 24, 36, 48, and 72 respectively. Any microplate with a number of columns or rows that is divisible by 8 can be dispensed into with this method. A rectangular array of dispensing tips may also be used with the center-to-center spacing of 9 mm in both directions, since the well-to-well spacing in all the above-mentioned plates is 9 mm or an integer fraction thereof (e.g., 4.5 mm, 2.25 mm, etc.).

Figure 29:
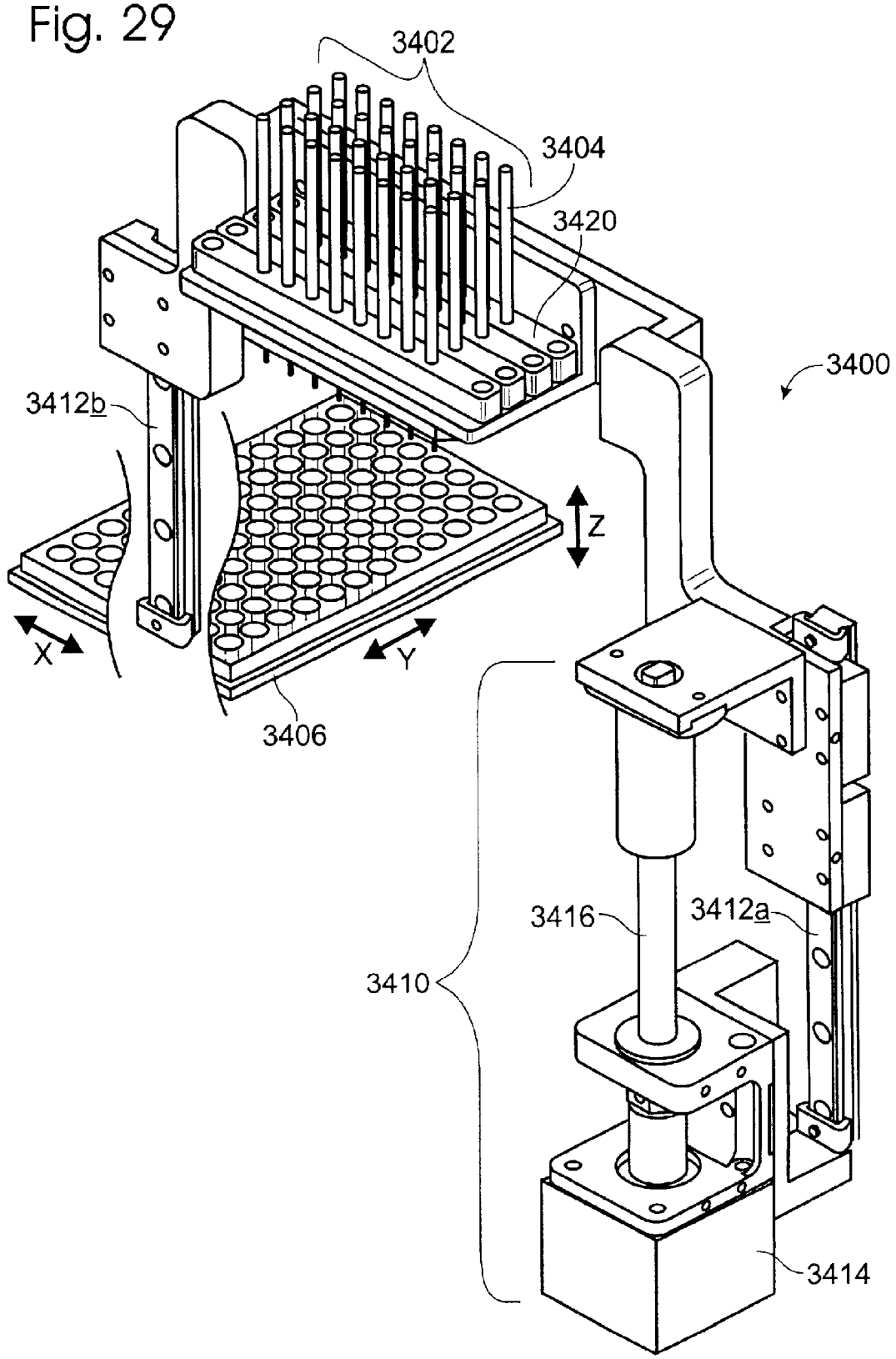
FIG. 29 is a perspective view of a dispense driver for the fluid dispenser of FIG. 28, showing the relationship between the dispense elements and a sample holder. The view is an enlargement of components shown in FIG. 18 in connection with a transport module.

FIG. 29 shows a portion of fluid dispenser 3300 including a dispense driver 3400 and an array 3402 of dispense elements 3404 positioned above a microplate 3406 at a dispense site. (The distance between the dispense driver and microplate has been exaggerated for clarity.) FIG. 29 is a partial view of fluid dispenser components shown in FIGS. 2, 3, and 18 relative to transport and/or analysis modules. The fluid dispenser generally may include (or associate) registration mechanisms for moving the dispense array and/or the microplate or other sample holder relative to one another along X, Y, and/or Z axes for dispensing. Such movement may be effected using any suitable combination (s) of drive mechanisms and any suitable drive strategy. In fluid dispenser 3300, the microplate is moved relative to the dispense array along the X and Y axes, and the dispense array is moved relative to the microplate along the Z-axis. More specifically, the microplate is moved using a transporter shared with an analysis module, as described below in connection with the analysis module, and the dispense array is moved using dispense driver 3400.

Dispense driver 3400 includes a linear actuator 3410 and parallel slides 3412a,b directed along the Z-axis on opposite sides of array 3402. The actuator moves the dispense array along the Z-axis guided by the parallel slides, so that the array may be raised and lowered relative to the microplate. Here, the linear actuator includes a stepper motor 3414 and an Acme screw 3416, although any mechanism capable of generating a linear displacement may be used, as described above in connection with the intrasite driver used in the fluidics module.

The array of dispense elements generally may be formed from one or more banks 3420 of dispense elements. In fluid dispenser 3300, these banks each include 8 dispense elements, which may be driven directly by a positive displacement pump or by a manifold. The banks may be positioned near one another with a spacing corresponding to the spacing between integer numbers of sample sites, for example, about 9 mm for standard microplates. This spacing may reduce spatial requirements while preserving an ability to dispense into the entire microplate. This spacing also may permit dispensing of multiple reagents with one scan of the sample holder under the dispenser array.

Each bank of dispensers can be independently installed or de-installed into a standard slot arrangement. With this slot arrangement, banks of dispense tips with different dispense characteristics (e.g., number of tips, volume range, or other functions such as plate washing) may be installed in a mix and match fashion. Software can be configured for the type of module that has been installed into each slot, and programmed accordingly. For example, microplate washing can be implemented by changing the design and programming of each bank of dispense elements. With proper design and sizing, one bank of dispense elements can aspirate solution from a column or row of wells, while another bank can subsequently dispense clean solution. Alternately, for the wash function, a head may contain both dispense and aspirate elements, at different heights, allowing dispense and aspirate without movement of the plate.

When each dispense element is connected to a separate pump, a software program can control the pumps while the plate is being scanned to allow random access dispensing of any reagent into any well. In parallel dispensing or transfer systems (e.g., pin transfer devices or arrays of conventional pipettes), random access is only possible if a source plate is first created with the desired reagent distribution or if the reagents somehow can be routed into the tops of the pipettes from separate sources. The dispenses from each dispense element may be performed simultaneously or sequentially, and be of uniform or nonuniform aliquots.

Figure 30:
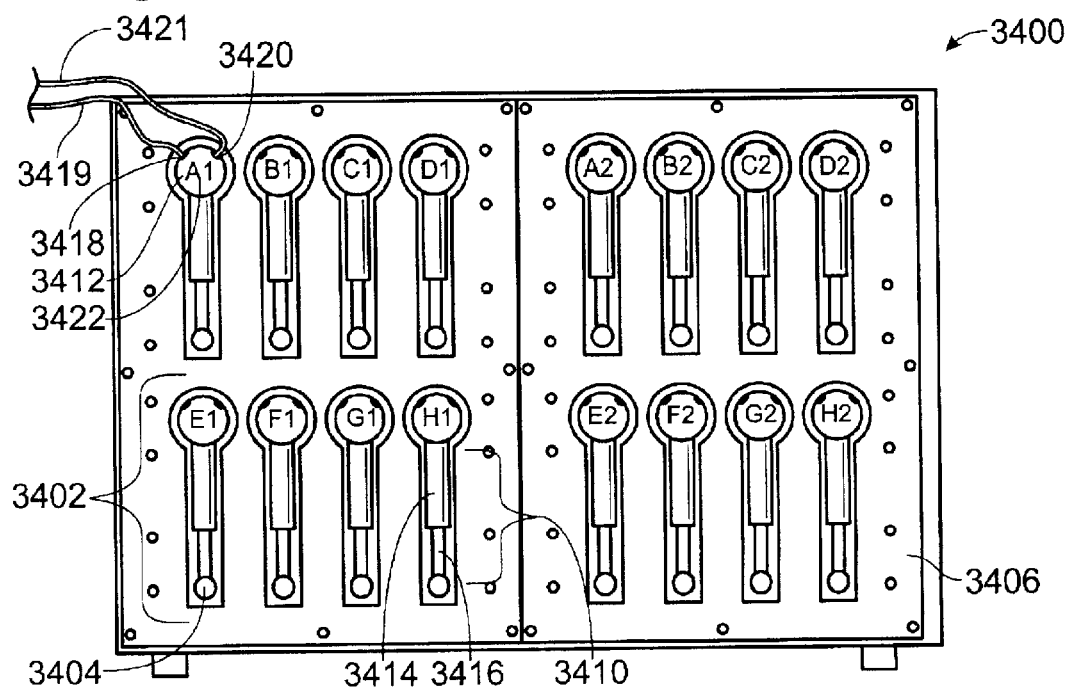
FIG. 30 is a front view of a portion of the fluid dispenser of FIG. 28, showing a fluid control unit including a bank of associated syringe pumps.

FIG. 30 shows a fluid control unit 3400 for use with the fluid dispenser of FIG. 28; alternative views/embodiments are shown in FIGS. 2 and 3 in relation to optionally associated transport and analysis modules. The fluid control unit generally comprises the pump or pumps and associated drivers used to direct fluid from a fluid reservoir station to one or more dispense elements. Fluid control unit 3400 includes a plurality of pumps 3402 (such as syringe pumps) and associated drivers 3404 mounted in a chassis 3406. The syringe pumps include a syringe 3410 and an inlet/outlet valve 3412. The syringe is used to aspirate and dispense fluid and includes a barrel 3414 for holding fluid and a plunger 3416 slidably received within the barrel and capable of generating a positive displacement. The plunger may be operatively connected to driver 3404. The valve is used for fluid input/output and includes an inlet 3418 for connecting to an aspiration or input tube 3419 coming from a fluid reservoir and an outlet 3420 for connecting to a dispense or output tube 3421 going to one or more dispense elements. Fluid reservoirs may be placed adjacent the fluid control unit to provide convenience in operation.

The valve or associated pump may include labels 3422 to assist hookup of input and output tubes. For example, valves and/or pumps associated with a control unit for a 4×8 array of dispense elements may be labeled A1-H1, A2-H2, A3-H3, and A4-H4, where the A-H are the standard designators for the 8 rows in a standard 96-well microplate, and the 1–4 refer to four columns. Moreover, valves, pumps, and/or input/output tubes, or portions thereof, may be color-coded, for example, using red, yellow, blue, and green to denote 1–4, as defined above. Generally, any marking or component capable of distinguishing valves, pumps, and/or tubes may functions as markings; however, preferred markings are number and/or letter codes and colors.

A preferred syringe pump is a CAVRO syringe pump. The starting speed of the CAVRO syringe pump is 1000 ½ steps/second, and the associated acceleration (slope) is 50,000 ½ steps/second$^2$. The pump executes 6000 ½ steps in its 30-mm travel, so that its starting speed is 5 mm/second, and its associated acceleration is 250 mm/second$^2$. If used with a 500-$\mu$L syringe, there are about 12½ steps per $\mu$L, so that the starting speed and top speed are not too different with the relatively small volumes (e.g., 0.5 $\mu$L) used here.

Figure 31:
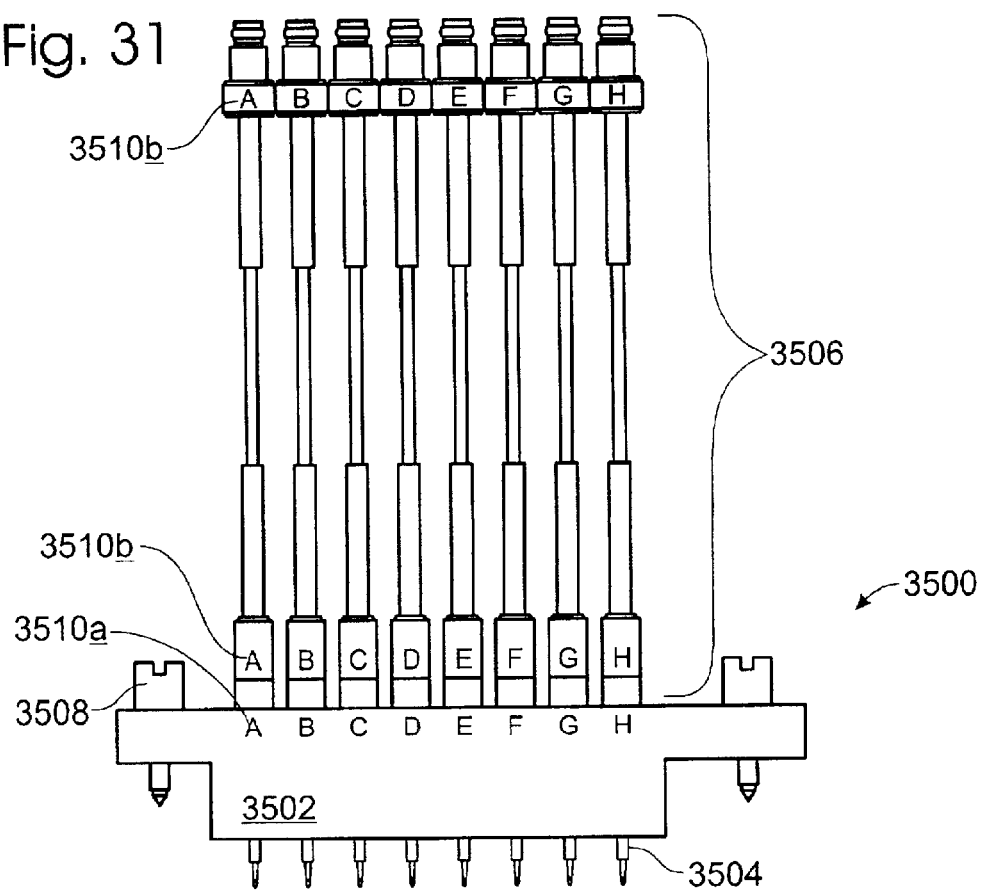
FIG. 31 is a front view of a bank of dispense elements for the fluid dispenser of FIG. 28.

FIG. 31 shows a bank of dispense elements 3500 for use with the fluid dispenser of FIG. 28. The bank includes a manifold 3502 and a plurality of substantially equally spaced dispense elements 3504 each attached to a tubing assembly 3506. The manifold supports the dispense elements and may be used to affix the bank to a dispense driver using suitable affixing means, such as fasteners 3508. The manifold may be formed of any suitable material, such as stainless steel, which is resistant to fluids and other materials that may come into contact with the manifold. The manifold may be asymmetric to ensure that it is mounted properly at a dispense site. The tubing assembly is used to connect the dispense elements to the fluid reservoir(s). The manifold and/or tubing assemblies may include labels 3510a,b,c to assist hookup between the manifold and assemblies.

Figure 32:
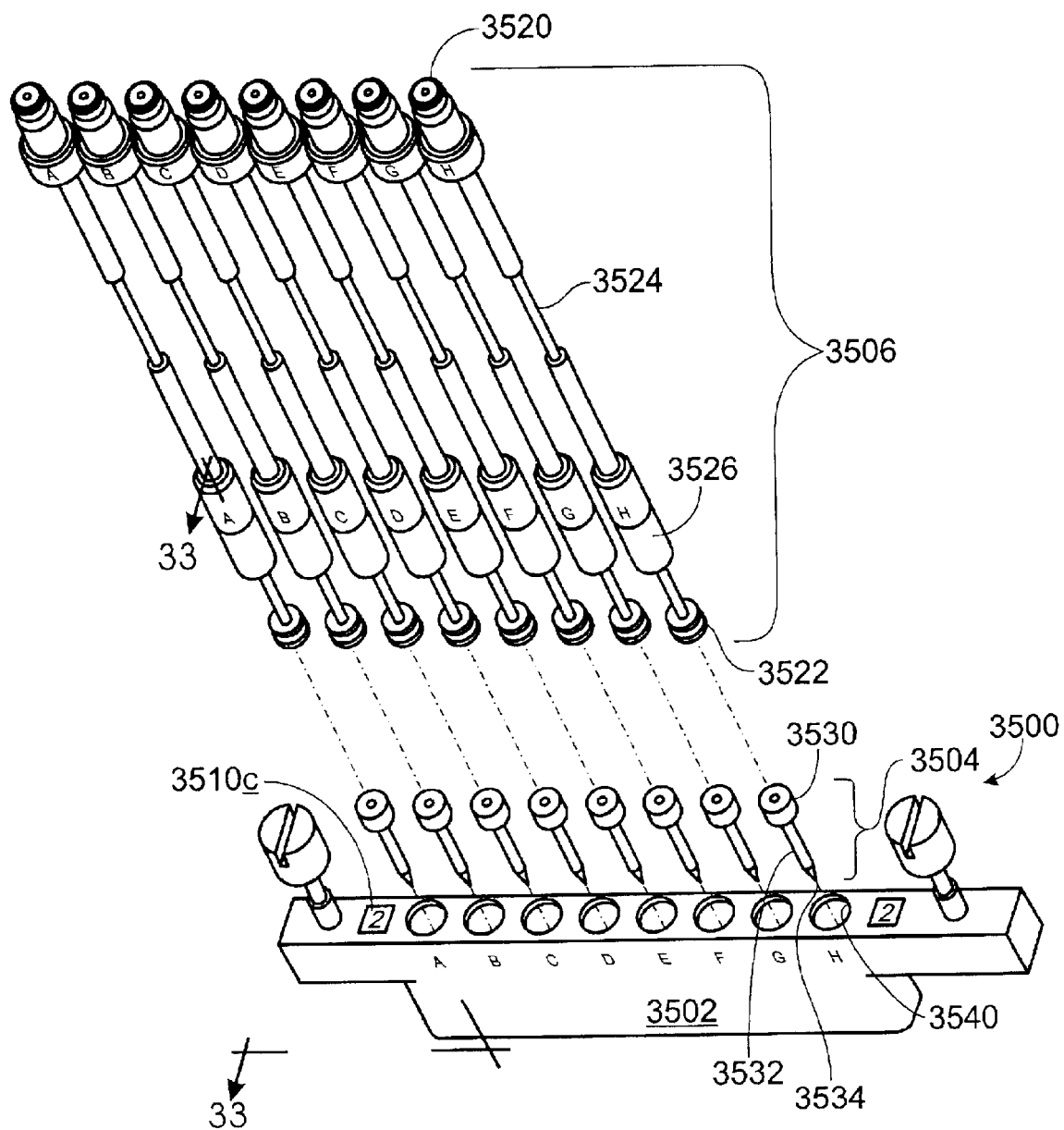
FIG. 32 is an exploded perspective view of the bank of dispense elements shown in FIG. 31.
Figure 33:
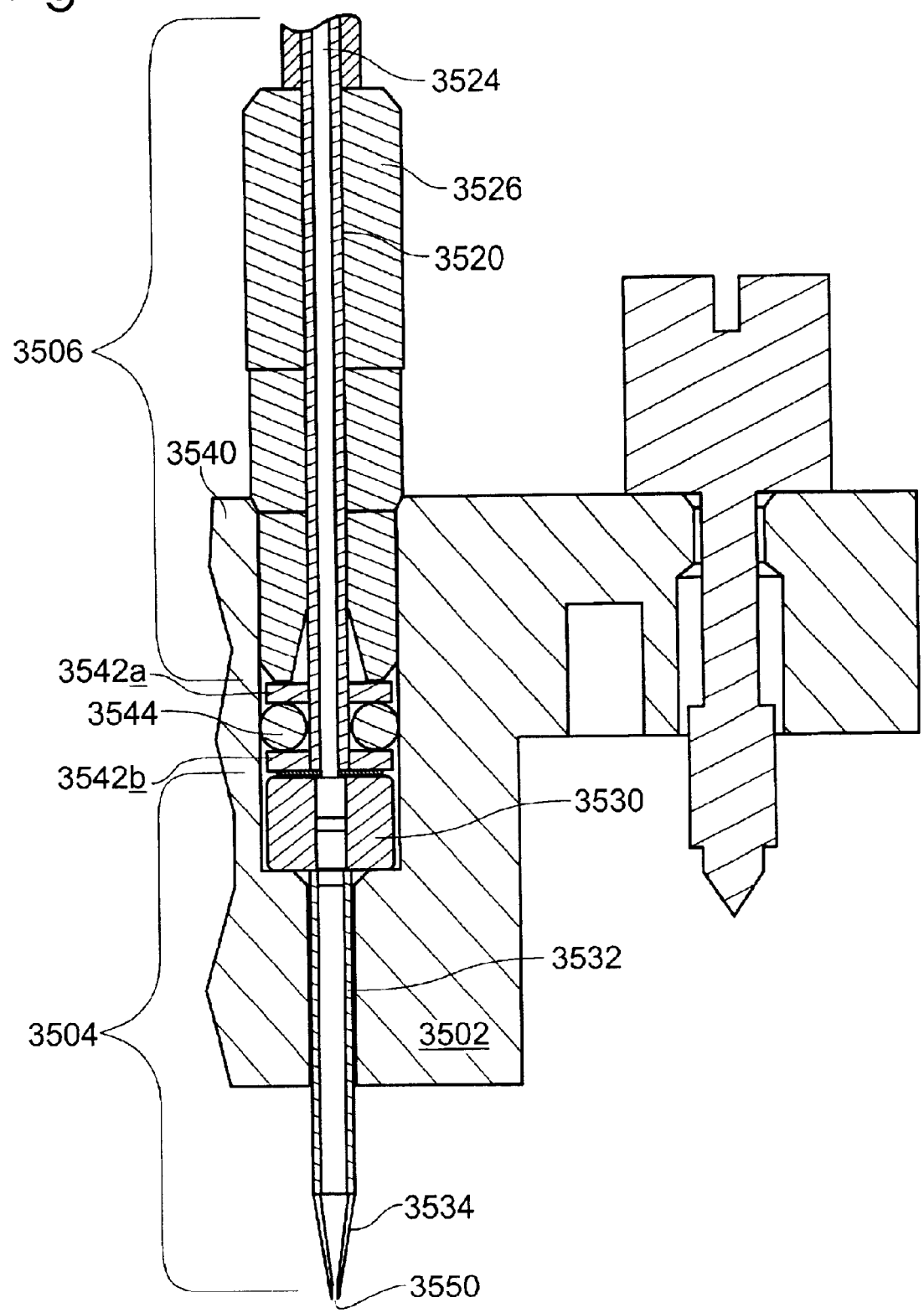
FIG. 33 is a cross-sectional view of a portion of the bank of dispense elements shown in FIG. 32, taken generally along line 33—33 in FIG. 32.

FIGS. 32 and 33 show alternative views of bank 3500 and associated tubing assemblies 3506. The tubing assembly may include an input (distal) flange 3520 for connecting to a pump (e.g., in a fluid control unit), an output (proximal) flange 3522 for connecting to a dispense element, and a section of tubing 3524 for spanning the gap between the pump and the dispense element. The input and output flanges generally comprise any suitable mechanism for ending the tubing so that it may be joined to another structure. For example, the flanges may include ¼-28 fittings. The tubing generally may have any suitable dimensions. For example, the tube may be about 40 inches long to accommodate positioning of the pumps relative to the dispense array, with an inner diameter of about 30/1000 of an inch and an outer diameter of about 62/1000 (1/16) of an inch. The tubing further may include reinforcements such as a spiral wrap strain relief 3526 positioned adjacent the output flange. A preferred tube material is FEP. The dispense element may include a head (or tip flange) 3530, a body tube 3532, and a dispense tip 3534. The tubing assembly and an associated dispense element may be operatively joined by inserting both into an appropriately sized aperture 3540 in manifold 3502, separated by washers 3542a,b and an intervening O-ring 3544.

The fluid enters the dispense element at the interface of the tip flange and supply tubing flange. This flanged interface may reduce fluid holdup and dead volume areas, important when changing fluids or cleaning the tip, and may allow for either the tip or supply tubing to be changed independently. The tip flange may be formed via a machined PEEK plastic section of the tip. The tubing flange may be formed conventionally. This machined flange is press-fit onto a stainless steel tube. The entire inner surface of the PEEK flange and stainless steel tube is lined with thin-wall PTFE heat-shrink tubing, terminating at the PEEK flange at one end and the dispense nozzle 3550 at the other (dispense) end. The dispense end is formed from the heat-shrink tubing into a cone-shaped nozzle protruding from the stainless steel tubing. The thin wall of the heat-shrink tubing and its ability to shrink onto a mandrel are important features of the dispense element. The cone-shaped nozzle may be formed manually. This process should be performed carefully and reproducibly, since a burr on the dispense end, an unsquare cut of the dispense end, or a slightly misshaped nozzle all may affect dispensing performance. Alternatively, the dispense element may include a conventionally injected molded tip made of polypropylene with substantially similar geometry. The wall thickness and aperture opening would be of similar size, and care would have to be taken to ensure that no flash from the molding process affected dispensing performance.

The noncontact flanged dispense tip described here shares many features with the sapphire dispense tip described above, including a small, controlled, inner-diameter bore and a small-to-minimum surface area at the dispense end of the tip. The inner diameter of the orifice of the noncontact flanged dispense tip is about 190±10 microns, and the inner diameter of the orifice in the sapphire tip is about 200 microns. The circumferential wall of the tip around the dispense orifice is about 5-thousandths of an inch thick. The small bore increases the exit velocity of the fluid, and the minimum surface area decreases surface tension, both of which are important for cleanly ejecting small (~0.5 $\mu$L) drops of fluid. The noncontact flanged dispense tip also provides a completely nonmetallic flow path because the interior of the flow path is PTFE Teflon. This greatly reduces the formation of pendant drops due to the surface properties of the Teflon, which is an improvement over the design of the sapphire tip. Generally, any material (such as a hydrophobic material) that reduces the affinity of the dispensed fluid for the dispense element may be used within the fluid path and/or at the dispense tip to reduce pendant drops. Such materials include polypropylene, polyethylene, and FEP.

The system described above may be used to dispense fluid volumes down to 0.25 $\mu$L or less. Small (submicron) volumes generally may be dispensed by decreasing the thickness of the wall of the tip, especially to or below about 8-thousandths of an inch, and even to or below about 2.5-thousandths of an inch. Generally, a wall thickness of about 10-thousandths of an inch does not work well for dispensed volumes of less than about 1 $\mu$L. Smaller dispensed volumes also may be obtained by using a syringe pump with a linear motor, which may also increase the rate of fluid dispensing by providing a more rapid acceleration and thus a higher exit velocity.

In summary, the noncontact dispenser may include a fluid source, a pump, and a noncontact dispenser, where a conduit path extends from the pump to the orifice of the dispenser. The conduit path may remain open and unconstricted between successive depositions because fluid is retained in the conduit path by surface tension and/or capillary action until expelled by the positive displacement pump. Thus, the dispenser may dispense fluid without closing or constricting the conduit channel, or contacting droplets of the dispensed fluid to a surface. Moreover, the rate of deposition will generally correspond to or equal the incremental rate of pumping. The dispenser may be used to deposit fluid aliquots as small as 5 µL or less.

2. Contact Dispensing

Fluid also may be dispensed by "contact dispensing," which generally comprises any mechanism for dispensing fluid in which the dispenser contacts the sample and/or sample container into which the fluid is dispensed. An example of a contact dispenser is a pin transfer device, which uses a pin to pick up small quantities of fluid from a storage area and transfer the fluid to a receptacle. Pin transfer devices are described below in the context of microplates, although they also may be used for transfer to and/or from other sample containers. Further aspects of contact dispensing are described without limitation in the following examples:

a. Example 1

Figure 34:
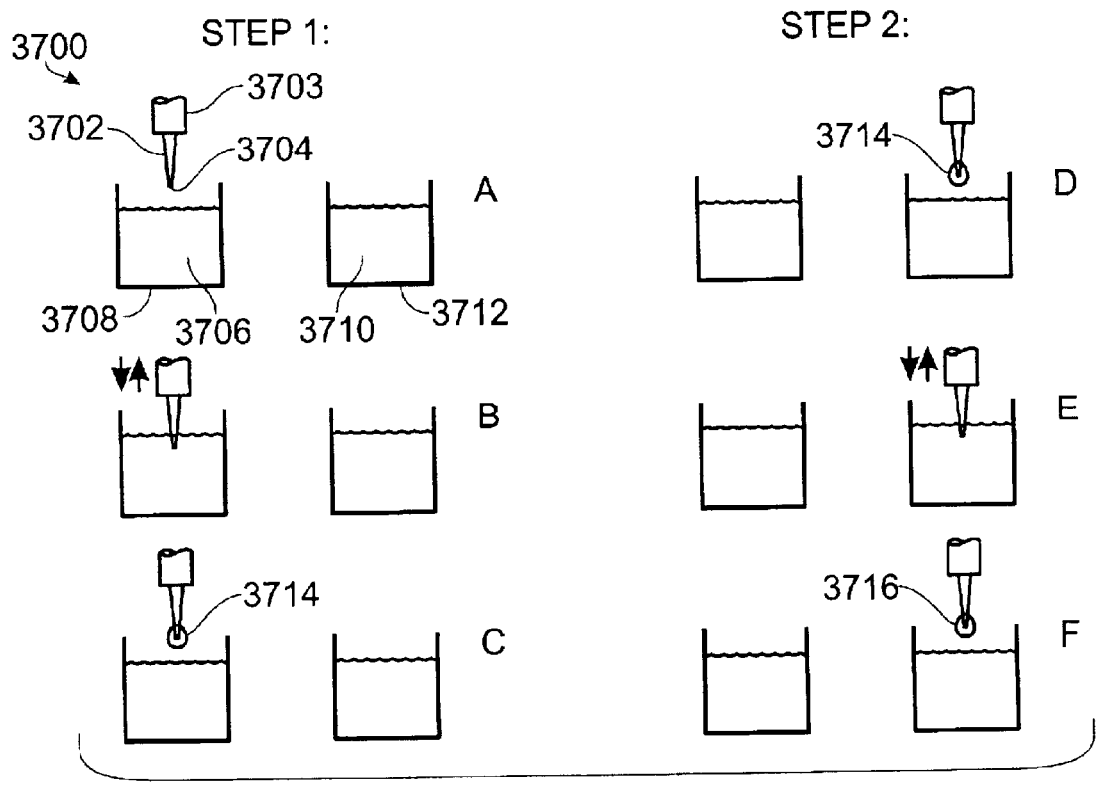
FIG. 34 is a six-panel, time-lapse schematic view of a single pin from a pin transfer device, showing how the device may be used to transfer fluid.

FIG. 34 shows a pin transfer device 3700. Pin transfer device 3700 includes a pin 3702 and a mount 3703 configured to support the pin so that a tip 3704 of the pin is presented for fluid transfer. Pin transfer device 3700 may be used to transfer a small amount of a first liquid 3706 from a storage area 3708 to a second liquid 3710 in a receptacle 3712. This transfer may proceed in two steps:

Step 1. For loading, pin transfer device 3700 is positioned over storage area 3708 (Panel A), lowered until tip 3704 contacts first liquid 3706 (Panel B), and then raised until tip 3704 breaks contact with first liquid 3706 (Panel C). In the process, a drop 3714 of first liquid 3706 remains in contact with tip 3704 due to surface tension.

Step 2. For dispensing, pin transfer device 3700 is positioned over receptacle 3712 (Panel D), lowered until tip 3704 and drop 3714 contact second liquid 3710 (Panel E), and then raised until tip 3704 breaks contact with second liquid 3710 (Panel F). In the process, drop 3714 will be transferred to second liquid 3710. (A new drop 3716 representing a mix of second liquid 3710 and drop 3714 may remain in contact with tip 3704 after the transfer.).

The volume of drop 3714 will depend on various factors, including (1) the surface tension and viscosity of first liquid 3706, (2) the material, geometry, and cleanliness of tip 3704, and (3) the kinetics of transfer. However, for a fixed set of parameters (e.g., fluid, tip, etc.), the volume should be relatively precise and reproducible, permitting volumetric fluid transfer.

b. Example 2

Figure 35:
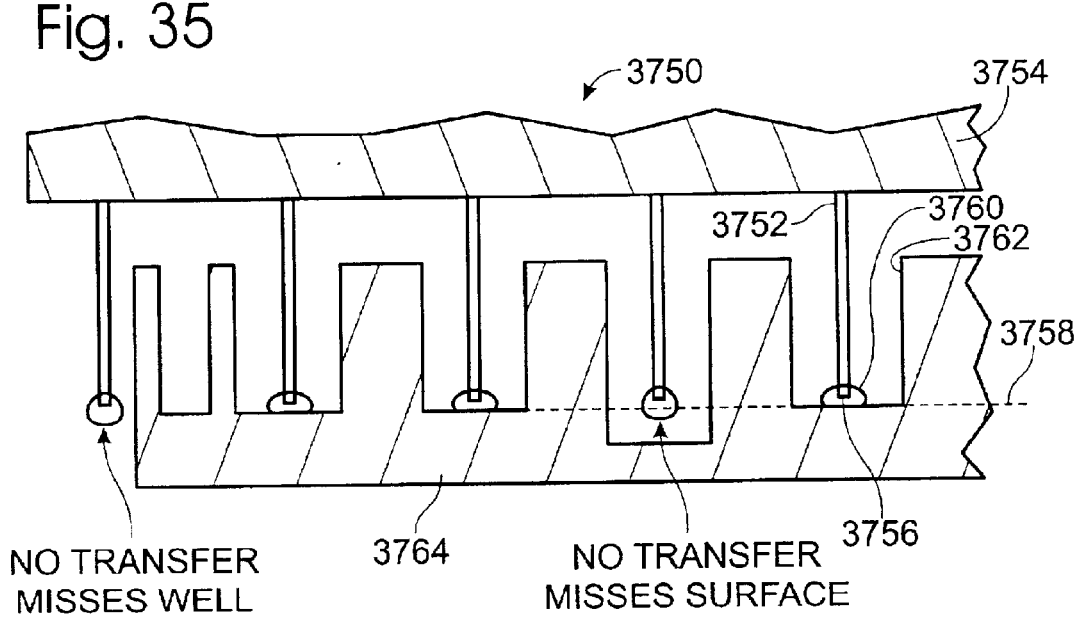
FIG. 35 is a schematic view of a pin transfer device and associated sample holder, showing shortcomings associated with a rigid array of pins.

FIG. 35 shows an alternative pin transfer device 3750. Pin transfer device 3750 includes a plurality of pins 3752 and a rigid mount 3754 configured to support the pins in a preselected array. The tips 3756 of pins 3752 lie approximately within a plane 3758. Pin transfer device 3750 is configured to transfer a drop of fluid 3760 simultaneously between arrays of storage areas and/or receptacles, such as wells 3762 in a microplate 3764. More specifically, the device is configured to transfer fluid substantially simultaneously between storage areas and receptacles by substantially simultaneously contacting the pins to the storage area(s) to load the fluid, and then substantially simultaneously contacting the loaded pins to the receptacle(s) to unload the fluid.

Unfortunately, pin transfer devices using a rigid array of pins may suffer from a number of shortcomings. For example, there may be variations in the dispensed volume if the receptacles do not lie in a single plane, because the tips of some of the pins may not be able to contact the associated receptacle. There also may be variations in the dispensed volume if the receptacles are unevenly spaced perpendicular to the plane of the tips, because some of the pins may miss the associated receptacle. These shortcomings may be particularly acute for transfer to and/or from microplates, because microplates may vary in their dimensions due to shrinkage or expansion during or after molding and because microplate wells may have uneven bottom surfaces.

c. Example 3

Figure 36:
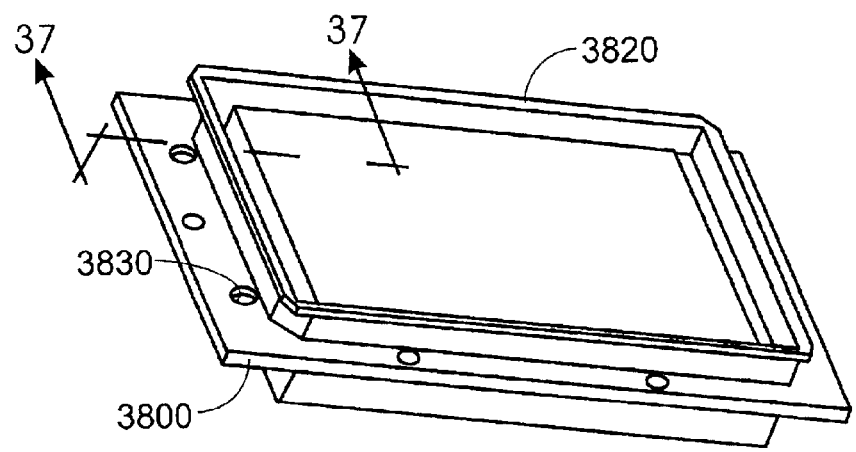
FIG. 36 is a perspective view of an alternative pin transfer device and associated sample holder.
Figure 37:
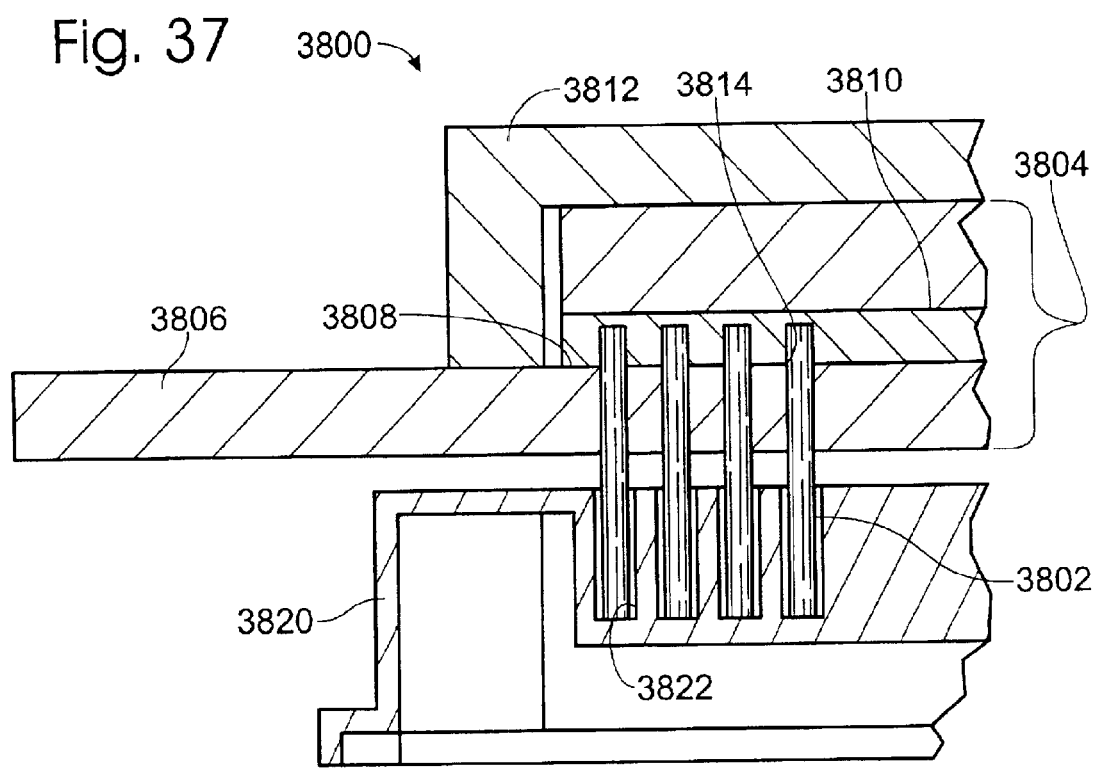
FIG. 37 is a cross-sectional view of the alternative pin transfer device and associated sample holder of FIG. 36, taken generally along line 37—37 in FIG. 36.

FIGS. 36 and 37 show another alternative pin transfer device 3800 configured to transfer fluid simultaneously between arrays of storage areas and/or receptacles. Pin transfer device 3800 includes a plurality of pins 3802 and a flexible mount 3804 configured to support the pins securely but movably in a preselected array. The flexible mount may allow the pins to move vertically and/or horizontally relative to their equilibrium positions. In pin transfer device 3800, flexible mount 3804 includes a rigid block 3806, a film 3808 abutting the rigid block, a flexible (or elastomeric) sheet 3810 abutting the film, and a holder 3812 abutting and at least partially holding the block, film, and sheet. Pins 3802 are embedded in flexible sheet 3810 and slidably positioned through apertures 3814 in film 3808 and rigid block 3806. Portions of the pins configured to contact the flexible sheet may be etched to facilitate adhesion with the sheet. Rigid block 3806 provides structural rigidity that maintains the orientation and relative positions of the pins. Film 3808 separates rigid block 3806 and flexible sheet 3810, permitting the flexible sheet to move independently of the rigid block. Flexible sheet 3810 provides a force that biases pins 3802 toward rigid block 3806. Flexible sheet 3810 may include one or more layers, providing a flexible and chemical-resistant surface and the desired compliance and mechanical stability. Film 3808 and/or flexible sheet 3810 may provide a barrier to fluid flow through the device. Pin transfer device 3800 may be used to transfer fluid to a microplate 3820 having a plurality of wells 3822.

A flexible mounting mechanism may overcome shortcomings associated with rigid mounts. For example, a flexible mechanism may allow pins to move rather than bend or break if accidentally brought into contact with a surface such as a shallow well bottom during fluid transfer. A flexible mechanism also may be used to compensate for variations in sample-holder dimensions, such as variations due to shrinkage and/or expansion relative to the "nominal" dimensions. For example, the flexible sheet may be mounted in a frame whose outer dimensions can be adjusted to be slightly larger or slightly smaller than the nominal dimensions, for example, by placing the sheet under stress. The pin-to-pin spacing can then be reduced to match a smaller sample holder by decreasing the stress on the sheet (e.g., by adjusting the outer frame), and increased to match a larger sample holder by increasing the stress on the sheet.

The flexible mounting mechanism in pin transfer device 3800 may overcome shortcomings associated with other flexible mounts, such as flexible mounts that simply permit pins to float in their mounts. For example, the flexible sheet may inhibit the accumulation of solids on the pins near the anchor points of the pins, reducing friction between the pins and their fixtures. Such friction may prevent the pins from moving freely or at all, so that some pins may not be able to touch the desired surface and transfer fluid uniformly. The sheet also may facilitate cleaning, because the ends of the pins are sealed in the sheet, reducing contamination by cleaning materials. Typically, the device is cleaned by immersing and/or scrubbing portions of the device that contact fluid, such as the tips of the pins, with a cleaning fluid.

Pin transfer device 3800 generally may be formed or constructed using any suitable technique, including the following five-step process. First, pins 3802 may be positioned in a rack. Second, pins 3802 may be positioned through rigid block 3806 and film 3808. Third, flexible sheet 3810 may be poured to encapsulate the pins, and allowed to dry. Fourth, holder 3812 may be mounted to the sandwich formed by the rigid block, film, and flexible sheet. Finally, the finished device may be removed from the rack.

Pin transfer device 3800 also generally may be formed of any materials having the desired mechanical properties. For example, the flexible sheet may be formed of any suitable flexible material, and the pins may be formed of any suitable wetable material that facilitates the loading and unloading of reproducible volumes of fluids. Preferred materials include a silicone RTV sheet and a closed cell polyurethane foam for the mount and stainless steel for the pin.

The pin transfer device may be used manually and/or automatically. For example, pin transfer device 3800 includes apertures 3830 for mounting the device to a driver for raising and lowering the device relative to a sample, and/or for moving the device between different samples.

The pin transfer device also may be used in conjunction with any suitable sample holder, including microplates. If used with a microplate, the pin transfer device may include linear or rectangular arrays of pins corresponding to some or all of the rows or columns in a microplate having 96, 384, 864, 1536, 3872, 9600, or another number of wells. In turn, the microplate or other sample holder may be constructed to transfer information regarding the form of the microplate to the pin transfer device. Such information may include the dimensions of the sample holder and the number and dimensions of any associated sample wells. Such information may be encoded using a bar code, a reference fiducial, and/or other features of the sample holder.

3. Variable Pitch Array Fluid Dispenser

The separations between dispense elements in a fluid dispenser may be fixed to correspond to nominal separations between sample sites in standard sample holders, or integer multiples thereof, as described above. However, if the separations between sample sites in actual sample holders differ significantly from the nominal separations in the standard sample holders, these fluid dispensers may dispense fluid onto the side or outside of the intended sample sites in the sample holder. Such misdirected dispenses may be especially likely with microplate sample holders, because microplate dimensions often vary due to shrinkage and/or expansion during or after molding. To overcome these difficulties, the fluid dispenser may include mechanisms for actually and/or effectively adjusting the separation between dispense elements to match the separation between sample sites in a given sample holder.

Figure 38:
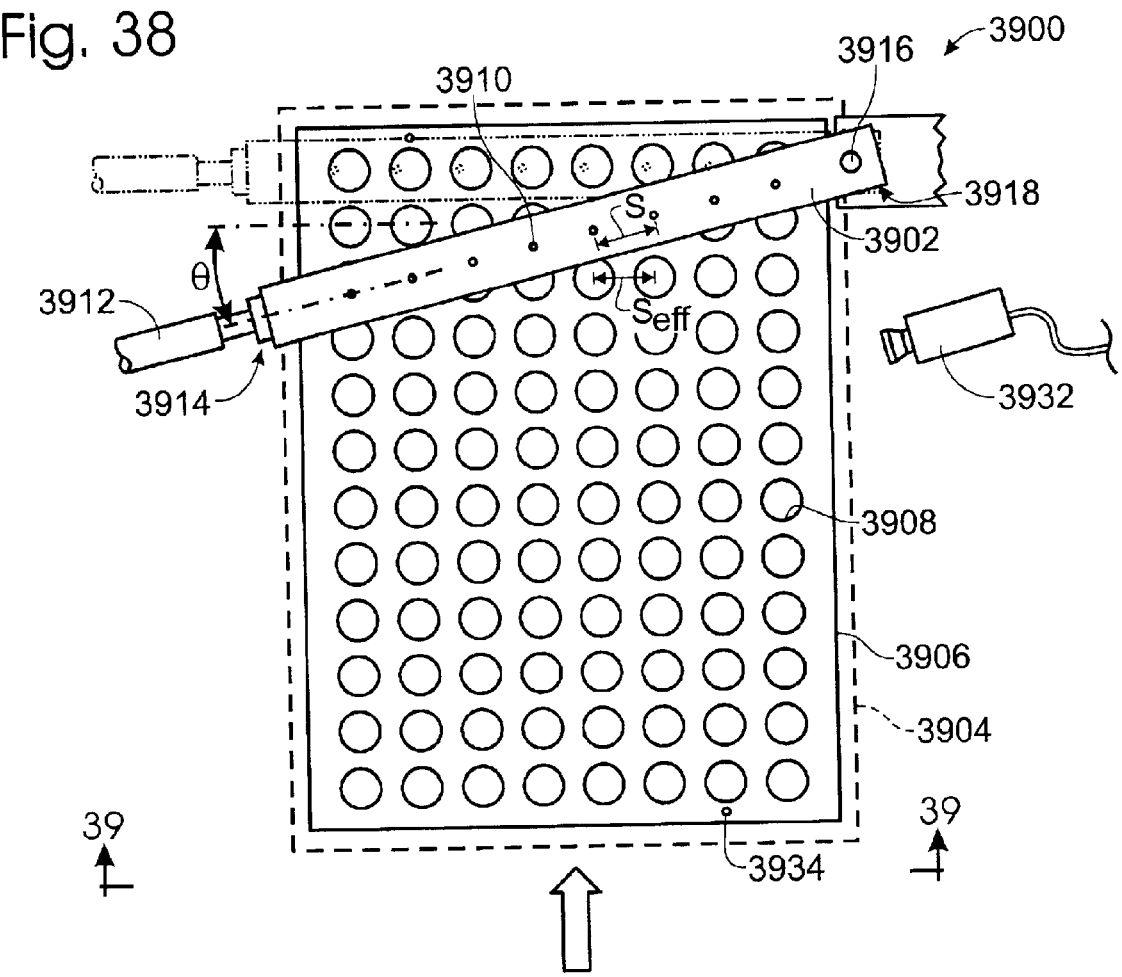
FIG. 38 is a partially schematic top view of a variable-pitch-array fluid dispenser, showing the dispenser in use with a microplate.
Figure 39:
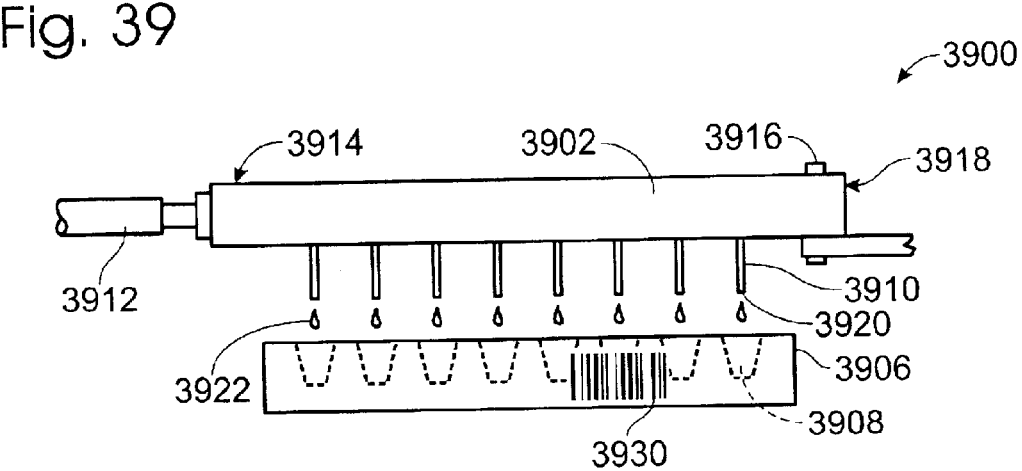
FIG. 39 is a partially schematic side view of the variable-pitch-array fluid dispenser and microplate of FIG. 38, taken generally along line 39—39 in FIG. 38.

FIGS. 38 and 39 show a variable-pitch-array fluid dispenser 3900 that may be used effectively to adjust the separation between dispense elements. Fluid dispenser 3900 includes a dispense manifold 3902 and a dispense site 3904 configured to receive a sample holder 3906 having a plurality of sample wells 3908.

Dispense manifold 3902 may take various forms. For example, dispense manifold 3902 includes a substantially linear array of dispense elements 3910. The manifold includes a fluid inlet 3912 positioned adjacent a first end 3914 of the array and a pivot 3916 positioned adjacent a second end 3918 of the array. Fluid inlet 3912 is operatively connected to dispense elements 3910, so that fluid may enter dispense manifold 3902 through fluid inlet 3912 and exit dispense manifold 3902 through dispense tips 3920 of dispense elements 3904. Fluid 3922 may be dispensed through dispense tips 3920 using a variety of mechanisms, including noncontact mechanisms, as described above. The fluid may exit the dispense tip in various forms, including drops, trains, and streams, among others, depending on exit velocity, dispense duration, orifice diameter, and so on.

Dispense manifold 3902 is rotatable about pivot 3916, so that the effective separation between dispense elements 3910 can be adjusted to match the actual separation between sample wells 3908 in sample holder 3906. Specifically, dispense manifold 3902 may be rotated relative to a sample holder, so that the array of dispense elements is oriented at an angle θ relative to the array of sample wells. Rotation of the array of dispense elements relative to the sample holder effectively decreases the separations between dispense elements relative to the sample holder. Mathematically, the effective separation between linearly arrayed dispense elements is described by the following equation:

$$S_{eff} = S \cdot \cos \theta \qquad (1)$$

Here, $S_{eff}$ is the effective separation between dispense elements, S is the actual separation between dispense elements, and θ is the angle between the array of dispense elements and the array of sample wells. Generally, the actual separation between dispense elements in the dispense manifold should equal or exceed the maximum separation between sample wells in expected sample holders, because relative rotation of the dispense manifold and sample wells can only decrease the effective separation between the dispense elements.

Rotation of the dispense manifold about the pivot generally may be controlled automatically by the dispenser or manually by an operator. If the pivot is controlled automatically, a driver may be connected to the pivot or to the dispense manifold, depending on whether the dispense manifold is attached fixedly or rotatably to the pivot, respectively.

Fluid is dispensed into a sample holder by adjusting the relative positions of the dispense elements and sample holder so that $S_{eff}$ is substantially equal to the actual separation between sample sites, and then by moving the sample holder relative to the dispense site while simultaneously or sequentially dispensing fluid from the dispense tips of the dispense elements. Fluid may be dispensed simultaneously if the angle of rotation θ is small, so that each dispense element is positioned over a sample well simultaneously. Fluid may be dispensed sequentially if the angle of rotation θ is large, so that only some dispense elements are positioned over a sample well at a given time. In the latter case, fluid dispensing must be coordinated with the relative motion of the sample holder. If the sample holder includes multiple rows of sample wells, fluid may be dispensed sequentially into each row through cycles of motion and dispensing, the cycles of relative motion bringing subsequent rows of sample wells into alignment with the dispense manifold. Generally, the sample holder may be moved, the dispense manifold may be moved, or both may be moved for fluid dispensing.

The relative positions of the sample holder and dispense site may be altered using any suitable mechanism. For example, the dispense manifold may be rotated and/or translated relative to the sample holder, the sample holder may be rotated and/or translated relative to the dispense manifold, or the sample holder and dispense manifold may be rotated and/or translated relative to one another. Similarly, the dispense manifold and/or the sample holder may be rotated about a variety of positions, so that the pivot may be located at various positions within the dispense manifold and/or dispense site.

Alternative mechanisms also may be used to adjust the separation between dispense elements in a fluid dispenser to correspond to the separation of sample wells in a sample holder. In one alternative, the separation between each pair of dispense elements may be adjusted to correct for deviations in positions of sample wells along a first axis, and the relative distance moved by the fluid dispenser and sample holder may be adjusted to correct for deviations in positions of sample wells along a second axis. In another alternative, if each dispense element can be individually controlled, a linear array of dispense elements and sample wells may be moved parallel to one another, coordinating the dispensing of fluid with the motion. This requires closely coordinating dispensing and motion, and is essentially a group of single dispenses. In yet another alternative, each linear array in a rectangular array of dispense elements may slide relative to one another, so that elements in each linear array may rotate and translate to establish and maintain alignment with rows of sample wells.

The variable-pitch array fluid dispenser generally may be used with various sample holders and various types of dispensing. For example, the dispenser may be used with microplates and surfaces. Similarly, although the dispenser was described primarily in the context of noncontact fluid dispensing, aspects of the invention could be used to position a contact (e.g., pin transfer) fluid dispenser relative to sample wells in a sample holder.

4. Determination of Inter-Well Separations

The fluid dispenser also may include mechanisms for determining the separation between sample positions in a sample holder, and for communicating these separations to an operator and/or an automated controller. These mechanisms may be used to position a sample holder relative to a fluid dispenser, and/or to position a sample holder relative to other devices, such as excitation and/or emission elements in a light detection device. FIGS. 38–39 show several of these mechanisms.

Sample positions may be determined using any mechanism capable of measuring positions, either before or during fluid dispensing. Information regarding sample positions may be determined before fluid dispensing by inspecting individual sample holders, or by inspecting representative sample holders in a batch of sample holders. The latter approach would be most successful if plate-to-plate variations within the batch are small. Information regarding sample positions may be provided to a controller for the dispenser or other device, either manually or automatically. For example, information could be entered manually by an operator, as at a keyboard. Alternatively, information could be entered automatically by encoding the information on the sample holder and then reading the information prior to dispensing. For example, information could be entered using a bar code 3930 on the sample holder and a bar code reader associated with the dispenser.

Information regarding sample positions also may be determined immediately before or during fluid dispensing by inspecting individual sample holders. One method for determining sample positions is to use an imaging device 3932, such as a camera, and image recognition software to identify the actual location of sample positions. Another method is to use a light detection or other device to locate reference fiducials 3234 associated with the sample holder, and to identify the positions of sample wells from the positions of reference fiducials by interpolation and/or extrapolation. Such reference fiducials could include dedicated features, and/or specific sample positions or edges of the sample holder, among others, as described in PCT Patent Application Ser. No. PCT/US99/08410, filed Apr. 16, 1999, and incorporated herein by reference.

Information regarding positions of sample wells may be used by various function modules, including a fluidics module, as here, or an analysis module, as described below.

D. Auxiliary Modules

This section describes auxiliary function modules that may be used alone as stand-alone units or together with or in lieu of fluidics and/or analysis modules in an integrated system for sample preparation and/or analysis. An auxiliary module generally comprises any mechanism or system for performing functions that complement or assist fluid dispensing and/or analysis. Exemplary auxiliary modules include among others (1) a cleaning module, (2) a sample-containment module, and (3) an incubation module.

1. Cleaning Module

A cleaning module generally comprises any mechanism or system for cleaning a sample holder such as a microplate. A cleaning module (or cleaning function) may be integrated with a fluidics module, for example, by alternately aspirating and dispensing cleaning and rinsing fluids with the dispense elements. Alternatively, a cleaning module may be a stand-alone system, for example, having a washer, a dryer, and an outlet.

The washer is used to wash a sample holder using any suitable mechanism or method. Washing comprises removing sample or other impurities. Typically, the washer cleans a sample holder by spraying, immersing, scrubbing, or otherwise sequentially applying cleaning and rinsing fluids to the sample holder. The sample holder is cleaned of sample using the cleaning fluid and rinsed of cleaning fluid (and any residual sample) using the rinsing fluid. The cleaning and rinsing fluids may be identical. The washer may include apparatus for fluid cleaning such as reservoirs and nozzles, and apparatus for contact cleaning such as scrubbers.

The dryer is used to dry a sample holder using any suitable mechanism or method. Drying comprises removing any rinsing fluid remaining after washing. Typically, the dryer dries a sample holder using forced air (or other gas), heat, and/or agitation, among others. The dryer may include apparatus for forcing air such as a gas tank, compressor, and/or nozzle, as well as apparatus for heating and/or agitating such as a heating element or spinner. In some systems, drying may consist simply of room-temperature air drying.

The outlet is used to eliminate discarded sample, and cleaning and rinsing fluids, using any suitable mechanism or method. Typically, the outlet comprises a drain and/or a reservoir.

2. Sample-Containment Module

FIGS. 40–43 show a sample-containment module constructed in accordance with aspects of the invention. The containment module generally comprises any mechanism or system for sealing wells or other reservoirs in a sample holder. The mechanisms may include temporarily applying a sealing sheet to the top of the sample holder and/or removing a sealing sheet prior to dispensing fluid and/or analyzing a sample. The sample holders including microplates may be of a standard design or of a custom design especially intended to work with a particular cover. Aspects of the invention may include (1) cover materials for sample holders, (2) suitably covered sample holders, (3) systems for automatically applying and/or removing covers from sample holders, and/or (4) systems integrating a sample-containment module with a transport module and/or other function modules.

A sample-containment module may be useful in solving problems associated with microplates and other sample holders, particularly for high-throughput applications. For example, microplates include wells having an open face that permits cross-contamination and evaporation. Therefore, it sometimes is desirable to seal the wells in a microplate to isolate the contents of each well from other wells and from the ambient environment. One or both of these functions may be performed in principal by a microplate cover. However, microplate covers that have been used in the past have problems that make them unsuitable for use in a highly automated laboratory setting. In particular, past microplate covers may interfere with or prohibit the stacking and/or unstacking of microplates, due to spatial constraints or limitations in the special handling equipment used to stack and unstack the microplates. Moreover, microplate covers may permit gas exchange, facilitating evaporation. In addition, microplate covers or seals that use adhesive may be difficult to remove or may leave adhesive residue on a surface of a microplate, such that the microplate could stick to other microplates if stacked, unstacked, or otherwise contacted.

Figure 40:
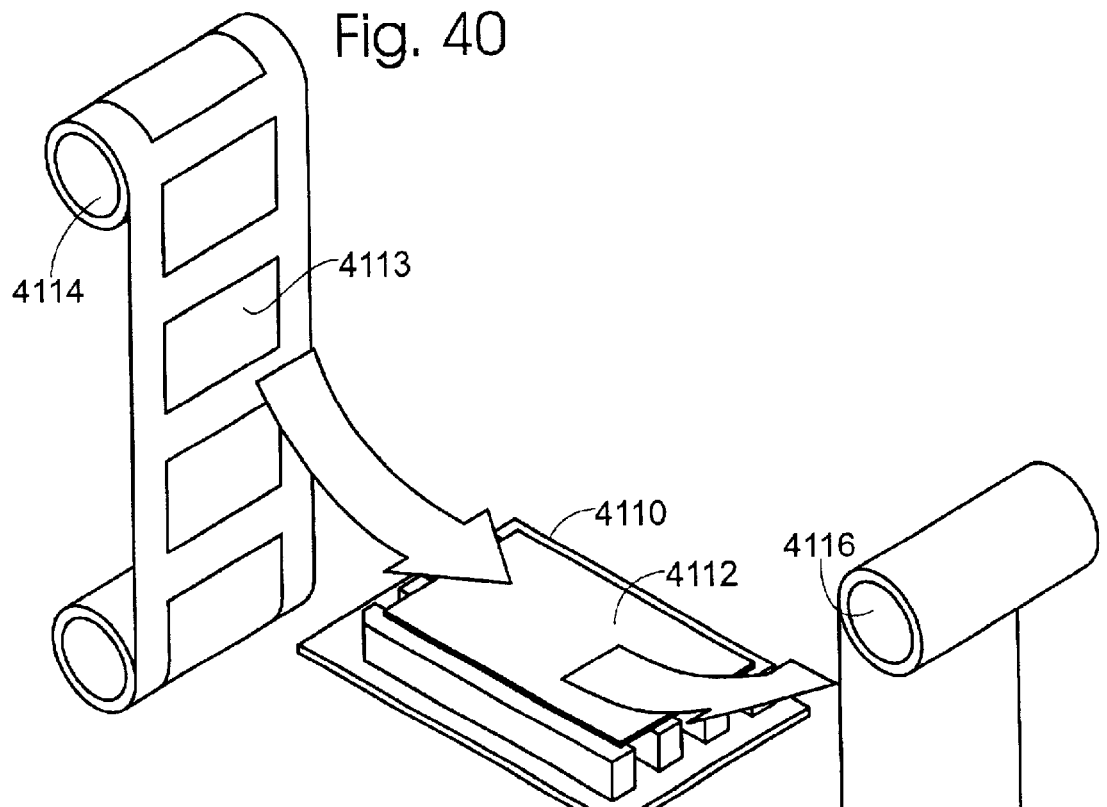
FIG. 40 is a perspective view of a microplate sealing system constructed in accordance with aspects of the invention.

FIG. 40 shows a microplate 4110 and a sealing sheet 4112 covering sample wells (not shown) in the microplate. Rectangular sealing sheets 4113 may be applied to respective microplate tops from an input roll 4114 and/or removed and transferred from microplate tops to an output roll 4116, where they can be stored prior to disposal. Generally, sealing sheets may be stamped and carried on continuous input/output rolls much like industry standard labels. The rolls can be loaded into automated application (sealing) and removal (de-sealing) machines configured to operate with standard and/or specially designed microplates. Stacks of microplates may be fed into application/removal machines, and seals may be applied or removed as desired. Typically, a sealing sheet will be applied to a microplate (or other sample holder) before incubation and/or storage, and removed from a microplate before fluidics operations and/or sample analysis.

Sealing sheets may be designed to include or permit the inclusion of information on the sealing sheet. For example the sealing sheet may include a writeable area and/or a computer readable message or symbol such as a barcode.

Sealing sheets also may be designed to control the amount of light that may pass through the sheet. A sheet may be substantially optically transparent to permit light to pass, for example, so that an optical analysis can be performed through the sheet. Alternatively, a sheet may be substantially optically opaque to prevent light from passing, for example, to reduce photobleaching. A suitable transparent sealing sheet may be made of a clear plastic, and a suitable opaque sealing sheet may be made of aluminum or an aluminized material.

Figure 41:
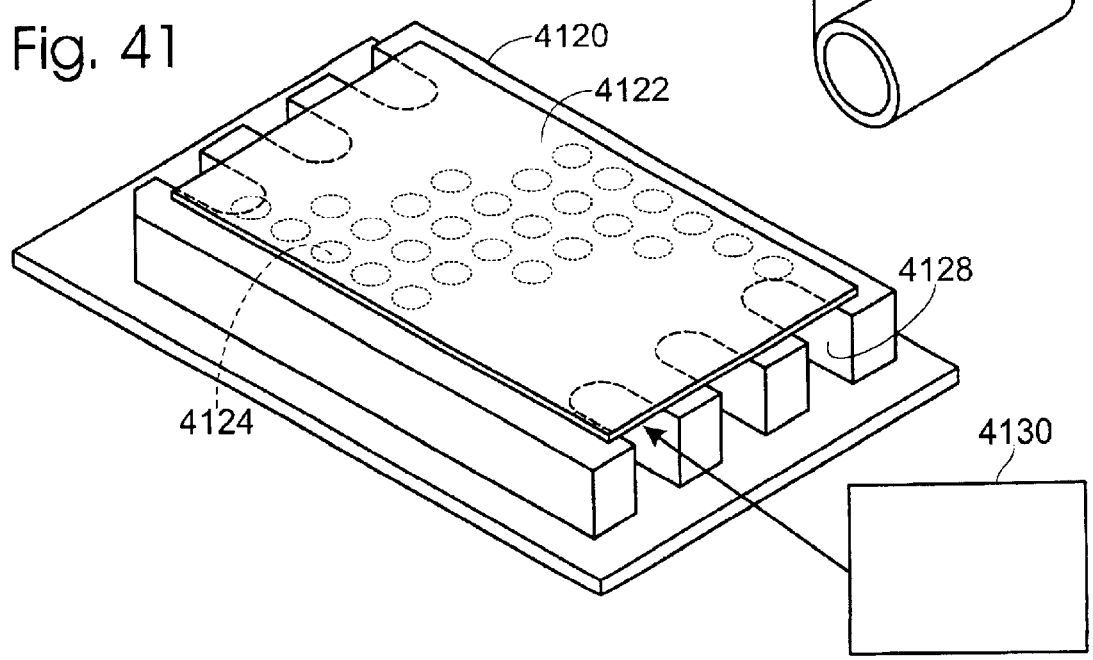
FIG. 41 is a perspective view of a sealed microplate.

FIG. 41 also shows a microplate 4120 and a sealing sheet 4122 covering sample wells 4124 in the microplate. Recesses 4128 are formed in a perimeter portion of microplate 4120 to expose edge regions of sealing sheet 4122 to facilitate removal of the sealing sheet by an automated or robotic device 4130. Robotic device 4130 may include a gripping mechanism and/or picking member for gripping and/or engaging exposed edges of sealing sheet 4122. The robotic device may use a number of different mechanisms to lift sheet 4122 off microplate 4120. For example, the robotic device may grab or clamp the edge of sheet 4122 and then lift the sheet off the microplate. Toward this end, recesses 4128 generally comprise any open area (such as notches) adjacent sealing sheet 4122 sufficient to permit grasping and subsequent pulling of the sheet. The robotic device also may pierce and then lift sheet 4122, or apply a vacuum to and then lift sheet 4122. The robotic device also may apply an adhesive to at least a portion of sheet 4122 before lifting the sheet off microplate 4120.

Figure 42:
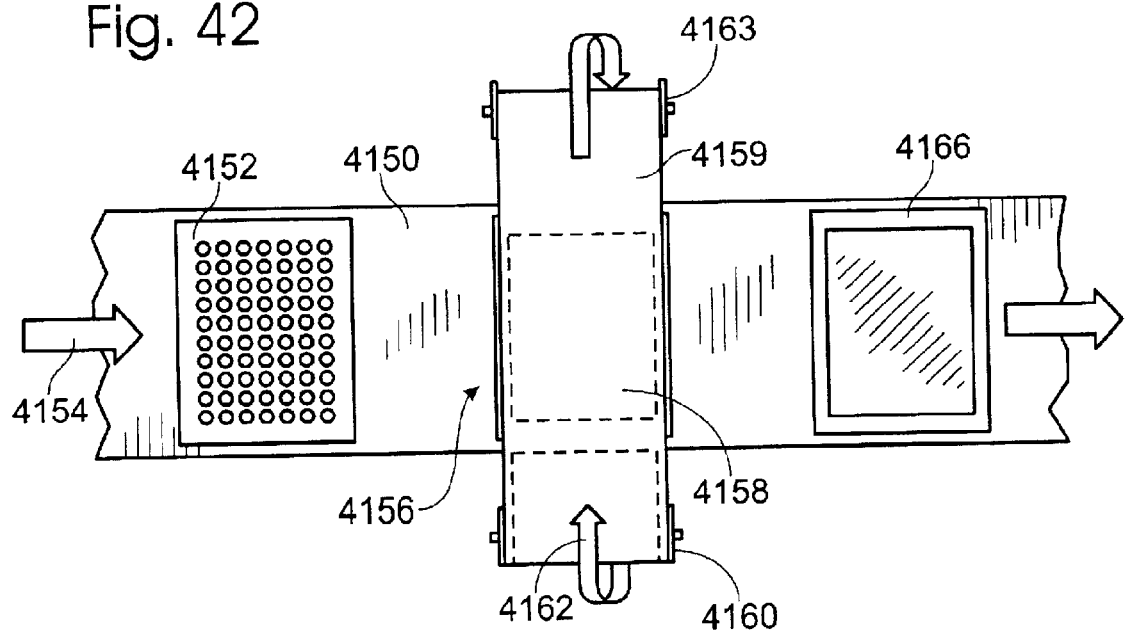
FIG. 42 is a top view of a microplate sealing system, shown applying sheets to a microplate.

FIG. 42 is a partial view of an automated sealing-sheet application system. A conveyor 4150 carries a microplate 4152 in the direction of arrow 4154 toward a sealing-sheet application site 4156. At application site 4156, a sealing sheet 4158, shown in dashed lines on the underside of a continuous carrier 4159, is applied precisely over the sample containment region of microplate 4152. Successive discrete sealing sheets are carried around a first roller 4160 in the direction of arrow 4162. Continuous carrier 4159 is rolled onto a second roller 4163 after removal of sealing sheets at site 4156. The materials of microplate 4152, sealing sheet 4158, and/or carrier 4159 may be selected so that sheet 4158 can be reliably pressed onto microplate 4152 and released from carrier 4159. After applying sealing sheet 4158, conveyor 4150 transports sealed microplate 4166 downstream.

Figure 43:
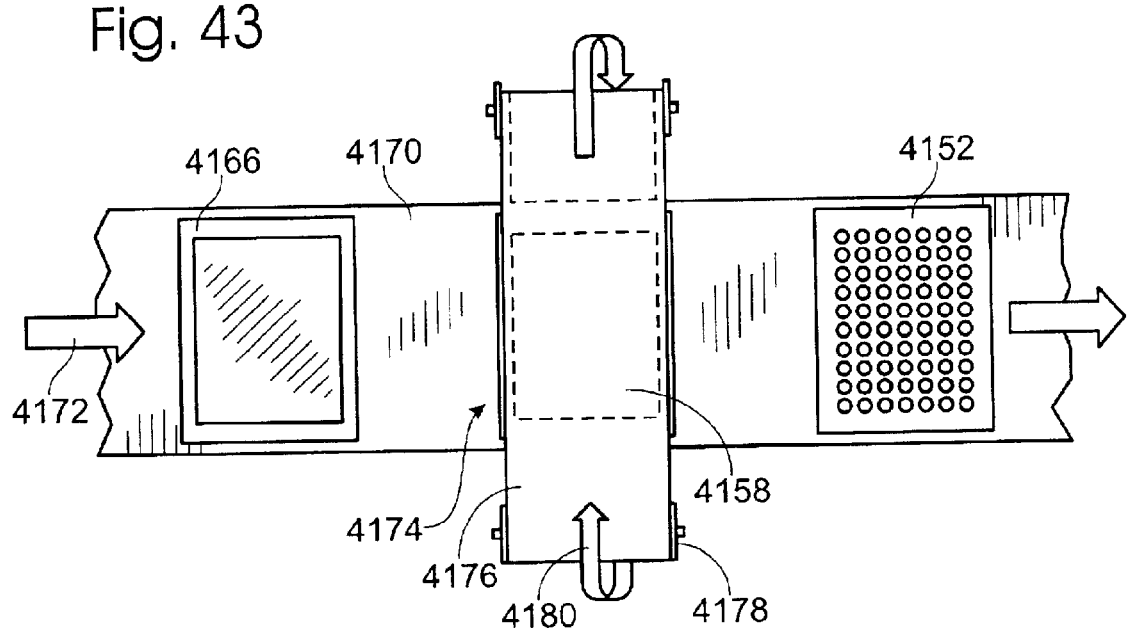
FIG. 43 is a top view of a microplate sealing system, shown removing sheets from a microplate.

FIG. 43 is a partial view of an automated sealing-sheet removal system. A conveyor 4170 transports a sealed microplate 4166 in the direction of arrow 4172 toward a sealing-sheet removal site 4174. At removal site 4174, sheet 4158 is removed from microplate 4152 and transferred to a continuous carrier 4176, which moves around roller 4178 in the direction of arrow 4180. Uncovered microplate 4152 then moves downstream on conveyor 4170. Transfer of sheets from microplate 4152 to carrier 4176 at removal site 4174 may be achieved by selecting a carrier material, optionally containing an adhesive, that can bond to sheet 4158 sufficiently to lift the sheet off microplate 4152.

Various mechanical mechanisms may be used to facilitate transfer of a sealing sheet onto and off a microplate. For example, a pressure member (e.g., mechanical press) may be applied from above the site. It also may be helpful to provide Z-height adjustability of carriers 4159 and 4176 above conveyors 4150 and 4170. It also may be helpful to provide a mechanism for holding the microplate and/or the conveyor when the sealing sheet is being applied and/or removed.

Various mechanical mechanisms also may be used as a conveyor to move microplates into and out of sealing-sheet application and removal stations. Such mechanisms include those described above (especially for the intersite driver) under "Transport Module."

The sealing-sheet application system and sealing-sheet removal system may be configured to enhance flexibility. For example, the systems may be used alone as stand-alone units or together with one another and/or with other function modules as part of an integrated system. The systems also may be used with a variety of sample holders, including but not limited to microplates and other sample holders described above under "Sample Holders."

The invention may provide a microplate sealing system that does not interfere with the stacking of covered microplates and/or leave an adhesive residue on a perimeter portion of the microplate after the sealing sheet is removed. Adhesive residue remaining on a top side of a microplate after a sealing sheet is removed may cause stacked plates to stick together, causing a microplate-handling malfunction downstream. These problems may be substantially avoided by carefully controlling the dimension and placement of a sealing sheet on the top surface of a microplate. Here, the sealing-sheet dimension may be matched to a microplate so that the sheet substantially covers all of the wells in the sample containment region of the microplate, while leaving a top perimeter portion of the microplate exposed for contacting another microplate in a stack without interference. For use with standard microplates, the sealing sheets may be substantially rectangular, with a width in the range of 2.75-inches to 3.25-inches, and a length in the range 4.25-inches to 4.75-inches.

3. Sample Incubation Module

Figure 44:
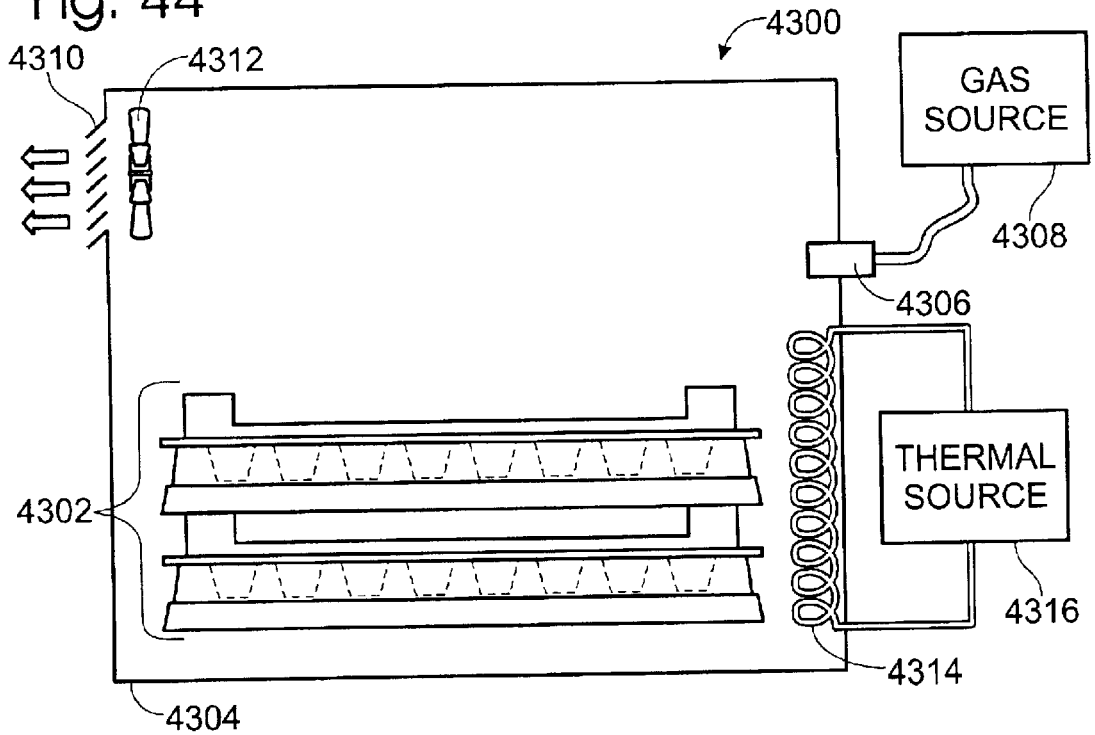
FIG. 44 is a schematic view of a system for controlling ambient conditions around samples contained in wells in a stack of microplates in accordance with aspects of the invention.

FIG. 44 shows an incubation module 4300 constructed in accordance with aspects of the invention. The incubation module generally comprises any mechanism or system for storing or incubating samples with control of ambient environmental conditions, such as temperature, atmosphere (e.g., humidity, $CO_2$ level, etc.), agitation, and so on. The mechanisms may include storing the samples in an environmentally controlled enclosure and/or using spacers or other mechanisms to increase thermal and gas exchange around and between samples. An incubation module may be used to protect thermally sensitive samples such as cells.

Environmental control is especially important with sample holders such as microplates that may be stacked atop one another before, during, and/or after analysis for transport, incubation, and/or storage. Microplates may be stacked to enhance convenience and minimize footprint. For example, incubation module 4300 may support a stack of microplates 4302 in the same shelf area used to support a single microplate. Unfortunately, stacking microplates may limit thermal and gas exchange through the space between the microplates and thereby create gradients in temperature and/or gas composition around the samples. For example, samples contained in a microplate near the top of a stack may be exposed to a substantially different temperature or gas composition than samples contained in microplates near the bottom of the stack.

To facilitate environmental control, the incubation module 4300 may include an enclosure 4304 for storing samples that may be partially or totally sealed from the outside environment. Moreover, the incubation module may include mechanisms for actively controlling the interior environment within the enclosure. For example, incubation module 4300 includes a valve device 4306 on a side of the enclosure for controlling gas flow into and out of the enclosure. Suitable gases such as $CO_2$ may be injected into the enclosure from a gas source 4308 connected to the valve and passively or actively removed from the enclosure to facilitate circulation using a vent 4310, fan 4312, and/or other mechanism. Incubation module 4300 also includes heating and cooling elements 4314 in or around the enclosure for raising or lowering the temperature inside the enclosure. Heating and cooling may be effected from a suitable thermal source 4316. Incubation module 4300 also may include agitation elements such as a rocker for rocking, shaking, and/or otherwise agitating enclosed sample holders to mix or aerate associated samples.

The incubation module may be used in conjunction with other devices and methods for increasing ambient heat and gas exchange around and between samples, especially samples in stacks of sample holders. For example, apertures might be provided in the side of a microplate to allow gas to circulate in the space between adjacently stacked microplates. Alternatively, or in addition, a spacing mechanism might be provided atop or between microplates to separate a microplate from adjacently stacked microplates.

Figure 45:
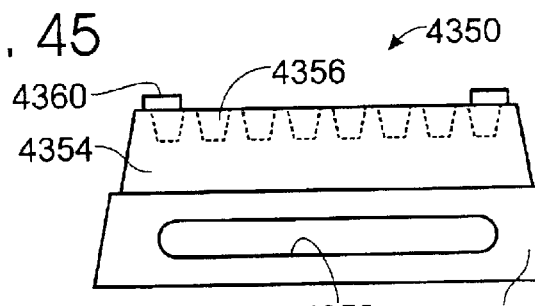
FIG. 45 is a side view of a microplate having an aperture in the base to allow thermal and gas circulation below sample wells contained in the microplate and projections for supporting another microplate.

FIG. 45 shows a microplate 4350 with adaptations for facilitating environmental access between stacked microplates, with or without an intervening spacer. Microplate 4350 includes a frame portion 4352 and a top portion 4354 having a plurality of sample wells 4356. The frame portion includes apertures 4358 to allow thermal and gas circulation between plates. The top portion includes projections 4360 that extend above a plane defined by the tops of the sample wells to support and elevate a microplate stacked above it, also to allow thermal and gas circulation between plates.

Figure 46:
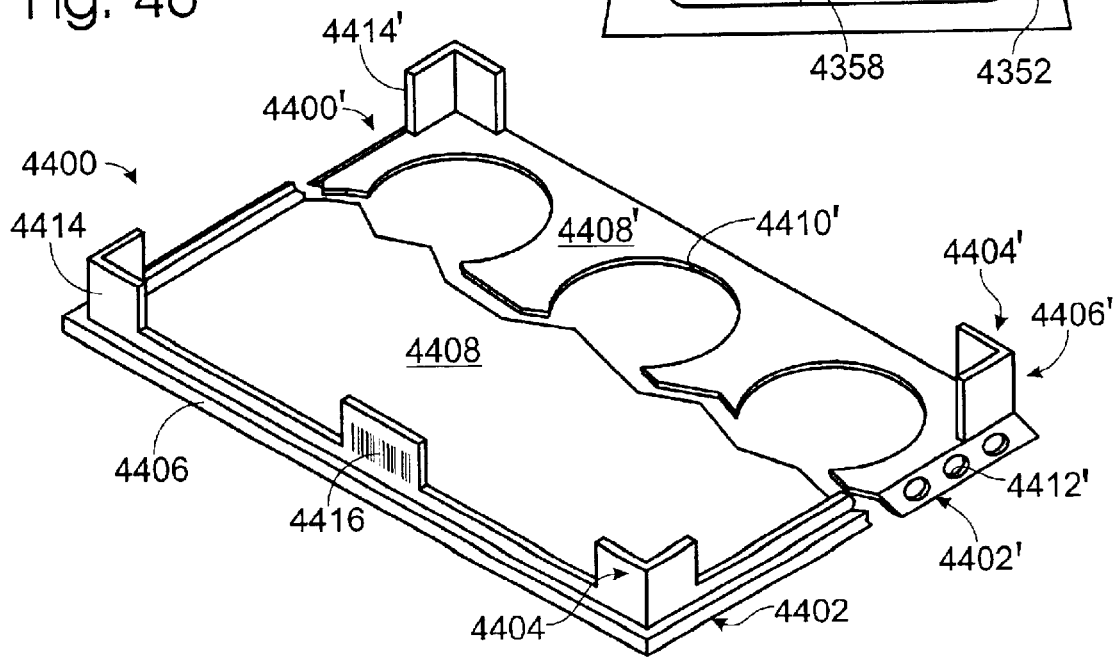
FIG. 46 is a perspective view of portions of two alternative embodiments of a lid-spacer for separating stacked microplates.

FIG. 46 shows portions of two alternative embodiments of a lid-spacer 4400 for facilitating environmental access between stacked microplates. The lid-spacer may be stacked atop, between, or beneath microplates. The lid-spacer may include a lid portion 4402 and a spacer portion 4404.

Lid portion 4402 provides shape and structural support for the lid-spacer and regulates thermal and/or gas exchange over wells in a microplate over which the lid-spacer is stacked. The lid portion may include an exterior frame 4406 and a substantially planar cover portion 4408 surrounded by the frame portion. The lid portion may fit sealingly atop a microplate to seal a space over wells in the microplate, reducing evaporation. Alternatively, the lid portion may fit loosely atop a microplate and/or include apertures 4410 in the frame or operates 4412 in the cover portion to permit thermal and/or gas exchange over wells in the microplate. Alternatively, or in addition, structures such as ridges may be provided on the bottom surface of the lid portion to allow gas diffusion.

Spacer portion 4404 supports and elevates a microplate under which the lid-spacer is stacked, facilitating thermal and/or gas exchange under wells in the microplate. The spacer portion may include projections 4414 that extend upward from the lid portion to support a microplate in a desired spaced orientation. These projections typically will be located at corners of the lid-spacer to enhance stability, but also may be located along sides (especially long sides) of the lid-spacer.

The lid-spacer may be formed of any suitable material and manufactured using any suitable method. A preferred material is plastic, such as that used to form microplates. Preferred manufacturing methods include molding and/or standard machining operations.

The lid-spacer may be sized and shaped to mimic a typical microplate, so that the lid-spacer can be handled (e.g., singulated) by equipment designed to handle a standard microplate. In this way, the lid-spacer may be singulated or re-stacked by a transport mechanism, and the transport mechanism can perform de-lidding and re-lidding operations, if programmed to do so. A possible sequence includes the following steps: (1) singulate microplate from input stack, send to function module; (2) singulate lid-spacer from input stack, send to output stack; (3) send microplate from function module to output stack. This sequence can be repeated as desired.

A lid-spacer may be removed and replaced multiple times during assay preparation, incubation, and/or detection. The lid-spacer may include a bar code 4416 or reference fiducial and/or be sized or formed of a material permitting sample-handling equipment to distinguish it from a microplate or other sample holder. The lid-spacer may be transparent to permit light to pass for photoactivations or to perform a luminescence application through the lid-spacer. Alternatively, the lid-spacer may be opaque to preserve darkness inside the wells to prevent photobleaching prior to a luminescence application. Lid-spacers can be placed at the top and bottom of a stack to ensure that plates are always covered as plates are circulated back and forth in stacks during assay preparation, incubation, and/or detection. A stack of microplates with respective lid-spacers may be transported in a magazine back and forth between an incubator, detector, fluid dispenser, and/or transporter when long-term incubations in a controlled environment are required.

Figure 47:
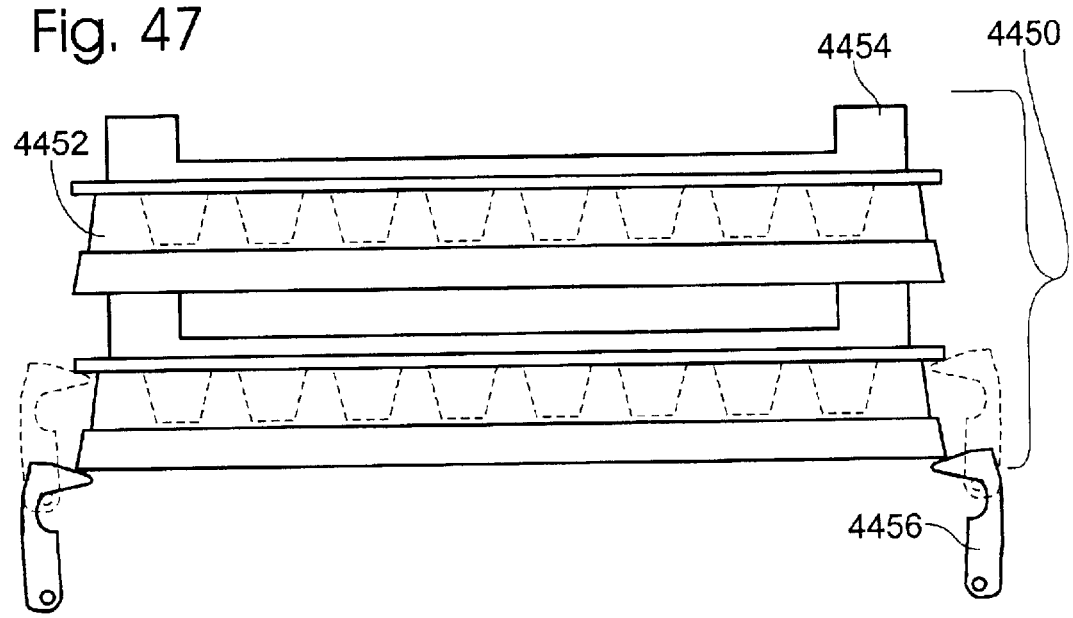
FIG. 47 is a side view of alternated stacked microplates and lid-spacers being manipulated by singulation latches.

FIG. 47 shows a stack 4450 of microplates 4452 and intervening spacing devices 4454. Spacing device 4454 is substantially the same as the lid-spacer shown in FIG. 46. A singulation latch 4456 operates on the bottom of the stack to remove one microplate or one spacing device at a time.

Figure 48:
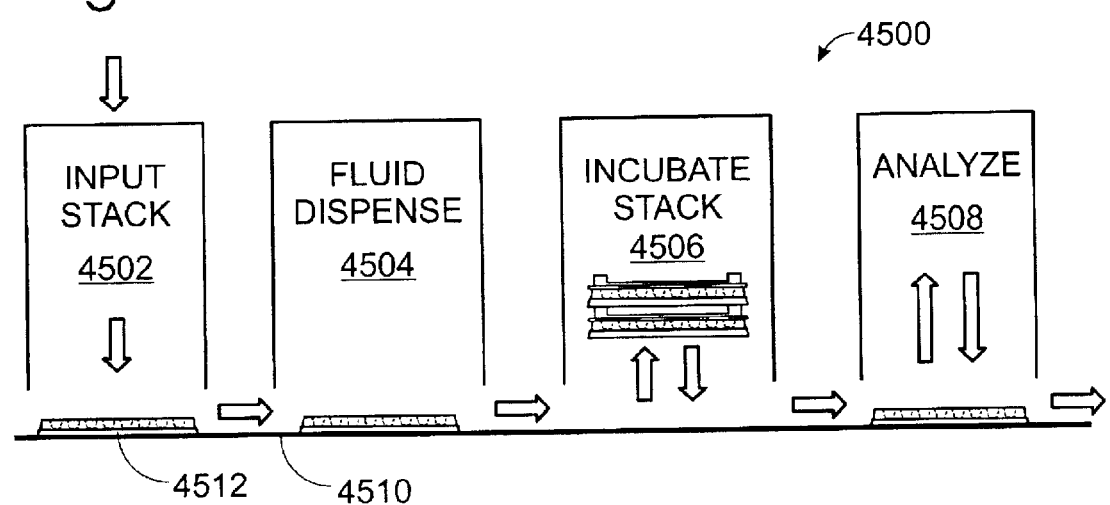
FIG. 48 is a schematic view of a sample processing system utilizing lid-spacing devices in an incubating station.

The incubation module may be used alone as a stand-alone unit or together with one or more other function modules as part of an integrated system. FIG. 48 shows such an integrated system 4500, which may be used to process and analyze a sample contained in a microplate. System 4500 includes a microplate input site 4502, a fluidics module 4504, an incubation module 4506, and an analysis module 4508. A transport module 4510 transports microplates from site to site. A microplate 4512 is singulated from the bottom of a stack in input site 4502. Transport module 4510 transports the microplate to fluidics module 4504, where fluid is added to wells in the microplate. The microplate 4512 is then transported and stacked in incubation module 4506, along with other microplates and intervening spacers and lids in accordance with previously described embodiments of the invention. After the samples are incubated in incubation module 4506, the microplate may be singulated from the bottom of a stack in the incubation module and transported to analysis module 4508 where a test is performed on the sample.

The lid-spacer may be combined advantageously with a microplate sealer. It also may be advantageous to employ semipermeable films or membranes selectively to control environmental access to samples contained in wells under a spacer.

E. Analysis Module

The transport module, fluidics module, and/or auxiliary modules described in the preceding sections may be combined with an analysis module to form an integrated system for sample preparation and/or analysis. An analysis module generally comprises any mechanism or system for analyzing a sample, including qualitative analysis (to determine the nature of the sample and/or its components) and/or quantitative analysis (to determine the amount, relative proportions, and/or activity of the sample and/or its components).

Figure 49:
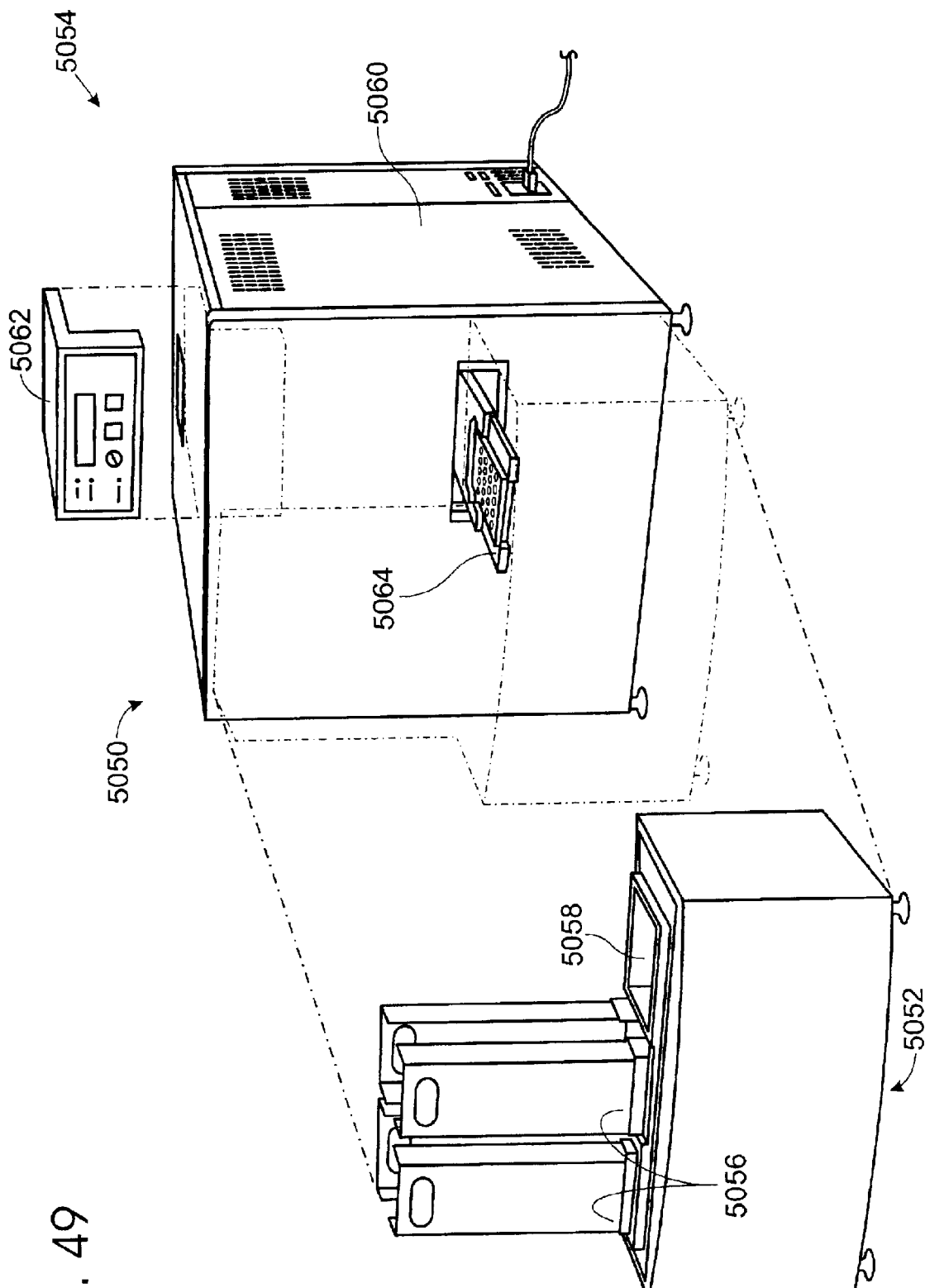
FIG. 49 is a partially exploded perspective view of a system for analyzing samples in accordance with aspects of the invention, showing a transport module and an analysis module.

FIG. 49 shows a system 5050 for analyzing samples that includes a transport module 5052 and an exemplary analysis module 5054 capable of detecting and analyzing light. The transport module includes I/O sites 5056, a transfer site 5058, and mechanisms (not visible) for transporting sample holders between the I/O and transfer sites, as described above. The analysis module includes a housing 5060, a moveable control unit 5062, an optical system (not visible), and a transport mechanism 5064. The housing may be used to enclose the analysis module, protecting both the user and components of the module. The control unit may be used to operate the module manually and/or robotically, as described in U.S. Pat. No. 6,025,985, which is incorporated herein by reference. The optical system and transport mechanisms are described in subsequent sections.

The analysis and transport modules may be configured so that transport mechanism 5064 from analysis module 5054 can interact at transfer site 5058 with an intrasite driver (not visible) from transport module 5052 for sample transfer. More specifically, the transport mechanism may interact with an intrasite driver from the transport module, such as with intrasite driver 2300 and lifters 2308b in FIG. 23.

Further aspects of the analysis module are presented in the following sections: (1) optical system, (2) transport mechanism, and (3) analytical methods.

1. Optical System

FIGS. 50–53 show an optical system (and related components) 5090 for use in system 5050. The optical system may include components for generating and/or detecting light, and for transmitting light to and/or from a sample. These components may include (1) a stage for supporting the sample, (2) one or more light sources for delivering light to the sample, (3) one or more detectors for receiving light transmitted from the sample and converting it to a signal, (4) first and second optical relay structures for relaying light between the light source, sample, and detector, and/or (5) a processor for analyzing the signal from the detector. Module components may be chosen to optimize speed, sensitivity, and/or dynamic range for one or more assays. For example, optical components with low intrinsic luminescence may be used to enhance sensitivity in luminescence assays by reducing background. Module components also may be shared by different assays, or dedicated to particular assays. For example, steady-state photoluminescence assays may use a continuous light source, time-resolved photoluminescence assays may use a time-varying light source, and chemiluminescence assays may not use a light source. Similarly, steady-state and time-resolved photoluminescence assays may both use a first detector, and chemiluminescence assays may use a second detector.

Optical system 5090 includes (a) a photoluminescence optical system, and (b) a chemiluminescence optical system, as described below. Further aspects of the optical system are described in the following patent applications, which are incorporated herein by reference: U.S. patent application Ser. No. 09/160,533, filed Sep. 24, 1998; U.S. patent application Ser. No. 09/349,733, filed Jul. 8, 1999; PCT Patent Application Ser. No. PCT/US99/16287, filed Jul. 26, 1999; and PCT Patent Application Ser. No. PCT/US00/04543, filed Feb. 22, 2000.

a. Photoluminescence Optical System

Figure 50:
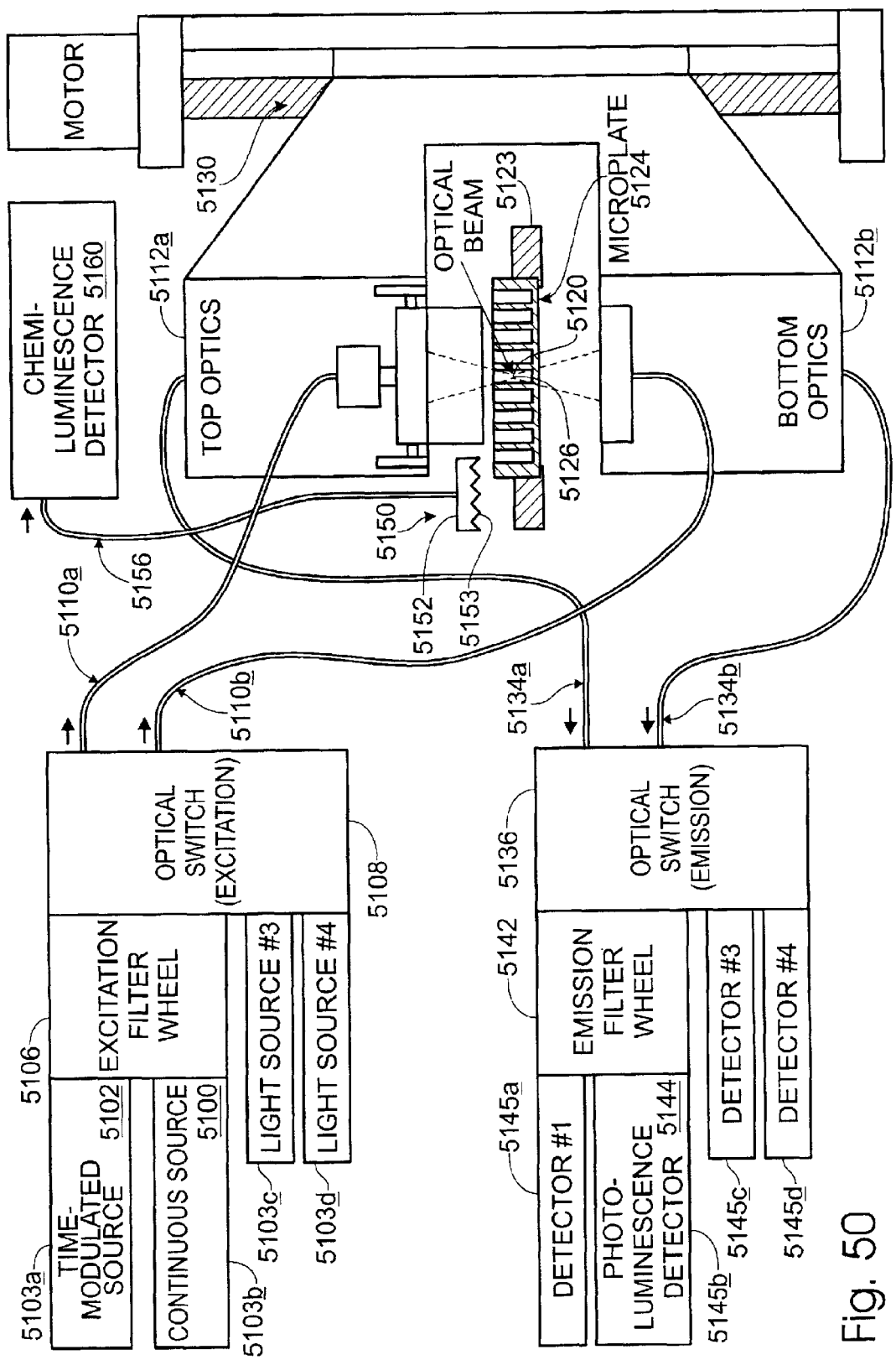
FIG. 50 is a schematic view of an optical system from the analysis module of FIG. 49.
Figure 51:
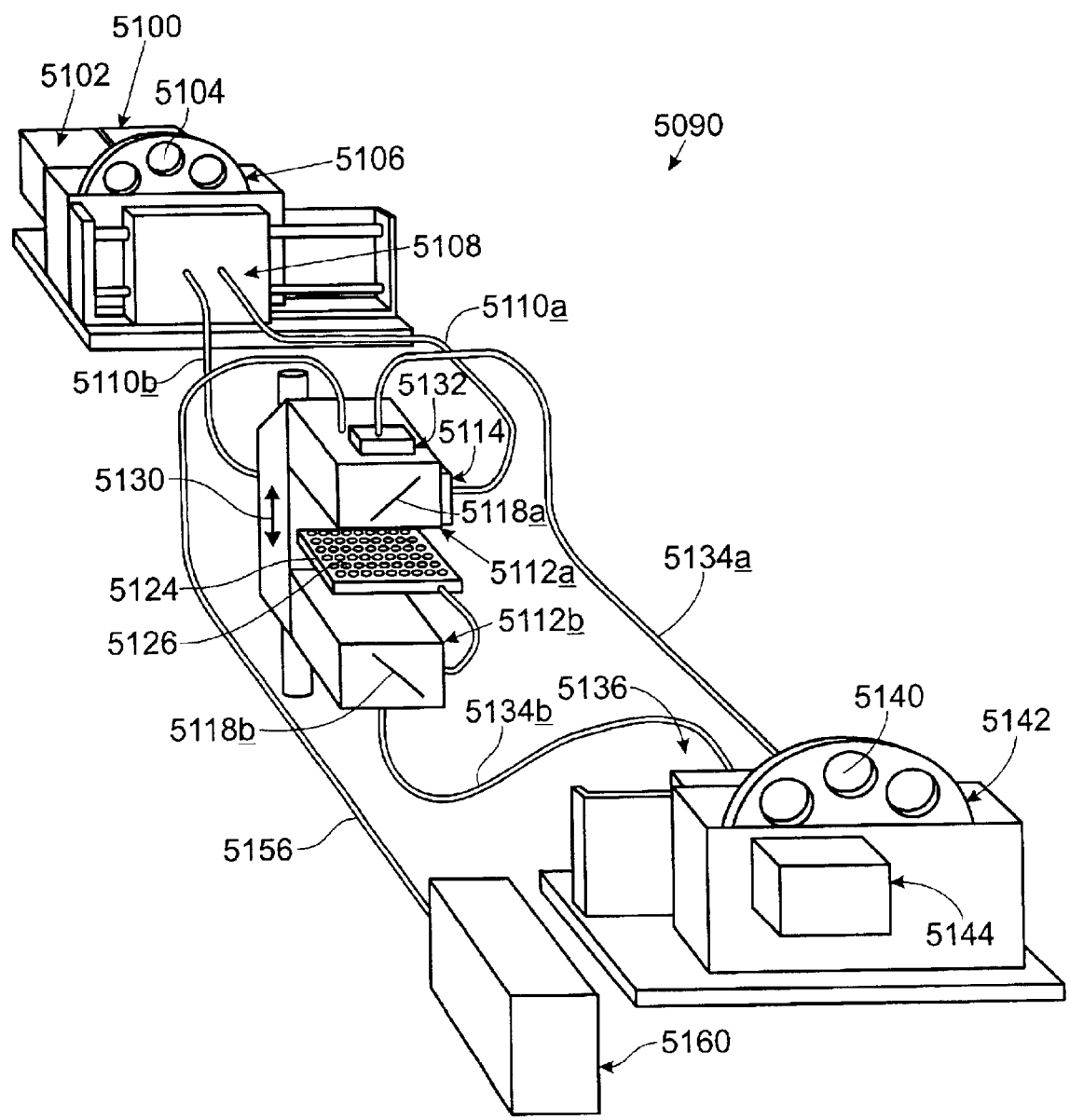
FIG. 51 is a partially schematic perspective view of the apparatus of FIG. 50.
Figure 52:
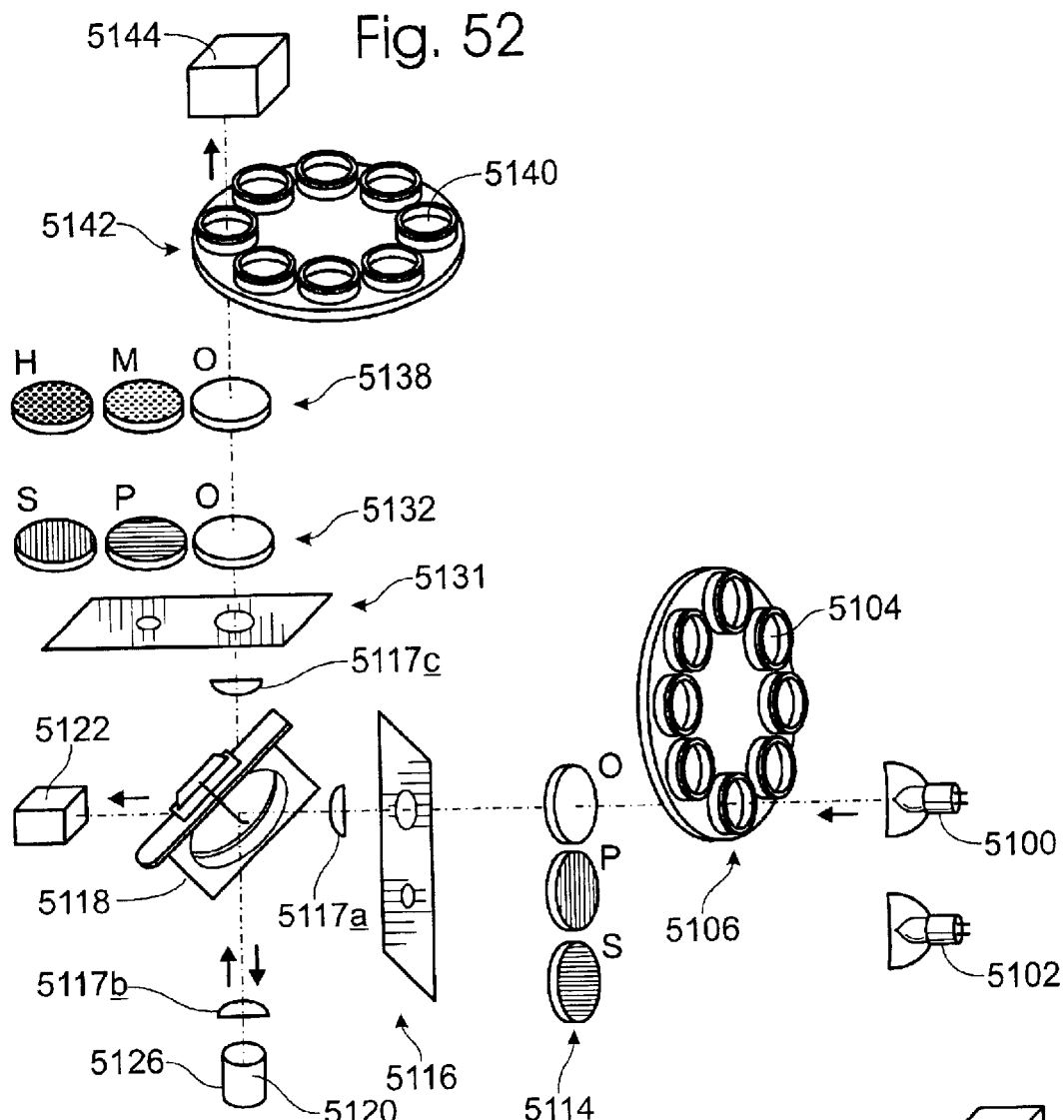
FIG. 52 is a schematic view of photoluminescence optical components from the apparatus of FIG. 50.

FIGS. 50–52 show the photoluminescence (or incident light-based) optical system of optical system 5090. As configured here, optical system 5090 includes a continuous light source 5100 and a time-modulated light source 5102. Optical system 5090 includes light source slots 5103a–d for four light sources, although other numbers of light source slots and light sources also could be provided. Light source slots 5103a–d function as housings that may surround at least a portion of each light source, providing some protection from radiation and explosion. The direction of light transmission through the incident light-based optical system is indicated by arrows.

Continuous source 5100 provides light for absorbance, scattering, photoluminescence intensity, and steady-state photoluminescence polarization assays. Continuous light source 5100 may include arc lamps, incandescent lamps, fluorescent lamps, electroluminescent devices, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the flash source duty cycle, increasing sensitivity and reducing read times. Optical system 5090 may include a modulator mechanism configured to vary the intensity of light incident on the sample without varying the intensity of light produced by the light source. Further aspects of the continuous light source are described in U.S. patent application Ser. No. 09/349,733, filed Jul. 8, 1999, which is incorporated herein by reference.

Time-modulated source 5102 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a Pockels cell, Kerr cell, or other mechanism. Such other mechanisms may include an amplitude modulator such as a chopper as described in PCT Patent Application Ser. No. PCT/US99/16287, filed Jul. 26, 1999, which is incorporated herein by reference. Extrinsically modulated continuous light sources are especially well suited for frequency-domain measurements.

In optical system 5090, continuous source 5100 and time-modulated source 5102 produce multichromatic, unpolarized, and incoherent light. Continuous source 5100 produces substantially continuous illumination, whereas time-modulated source 5102 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In optical system 5090, spectrum is altered by an excitation interference filter 5104, which preferentially transmits light of preselected wavelengths and preferentially absorbs light of other wavelengths. For convenience, excitation interference filters 5104 may be housed in an excitation filter wheel 5106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 5106 may be mounted in the optical path of some light source slots 5103a,b, but not other light source slots 5103c,d. Alternatively, the filter wheel may include a blank station that does not affect light passage.

Light next passes through an excitation optical shuttle (or switch) 5108, which positions an excitation fiber optic cable 5110a,b in front of the appropriate light source to deliver light to top or bottom optics heads 5112a,b, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In optical system 5090, polarization is altered by excitation polarizers 5114, which are included only with top optics head 5112a for top reading; however, such polarizers also can be included with bottom optics head 5112b for bottom reading. Excitation polarization filters 5114 may include an s-polarizer S that passes only s-polarized light, a p-polarizer P that passes only p-polarized light, and a blank O that passes substantially all light, where polarizations are measured relative to the beamsplitter. Excitation polarizers 5114 also may include a standard or ferro-electric liquid crystal display (LCD) polarization switching system. Such a system may be faster than a mechanical switcher. Excitation polarizers 5114 also may include a continuous mode LCD polarization rotator with synchronous detection to increase the signal-to-noise ratio in polarization assays. Excitation polarizers 5114 may be incorporated as an inherent component in some light sources, such as certain lasers, that intrinsically produce polarized light. Further aspects of the polarization filters and their use in polarization assay are described in U.S. patent application Ser. No. 09/349,733, filed Jul. 8, 1999, which is incorporated herein by reference.

Light at one or both optics heads also may pass through an excitation "confocal optics element," which generally comprises any mechanism for focusing light into a "sensed volume." In optical system 5090, the confocal optics element includes a set of lenses 5117a–c and an excitation aperture 5116 placed in an image plane conjugate to the sensed volume, as shown in FIG. 52. Aperture 5116 may be implemented directly, as an aperture, or indirectly, as the end of a fiber optic cable. Preferred apertures have diameters of 1 mm and 1.5 mm. Lenses 5117a,b project an image of aperture 5116 onto the sample, so that only a preselected or sensed volume of the sample is illuminated. The area of illumination will have a diameter corresponding to the diameter of the excitation aperture.

Light traveling through the optics head is directed onto a beamsplitter 5118, which reflects light toward a sample 5120 and transmits light toward a light monitor 5122. The reflected light passes through lens 5117b, which is operatively positioned between beamsplitter 5118 and sample 5120.

Beamsplitter 5118 is used to direct excitation or incident light toward the sample and light monitor, and to direct light leaving the sample toward the detector. The beamsplitter is changeable, so that it may be optimized for different assay modes or samples. In some embodiments, switching between beamsplitters may be performed manually, whereas in other embodiments, such switching may be performed automatically. Automatic switching may be performed based on direct operator command, or based on an analysis of the sample by the instrument. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the sample, and while still transmitting considerable light leaving the sample to the detector. If one or a few related photoactive molecules are to be studied, the beamsplitter needs only to be able to accommodate light at a limited number of wavelengths; in this case, a "dichroic" or "multidichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

The beamsplitter more generally comprises any optical device for dividing a beam of light into two or more separate beams. A simple beamsplitter (such as a 50:50 beamsplitter) may include a very thin sheet of glass inserted in the beam at an angle, so that a portion of the beam is transmitted in a first direction and a portion of the beam is reflected in a different second direction. A more sophisticated beamsplitter (such as a dichroic or multi-dichroic beamsplitter) may include other prismatic materials, such as fused silica or quartz, and may be coated with a metallic or dielectric layer having the desired transmission and reflection properties, including dichroic and multi-dichroic transmission and reflection properties. In some beamsplitters, two right-angle prisms are cemented together at their hypotenuse faces, and a suitable coating is included on one of the cemented faces. Further aspects of the beamsplitter are described in PCT Patent Application Serial No. PCT/US00/06841, filed Mar. 15, 2000, which is incorporated herein by reference.

Light monitor 5122 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The sample (or composition) may be held in a sample holder supported by a stage 5123. The sample can include compounds, mixtures, surfaces, solutions, emulsions, suspensions, cell cultures, fermentation cultures, cells, tissues, secretions, and/or derivatives and/or extracts thereof. Analysis of the sample may involve measuring the presence, concentration, or physical properties (including interactions) of a photoactive analyte in such a sample. Sample may refer to the contents of a single microplate well, or several microplate wells, depending on the assay. In some embodiments, such as a portable apparatus, the stage may be intrinsic to the instrument.

The sample holder can include microplates, biochips, or any arrangement of samples in a known format, as described above. In optical system 5090, the preferred sample holder is a microplate 5124, which includes a plurality of microplate wells 5126 for holding samples. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in a 8×12 rectangular array on 9 millimeter centers.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in U.S. patent application Ser. No. 09/062,472, filed Apr. 17, 1998, which is incorporated herein by reference.

The position of the sensed volume can be moved precisely within the sample to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In optical system 5090, position in the X,Y-plane perpendicular to the optical path is controlled by moving the stage supporting the sample, whereas position along the Z-axis parallel to the optical path is controlled by moving the optics heads using a Z-axis adjustment mechanism 5130, as shown in FIGS. 50 and 51. However, any mechanism for bringing the sensed volume into register or alignment with the appropriate portion of the sample also may be employed. For example, the optics head also may be scanned in the X,Y-plane, as described in U.S. Provisional Patent Application Ser. No. 60/142,721, filed Jul. 7, 1999, which is incorporated herein by reference.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and has been used in the past for absorbance assays. In optical system 5090, epi modes are supported, so the excitation and emission light travel the same path in the optics head, albeit in opposite or anti-parallel directions. However, trans modes also can be used with additional sensors, as described below. In optical system 5090, top and bottom optics heads move together and share a common focal plane. However, in other embodiments, top and bottom optics heads may move independently, so that each can focus independently on the same or different sample planes.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light may be transmitted by the sample in multiple directions. A portion of the transmitted light will follow an emission pathway to a detector. Transmitted light passes through lens 5117c and may pass through an emission aperture 5131 and/or an emission polarizer 5132. In optical system 5090, the emission aperture is placed in an image plane conjugate to the sensed volume and transmits light substantially exclusively from this sensed volume. In optical system 5090, the emission apertures in the top and bottom optical systems are the same size as the associated excitation apertures, although other sizes also may be used. The emission polarizers are included only with top optics head 5112a. The emission aperture and emission polarizer are substantially similar to their excitation counterparts. Emission polarizer 5132 may be included in detectors that intrinsically detect the polarization of light.

Excitation polarizers 5114 and emission polarizers 5132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 5118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 5134a,b to an emission optical shuttle (or switch) 5136. This shuttle positions the appropriate emission fiber optic cable in front of the appropriate detector. In optical system 5090, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In optical system 5090, intensity is altered by emission neutral density filters 5138, which absorb light substantially independent of its wavelength, dissipating the absorbed energy as heat. Emission neutral density filters 5138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beam splitters, which transmit some light along one path and reflect other light along another path, and diffractive beam splitters (e.g., acousto-optic modulators), which deflect light along different paths through diffraction. Examples also include hot mirrors or windows that transmit light of some wavelengths and absorb light of other wavelengths.

Light next may pass through an emission interference filter 5140, which may be housed in an emission filter wheel 5142. In optical system 5090, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the sample, among other factors.

Light last passes to a detector, which is used in absorbance, scattering and photoluminescence assays, among others. In optical system 5090, there is one detector 5144, which detects light from all modes. A preferred detector is a photomultiplier tube (PMT). Optical system 5090 includes detector slots 5145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described in PCT Patent Application Ser. No. PCT/US99/03678.

b. Chemiluminescence Optical System

Figure 53:
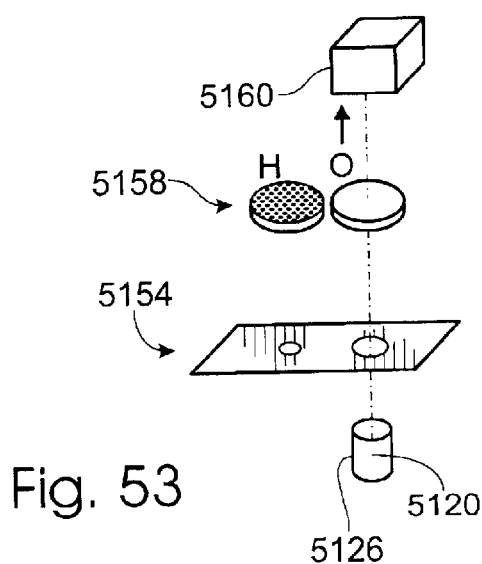
FIG. 53 is a schematic view of chemiluminescence optical components from the apparatus of FIG. 50.

FIGS. 50, 51, and 53 show the chemiluminescence optical system of optical system 5090. Because chemiluminescence follows a chemical event rather than the absorption of light, the chemiluminescence optical system does not require a light source or other excitation optical components. Instead, the chemiluminescence optical system requires only selected emission optical components. In optical system 5090, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the incident light-based optical system. The chemiluminescence optical system also can be used for other assay modes that do not require illumination, such as electrochemiluminescence.

The chemiluminescence optical path begins with a chemiluminescent sample 5120 held in a sample holder 5126. The sample and sample holder are analogous to those used in photoluminescence assays; however, analysis of the sample involves measuring the intensity of light generated by a chemiluminescence reaction within the sample rather than by light-induced photoluminescence. A familiar example of chemiluminescence is the glow of the firefly.

Chemiluminescence light typically is transmitted from the sample in all directions, although most will be absorbed or reflected by the walls of the sample holder. A portion of the light transmitted through the top of the well is collected using a chemiluminescence head 5150, as shown in FIG. 50, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the sample. Detecting from a sensed volume reduces contributions to the chemiluminescence signal resulting from "cross talk," which is pickup from neighboring wells. The nonconfocal mechanism includes a chemiluminescence baffle 5152, which includes rugosities 5153 that absorb or reflect light from other wells. The nonconfocal mechanism also includes a chemiluminescence aperture 5154 that further confines detection to a sensed volume.

Light next passes through a chemiluminescence fiber optic cable 5156, which may be replaced by any suitable mechanism for directing light from the sample toward the detector. Fiber optic cable 5156 is analogous to excitation and emission fiber optic cables 5110$a,b$ and 5134$a,b$ in the photoluminescence optical system. Fiber optic cable 5156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In optical system 5090, intensity is altered by chemiluminescence neutral density filters 5158. Light also may pass through other filters, if desired.

Light last passes to a detector, which converts light into signals that may be processed by the apparatus. In optical system 5090, there is one chemiluminescence detector 5160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

2. Transport Mechanism

FIGS. 54–57 show a transport mechanism or stage, which generally comprises any mechanism for supporting a sample in a sample holder for analysis by an analysis module. (The transport module also may be used to support a sample for fluid dispensing, as described above.) In analysis module 5054, the stage includes a transporter 5600 and base platform 5700.

Figure 54:
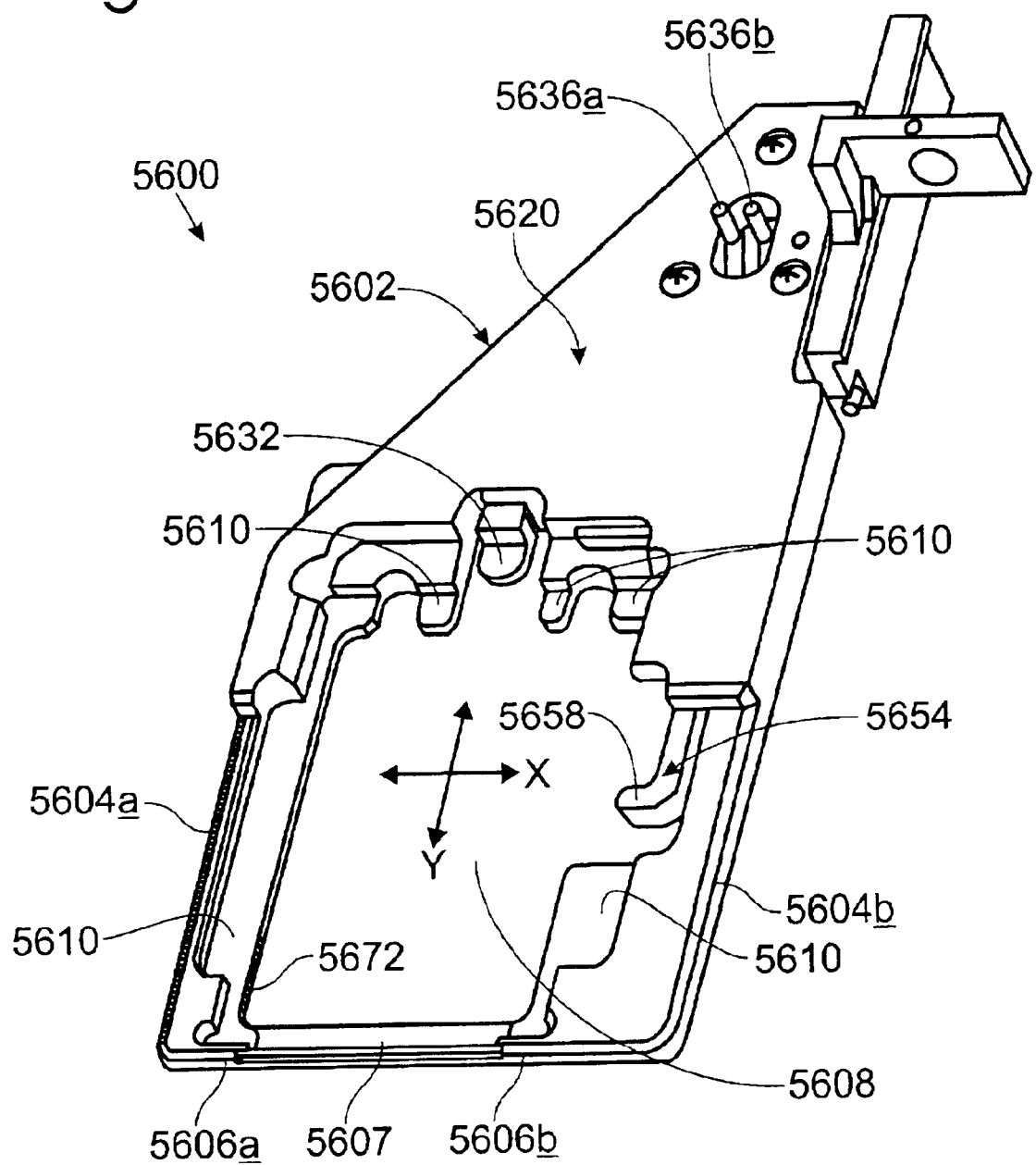
FIG. 54 is a top perspective view of a portion of a transport mechanism from the analysis module of FIG. 49.
Figure 55:
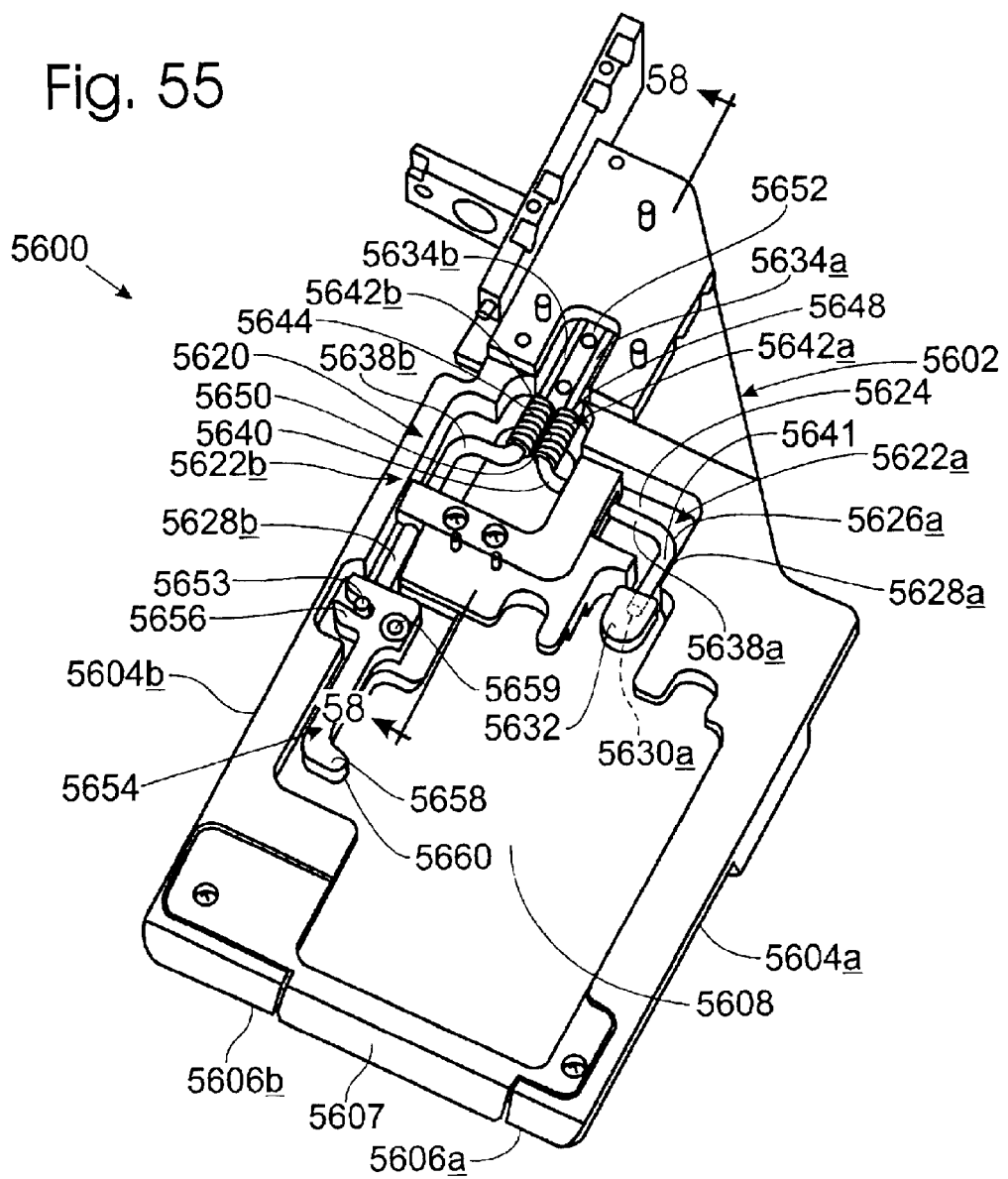
FIG. 55 is a bottom perspective view of the portion of a transport mechanism shown in FIG. 54.
Figure 56:
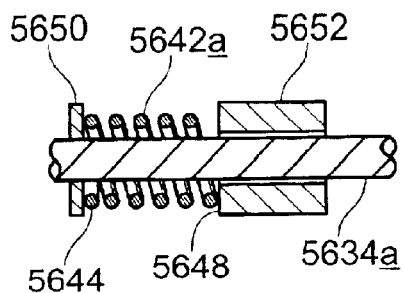
FIG. 56 is a partial cross-sectional view of the portion of a transport mechanism shown in FIGS. 54 and 55, taken generally along the line 56—56 in FIG. 55.

FIGS. 54–56 show transporter 5600, which includes a transporter body 5602 and substantially parallel first and second transporter flanges 5604$a,b$ that extend outward from transporter body 5602. First and second transporter flanges 5604$a,b$ terminate in first and second transporter extensions 5606$a,b$ that turn in toward one another without contacting one another. Transporter extensions 5606$a,b$ may be joined by a connector portion 5607. Transporter body 5602, flanges 5604$a,b$, and extensions 5606$a,b$ lie substantially in a plane and define a transporter cavity 5608 that is larger than the expected peripheral dimension of any sample holders which the transporter is intended to support. The shape of this cavity is chosen to accommodate the shape of the preferred sample holders. In analysis module 5054, cavity 5608 is generally rectangular to accommodate generally rectangular sample holders, such as microplates. In analysis module 5054, long sides of the rectangular sample holder are positioned against flanges 5604$a,b$.

Transporter 5600 includes a shelf structure and associated frame structure for supporting a microplate or other sample holder. For example, transporter shelves 5610 along portions of body 5602, flanges 5604$a,b$, and extensions 5606$a,b$ form a shelf structure that supports the bottom of the sample holder. The shelf structure also could include other support mechanisms, such as pins or pegs.

The transporter also includes an automatic sample holder positioning mechanism 5620 for positioning sample holders precisely and reproducibly within cavity 5608. Mechanism 5620 includes Y and X axis positioning arms 5622$a,b$ that contact the sample holder to control its Y and X position, respectively. Here, a Y axis is defined as generally parallel to transporter flanges 5604$a,b$, and an X axis is defined as perpendicular to the Y axis and generally parallel to transporter extensions 5606$a,b$. Other coordinate systems also can be defined, so long as they include two noncolinear directions.

Y-axis positioning arm 5622$a$ lies substantially within a channel 5624 in body 5602. Y-axis positioning arm 5622$a$ includes a rod 5626$a$, which is bent at substantially right angles to form three substantially coplanar and equal-lengthed segments. A first end segment 5628$a$ of rod 5626$a$ terminates near cavity 5608 in a bumper 5632 for engaging a sample holder. A second end segment 5634$a$ of rod 5626$a$ terminates away from cavity 5608 in an actuator tab 5636$a$ for controlling movement of arm 5622$a$. Actuator tab 5636$a$ is bent away from body 5602. First and second end segments 5628$a$, 5634$a$ are substantially parallel. A middle segment 5638$a$ of rod 5626$a$ connects the two end segments at their nontabbed ends 5640, 5641. An X-axis biasing spring 5642$a$ having first and second spring ends 5644, 5648 is slipped over rod 5626$a$. First spring end 5644 is held to second end segment 5634$a$ of rod 5626$a$ by a clamping-type retaining ring 5650. Second spring end 5648 rests against a rod bearing 5652. The Y-axis biasing spring extends substantially parallel to first and second end segments 5628$a$, 5634$a$. The force from spring 5642$a$ is transmitted to rod 5626$a$ by the clamping action of retaining ring 5650.

X-axis positioning arm 5622$b$ also lies substantially within channel 5624 in body 5602 and is similar to Y-axis positioning arm, except that (1) first end segment 5628$b$ is longer and middle segment 5638$b$ is shorter in rod 5626$b$ of the X-axis positioning arm than in rod 5626$a$ of the Y-axis positioning arm, (2) first end segment 5628$a$ terminates in a lever tab 5653 in the X-axis positioning arm rather than in bumper 5632 in the Y-axis positioning arm, and (3) the two rods bend in opposite directions between first end segments 5628$a,b$ and second end segments 5634$a,b$.

X-axis positioning arm 5622$b$ is connected via lever tab 5653 to an X-axis positioning lever 5654 that lies along transporter flange 5604$b$. X-axis positioning lever 5654 includes first and second lever projections 5656, 5658 and is pivotally mounted about a lever pivot axis 5659 to transporter 5600 near the intersection of body 5602 and flange 5604$b$. First lever projection 5656 is substantially perpendicular to flange 5604$b$ and abuts lever tab 5630$b$ on X-axis positioning arm 5622$b$ for actuating the positioning lever. Second lever projection 5658 also is substantially perpendicular to flange 5604$b$ and includes an edge 5660 for contacting a sample holder.

Transporter 5600 functions as follows. For loading, the transporter occupies a loading position substantially outside a housing. In this position, actuator tabs 5636a,b abut an actuator bar 5670, shown in FIG. 57. In addition, biasing springs 5642a,b are compressed, and bumper 5632 and second projection 5658 having edge 5660 are pulled out of cavity 5608. A person, robot, or mechanical stacker then can place a sample holder into cavity 5608 so that the bottom of the sample holder rests on shelves 5610. Cavity 5608 is larger than the sample holder to facilitate this placement and to accommodate variations in sample holder size.

In some configurations, connector portion 5607 may be removed, such that transporter 5600 has an open end. This open end permits a microplate transfer device to enter cavity 5608 and the generally rectangular area of the holder. The microplate transfer device may, after moving into the generally rectangular area, move down relative to transporter 5600, thereby gently placing the microplate into the generally rectangular area.

For reading, the transporter must deliver the sample holder to an examination site inside the housing. In this process, the transporter moves parallel to second end segments 5634a,b, and actuator tabs 5636a,b disengage actuator bar 5670. Biasing spring 5642a pushes Y-axis positioning arm 5622a toward cavity 5608. Bumper 5632 engages the sample holder and pushes it away from body 5602 until it abuts extensions 5606a,b. Biasing spring 5642b pushes X-axis positioning arm 5622b toward cavity 5608. Edge 5660 of second projection 5658 engages the sample holder and pushes it away from flange 5604b until it abuts flange 5604a.

As long as the sample holder is placed in any position on the lower guide shelves, it may be positioned (registered) precisely and reproducibly against a reference corner 5672 within cavity 5608 under the action of both positioning arms. Biasing springs 5642a,b can be chosen to have different strengths, so that the X-Y positioning action is performed less or more forcefully. In analysis module 5054, middle segment 5638b and first lever projection 5656 of positioning lever 5654 can be varied in length to cause registration to occur in series, first along the X-axis or first along the Y-axis, and second along the Y-axis or second along the X-axis, respectively. For example, reducing the length of middle segment 5638b and reducing the length of projection 5656 will cause registration to occur first in the X-axis, and second in the Y-axis.

Positioning lever 5654 and bumper 5632 are retracted when body 5602 of the automatic microplate positioning transporter is moved to the eject position by the X,Y stage. Thus, the microplate is placed on transporter shelf 5610 only when the lever and bumper are retracted. Two springs 5642a,b are attached to the rods, which run along the length of the transporter body and end perpendicular to the body. When the transporter is moved to the eject position, the two perpendicular ends of the rods encounter a stop 5670, which consists of a rectangular structure located above and parallel to the body. The stop prevents the two perpendicular ends of the actuators, and thus the actuators, from moving with the transporter body. This causes the two springs to contract, changing the position of the transporter arms and increasing the amount of room for the microplate. The microplate then can be placed on the guide shelf of the body. When the body of the automatic microplate positioning transporter is moved back away from the stop, the two perpendicular ends of the actuators no longer are blocked, which allows the actuators, springs, and transporter arms to move into their original position. The expansion of the springs pushes the microplate exactly into position, as defined by the reference corner.

Thus, components of transporter 5600 act as first and second releasable clamp mechanisms. The first releasable clamp mechanism applies a force against a first (e.g., Y or X) side of the microplate, thereby securing the microplate in the holder. The second releasable clamp mechanism applies a force against a second (e.g., X or Y) side of the microplate, thereby securing the microplate in the holder from two sides. These clamp mechanisms may sandwich a microplate between the positioning arms and opposing portions of the frame structure, such that the positioning arms function as pushers and the opposing portions of the frame structure function as bumpers for the clamp mechanisms.

The invention provides a method of automatically feeding microplates in and out of an analyzer. The method comprises (1) automatically delivering a microplate just outside an opening to the analyzer, (2) moving a gripping device from inside the analyzer, through the opening, to a location immediately below the microplate; and (3) gently placing the microplate onto the gripping device. The method further may comprise clamping the microplate in the holder by applying a first force against a first side of the microplate, applying a second force against a second side of the microplate, and/or serially performing the clamping steps.

Figure 57:
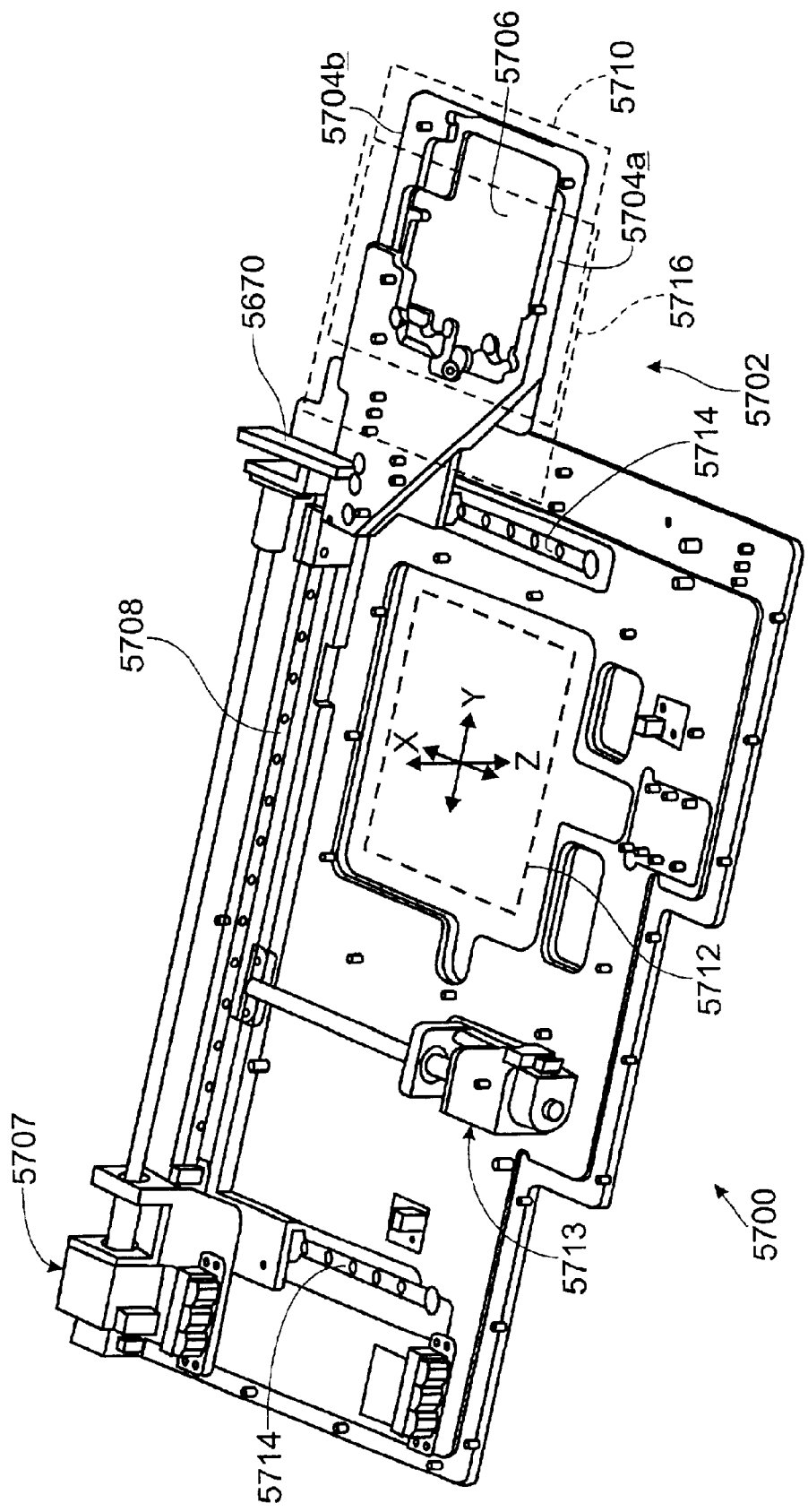
FIG. 57 is a perspective view of a base platform and associated drive mechanisms for moving the portion of a transport mechanism shown in FIGS. 54—56 along X and Y axes relative to the base platform.

FIG. 57 shows a base platform 5700 with drive mechanisms for moving a transporter 5702 between loading and examination positions or sites. As previously described, transporter 5702 includes flanges 5704a,b defining a cavity 5706 for receiving and gripping a microplate (not shown). A Y-axis drive mechanism 5707 is provided for moving transporter 5702 along a first track 5708 relative to the Y-axis, from a loading position 5710 toward an examination position 5712. An X-axis drive mechanism 5713 is provided to move transporter 5702 to examination position 5712 along a second track 5714 relative to the X-axis.

In operation, a microplate is loaded in transporter 5702 at loading position 5710. This loading position may correspond to the transfer site for a transport module, as shown in FIG. 49. Transporter 5702 is then driven toward the examination site (and/or optional fluid dispense site 5716) by Y-axis drive mechanism 5707. A sensor (not shown) detects the presence of the sample holder. The analyzer may be configured automatically to read the microplate once the sensor detects its presence, or the analyzer may be configured to signal the system controller through a data port that a microplate has been received and that the analyzer is ready to accept a command to begin reading. The X- and Y-axis drive mechanisms then operate together to align selected microplate wells with an optical axis, substantially parallel to a Z-axis, along which a sensed volume for luminescence detection may be defined by optical components contained in one or both of a top and bottom optics head positioned above and below base platform 5700, respectively.

Transporter 5700 thus may function both as a sample delivery device in and out of the analyzer, and as a moveable stage for supporting the sample holder at the examination site (and/or at the optional fluid dispense site). The cavity in the transporter permits analysis to be carried out from below the holder, when the transporter is functioning as a stage at the examination site.

X- and Y-axis drive mechanisms 5707 and 5713 may be controlled by a high-performance motion control system that maximizes throughput while minimizing detection errors. A preferred high-performance control system includes precision five-phase stepper motors that employ encoder feedback to move the microplate quickly and accurately to each read position. The control system may optimize the acceleration/deceleration profiles of the microplate to minimize shaking of fluid within the microplate, for example, by minimizing "jerk" (the time rate of change of the acceleration of the microplate). Alternatively, the control system may increase throughput by moving plates more quickly, if higher variation in results due to increased shaking and settling time may be tolerated.

3. Analytical Methods

Analysis modules may be used to analyze a sample, qualitatively or quantitatively, as described above. Suitable methods for such analysis may include spectroscopic, hydrodynamic, and imaging methods, among others, especially those adaptable to high-throughput analysis of multiple samples.

Spectroscopic methods may involve interaction of light (or wavelike particles) with matter, and may involve monitoring some property of the light that is changed due to the interaction. Suitable spectroscopic methods may include absorption, luminescence (including photoluminescence, chemiluminescence, and electrochemiluminescence), magnetic resonance (including nuclear and electron spin resonance), scattering (including light scattering, electron scattering, and neutron scattering), circular dichroism, and optical rotation, among others. Suitable photoluminescence methods may include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), and fluorescence recovery after photobleaching (FRAP), as well as their phosphorescence and higher-order-transition analogs, among others.

Hydrodynamic methods may involve interaction of a molecule or other compound with its neighbors, its solvent, and/or a matrix, and may be used to characterize molecular size and/or shape, or to separate a sample into its components. Suitable hydrodynamic methods may include chromatography, sedimentation, viscometry, and electrophoresis, among others.

Imaging methods may involve any method for visualizing a sample or its components, including optical microscopy and electron microscopy, among others.

These and other methods such as luminescence lifetime-based background subtraction are described in further detail in the patent applications and publications listed above under "Cross-References," which are incorporated herein by reference.

F. Additional Examples

This section describes selected additional aspects of the invention, as recited in the following numbered paragraphs:

1. A device for transferring fluid between first and second locations, the device comprising a mount, and at least one pin moveably attached to the mount, each pin having a base portion and a tip portion extending away from the base portion, the base portion being configured to be attached to the mount, and the tip portion being configured to retain a substantially reproducible volume of a fluid when brought into contact with the fluid for transfer between the first and second locations.

2. The device of paragraph 1, wherein the mount includes an elastomeric material.

3. The device of paragraph 1, wherein the mount includes a frame capable of dynamically adjusting the arrangement of the pins.

4. The device of paragraph 3, wherein the frame dynamically adjusts the vertical position of the pins relative to a sample.

5. The device of paragraph 3, wherein the frame dynamically adjusts the horizontal position of the pins relative to a sample.

6. The device of paragraph 1 further comprising a drive mechanism configured to move the mount between the first and second positions.

7. The device of paragraph 1, the device configured to transfer fluid to or from a sample container having a reference fiducial encoding information about the sample container, further comprising a reader capable of determining the information encoded in the reference fiducial.

8. The device of paragraph 1, wherein the pin is configured to transfer an amount of fluid equal to one or fewer microliters.

9. The device of paragraph 1, the device including at least three pins, wherein the pins are arranged in a regular array.

10. The device of paragraph 9, wherein the array is one-dimensional.

11. The device of paragraph 9, wherein the array is two-dimensional.

12. A device for dispensing fluid to a plurality of sample sites in a sample holder, the device comprising (a) a dispense site configured to support a sample holder having a plurality of sample wells, (b) a dispense manifold having a plurality of dispense elements, each dispense element capable of dispensing fluid to a sample site, (c) a controller configured to receive information regarding sample positions and to automatically adjust the effective separation between the dispense elements to correspond to the separation between the sample site in the sample holder, and (d) a registration device configured to bring the dispense elements and at least a portion of the sample site into register, so that fluid may be dispensed from the dispense elements to the sample sites.

13. The device of paragraph 12, wherein the dispense elements are configured for noncontact fluid dispensing.

14. The device of paragraph 12, wherein the sample holder is a microplate and the sample sites correspond to wells in the microplate.

15. The device of paragraph 12, wherein the sample holder is a substantially planar surface, and wherein the sample sites are positioned in the substantially planar surface.

16. The device of paragraph 12, the sample holder having a bar code encoding information regarding positions of sample sites, further comprising a bar code reader configured to scan the bar code.

17. The device of paragraph 12, the sample holder having a reference fiducial encoding information regarding positions of sample sites in the sample holder, further comprising a reference fiducial reader configured to read the reference fiducial.

18. The device of paragraph 12 further including an imaging device configured to image at least a portion of the sample holder, so that the positions of sample sites may be determined.

19. The device of paragraph 12, the sample sites and dispense elements being fixed, wherein the effective separation between the dispense elements may be adjusted to correspond to the separation between the sample sites in the sample holder by changing the relative orientation of the dispense elements and sample sites.

20. The device of paragraph 19, the dispense elements forming a substantially linear array constrained to rotate about a pivot point, wherein the relative orientation of the sample sites and dispense elements may be changed by rotating the dispense elements about the pivot point.

21. The device of paragraph 12 further comprising dispensing fluid from the dispense elements to the sample sites.

22. The device of paragraph 21, wherein the fluid is dispensed simultaneously from each dispense element.

23. The device of paragraph 21, wherein the fluid is dispensed sequentially from each dispense element.

24. The device of paragraph 12, wherein the separations between dispense elements are variable.

25. The device of paragraph 12, wherein the separations between dispense elements are fixed.

26. The device of paragraph 12, wherein the dispense elements are configured to dispense a range of fluid volume including volumes of less than about 1 microliter.

27. A method for dispensing fluid to a plurality of sample sites in a sample holder, the method comprising (a) providing a fluid dispenser having a plurality of dispense elements, each dispense element configured to dispense fluid, (b) providing a sample holder having a plurality of sample sites, each sample site configured to hold a fluid, (c) obtaining information regarding the positions of the sample sites in the sample holder, (d) automatically adjusting the effective positions of the dispense elements to correspond to the positions of the sample sites using the information regarding the positions of the sample sites, (e) bringing the dispense elements and at least a portion of the sample sites into register, and (f) dispensing fluid from the dispense elements to the sample sites.

28. The method of paragraph 27, wherein the step includes the step of separating droplets from the dispense elements without contacting the droplets to a surface.

29. The method of paragraph 27, wherein the sample holder is a microplate.

30. The method of paragraph 27, wherein the sample holder has a substantially planar surface, and wherein the sample sites are positioned in the substantially planar surface.

31. The method of paragraph 27, wherein the step of obtaining information includes scanning an area on the sample holder.

32. The method of paragraph 31, wherein the pre-encoded information is encoded using a bar code, and wherein the sample is scanned using a bar code reader.

33. The method of paragraph 27, wherein the step of obtaining information includes measuring the positions of the sample sites during or immediately prior to dispensing fluid.

34. The method of paragraph 33, wherein the step of measuring the positions includes the step of imaging at least a portion of the sample holder using an imaging device.

35. The method of paragraph 33, wherein the step of measuring the positions includes the steps of locating the position of a reference fiducial and inferring the positions of the sample sites from the position of the reference fiducial by at least one of interpolation and extrapolation.

36. The method of paragraph 27, the sample sites and dispense elements being fixed, wherein the step of automatically adjusting the effective positions of the dispense elements includes the step of changing the relative orientation of the sample sites and dispense elements.

37. The method of paragraph 36, the dispense elements forming a substantially linear array constrained to rotate about a pivot point, wherein the step of changing the relative orientation of the sample sites and dispense elements includes the step of rotating the dispense elements about the pivot point.

38. The method of paragraph 27 further comprising dispensing fluid from the dispense elements to the sample sites.

39. The method of paragraph 38, wherein the fluid is dispensed simultaneously from each dispense element.

40. The method of paragraph 38, wherein the fluid is dispensed sequentially from each dispense element.

41. The method of paragraph 27 further comprising (a) providing a second sample holder having a plurality of sample sites, each sample site configured to hold a fluid, (b) obtaining information regarding the positions of the sample sites in the second sample holder, and (c) automatically readjusting the effective positions of the dispense elements to correspond to the positions of the sample sites in the second sample holder using the information regarding the positions of the sample sites in the second sample holder.

42. The method of paragraph 41, wherein the separations between dispense elements are variable.

43. The method of paragraph 27, wherein the separations between dispense elements are fixed.

44. The method of paragraph 27, wherein the dispense elements are capable of dispensing a fluid aliquot of less than about 1 microliter.

45. A device for spacing microplates, the device comprising a spacing member dimensioned to maintain separation between stacked first and second microplates.

46. The device of paragraph 45, wherein the spacing member includes a lid portion.

47. The device of paragraph 46, wherein the lid portion substantially covers the sample wells in a microplate stacked below.

48. The device of paragraph 45, wherein the spacing member has a frame portion.

49. The device of paragraph 48, wherein the frame portion substantially mimics a frame portion of a typical microplate so that a stacker or destacker can manipulate the spacing member as it would a microplate.

50. The device of paragraph 48, wherein the frame portion has at least one aperture for allowing environmental circulation between adjacently stacked microplates.

51. The device of paragraph 45, wherein the spacing member includes one or more upwardly extending projections.

52. The device of paragraph 46, wherein the lid portion has at least one aperture for allowing environmental access to samples contained in wells under the spacing member.

53. A method of allowing environmental access between stacked microplates, the method comprising spacing adjacent microplates in a stack.

54. The method of paragraph 53 further comprising the step of providing at least one aperture in a side of a frame member between stacked microplates.

55. The method of paragraph 53 further comprising the step of controlling ambient gas constituents and temperature around and between stacked microplates.

56. The method of paragraph 53 further comprising the step of circulating a gas between stacked microplates.

57. A method of allowing environmental access between stacked microplates, the method comprising projecting spacing members between microplates in a stack.

58. A method of allowing environmental access between stacked microplates, the method comprising elevating one microplate above another microplate by situating a spacing member between the microplates.

59. The method of paragraph 58 further comprising the step of configuring the spacing member to mimic the perimetral dimensions of a typical microplate so that the spacing member can be manipulated by a microplate stacker or destacker.

60. The method of paragraph 59 further comprising the step of automatically stacking and de-stacking the spacing member.

61. A microplate comprising (a) a frame member, (b) a plurality of sample wells contained within the frame member, the wells having upper edges contained in a common plane, and (c) one or more projections extending above the plane, so that the wells maintain a spaced relationship to a microplate stacked on top.

62. A system for automatically covering and uncovering wells in a microplate, the system comprising (a) a supply of flexible sheet members, (b) a sealing device that automatically positions a sealing sheet over an array of wells in a microplate, and presses the sealing sheet onto the microplate so that the wells are substantially sealed, and (c) a sheet removal device that automatically contacts and lifts the sealing sheet off the microplate.

63. The system of paragraph 62, wherein the sheet removal device has a picking member that removes the sealing sheet by gripping an edge of the sheet.

64. The system of paragraph 62, wherein the sheet removal device has a picking member that pierces and then lifts the sheet from the microplate.

65. The system of paragraph 62, wherein the sheet removal device has a picking member that applies a vacuum to at least a portion of the sheet.

66. The system of paragraph 62, wherein the sheet removal device has a picking member that applies an adhesive to at least a portion of the sealing sheet.

67. A device for removing a sealing sheet from a microplate, the device comprising (a) a microplate-sheet removal station, and (b) a sheet-handling mechanism positioned near the sheet removal station, and configured to contact and lift a sealing sheet off a sealed microplate.

68. The device of paragraph 67, wherein the sheet-handling mechanism has a picking member that grips an edge of the sheet.

69. The device of paragraph 67, wherein the sheet-handling mechanism has a picking member that pierces the sheet and then lifts the sheet from the microplate.

70. The device of paragraph 67, wherein the sheet-handling mechanism has a picking member that applies a vacuum to at least a portion of the sheet.

71. The device of paragraph 67, wherein the sheet-handling mechanism has a picking member that applies an adhesive to at least a portion of the sheet.

72. A microplate sealing system comprising (a) a first microplate having a plurality of wells in a sample containment area, and a frame area surrounding the sample containment area, wherein the microplate is designed so that it can be stacked below a second microplate, and (b) a flexible sealing sheet covering the sample containment area of the first microplate without contacting the second microplate when it is stacked on top of the first microplate.

73. The system of paragraph 72, wherein the first microplate has at least one recess in a side exposing top and bottom sides of an edge of the sealing sheet for easy gripping and removal of the sheet from the microplate.

74. The system of paragraph 72, wherein the flexible sealing sheet is dimensioned to substantially cover the sample containment area of the microplate without contacting the frame area of the microplate.

75. The system of paragraph 72, wherein the flexible sealing sheet is substantially optically transparent relative to an optical analysis to be carried out on a sample contained in a well of the microplate.

76. The system of paragraph 72, wherein the flexible sealing sheet is substantially optically opaque.

77. A cover material for microplates comprising (a) a continuous roll of backing material, and (b) a series of discrete sealing sheets releasably fixed on a surface of the backing material, wherein each sheet is dimensioned to cover substantially all of a plurality of wells of a standard microplate while leaving a peripheral top portion of the microplate uncovered.

78. A method of applying a cover sheet to a microplate, the method comprising (a) applying a sealing sheet over substantially all of the wells in a microplate without covering a continuous perimetral top region of the microplate, and (b) exposing top and bottom sides of an edge portion of the sealing sheet for gripping when the sealing sheet is removed.

79. The method of paragraph 78, wherein the applying step is performed manually.

80. The method of paragraph 78, wherein the applying step is automated.

81. The method of paragraph 78 further comprising the step of removing the sealing sheet from the microplate prior to performing an analysis on a sample contained in a well in the microplate.

82. The method of paragraph 81, wherein the removing step is performed manually.

83. The method of paragraph 81, wherein the removing step is automated.

84. The method of paragraph 78 further comprising the step of forming at least one recess in a side of the microplate so that top and bottom sides of the edge portion are exposed.

85. The method of paragraph 78, wherein the sealing sheet is substantially rectangular.

86. A sample holder comprising (a) a top portion containing an array of sample wells, and (b) a seal covering one or more of the wells, wherein top and bottom sides of an edge portion of the seal are exposed to facilitate removal of the seal.

87. The sample holder of paragraph 86, wherein the top portion has at least one recess below an edge of the seal.

88. The sample holder of paragraph 86, wherein the top portion has a plurality of recesses on at least two sides of the plate.

89. The sample holder of paragraph 86, wherein the sample holder is a microplate.

90. The sample holder of paragraph 86, wherein the seal is substantially rectangular.

91. A sample holder comprising a top portion containing an array of sample wells within a perimeter portion, wherein the top portion has at least one recess in the perimeter portion for exposing an edge of a seal that covers one or more of the wells.

92. An automated device comprising a gripping mechanism configured to contact an exposed edge of a sealing sheet on a microplate, and to remove the sheet from the microplate.

93. The automated device of paragraph 92, wherein the gripping mechanism pierces and lifts the sealing sheet from the microplate.

94. The automated device of paragraph 92, wherein the gripping mechanism applies a vacuum to at least a portion of the sealing sheet.

95. The automated device paragraph 92, wherein the gripping mechanism applies an adhesive to at least a portion of the sealing sheet.

96. A first sample container device comprising (a) a base portion, (b) a plurality of wells formed in a top side, the wells having upper edges defining a plane above the base portion, and (c) at least one elevation mechanism extending above the plane to hold a second sample container in spaced relation to the first sample container.

97. The device of paragraph 96, wherein the elevation mechanism includes at least four post members connected to the top side and extending upward from the plane.

98. The device of paragraph 96, wherein the elevation mechanism includes four post members, each post member extending upward from a corner of the first sample container.

99. The device of paragraph 96, wherein the elevation mechanism is independent from the first sample container.

100. The device of paragraph 96, wherein the base portion has at least one aperture to allow gas circulation under the wells.

101. The device of paragraph 196, wherein wells are provided in the top side of the first sample container in a density of at least about 4 wells per 81 $mm^2$.

102. The device of paragraph 196, wherein the elevation mechanism has a lid portion that substantially covers all of the wells in the top side of the first sample container.

103. An incubation system, comprising (a) an enclosure, (b) at least two microplates stacked within the enclosure, each microplate having a plurality of wells for containing samples, and (c) a spacing mechanism between the two plates to allow gas diffusion and thermal equilibration around samples contained in wells of the microplate.

104. The system of paragraph 103, wherein the spacing mechanism has an outer frame dimension similar to a microplate so that a stacking device designed to handle microplates can also handle the spacing mechanism.

105. The system of paragraph 103, wherein at least one of the microplates has a lateral aperture for allowing gas to circulate between the plates.

106. The system of paragraph 103, wherein the spacing mechanism is formed in a top side of one of the microplates.

107. The system of paragraph 103, wherein the spacing mechanism is a separate piece from the two microplates.

108. The system of paragraph 103, wherein the enclosure is a room.

109. The system of paragraph 103, wherein the enclosure is a sealed chamber.

110. The system of paragraph 103, wherein the enclosure has a valve for allowing controlled passage of gas in and out of the enclosure.

111. A method of controlling a gas environment around a plurality of samples, comprising (a) dispensing samples into a plurality of wells in a first microplate and a second microplate, (b) stacking a spacing mechanism on top of the first microplate, and (c) stacking the second microplate on top of the spacing mechanism to allow gas diffusion and thermal equilibration around the samples.

112. The method of paragraph 111 further comprising the step of providing lateral apertures in the microplates.

113. The method of paragraph 111 further comprising the step of monitoring the temperature of a space containing the microplates.

114. The method of paragraph 111 further comprising the step of incubating the microplates in an enclosure.

115. A device for spacing microplates, the device comprising (a) first and second microplates, and (b) a spacing member separating the first and second microplates in a stack.

116. The device of paragraph 115, wherein the spacing member includes a lid portion.

117. The device of paragraph 115, wherein each microplate has a plurality of sample wells, the lid portion substantially covering the sample wells so that evaporation from the sample wells is minimized while allowing thermal communication between the environment and the space between the microplates.

118. The device of paragraph 115, wherein the spacing member has a frame portion, the frame portion being designed to substantially mimic a frame portion of a typical microplate so that a stacker or destacker can manipulate the spacing member as it would a microplate.

119. The device of paragraph 118, wherein the frame portion has at least one aperture for allowing gas and thermal circulation between the microplates.

120. The device of paragraph 115, wherein the spacing member includes one or more upwardly extending projections.

121. The device of paragraph 114, wherein the lid portion has at least one aperture for allowing environmental access to samples contained in wells under the spacing member.

Although the invention has been disclosed in preferred forms, the specific embodiments thereof as disclosed and illustrated herein are not to be considered in a limiting sense, because numerous variations are possible. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

We claim:

1. A system for delivering fluid to a sample holder comprising
    a fluid source,
    a positive displacement pump connected to the fluid source,
    a dispenser assembly having an orifice, and
    a conduit path extending from the pump to the orifice of the dispenser assembly,
    wherein operation of the positive displacement pump provides non-contact deposition of fluid aliquots having a volume of less than about 5 microliters per aliquot without closing or constricting the conduit path between the deposition of successive fluid aliquots.

2. The system of claim 1 further comprising a controller that determines the volume of each fluid aliquot.

3. The system of claim 1, wherein the pump pumps incrementally at a rate corresponding to the rate of aliquot deposition.

4. The system of claim 1, wherein the dispenser assembly has a hydrophobic tip portion.

5. The system of claim 4, wherein the tip portion is made of a heat-shrinkable material.

6. The system of claim 5, wherein the tip portion is made of material selected from the group consisting of PTFE, polypropylene, polyethylene, and FEP.

7. The system of claim 1, wherein the dispenser assembly has a tip portion made of sapphire.

8. The system of claim 1, wherein the orifice is formed at an end of a tube-like tip portion, the tip portion having a wall thickness around the orifice of less than about 8 thousandths of an inch.

9. The system of claim 1, wherein the orifice has an inner diameter of less than about 200 microns.

10. The system of claim 8, wherein the pump is connected to the dispenser assembly by a tube having a distal end, the tip portion having a flange on a proximal end, the distal end of the tube being held in contact with the flange of the tip portion.

11. The system of claim 1, wherein the pump is a syringe pump.

12. The system of claim 11, wherein the syringe pump has a linear motor.

13. The system of claim 11, wherein the pump has a stepper motor.

14. The system of claim 10, wherein the dispenser assembly includes a manifold for holding the distal end of the tube in contact with the flange of the tip portion.

15. The system of claim 14, wherein the same manifold secures connection of a plurality of tubes to respective tip portions to define an array of fluid dispensing channels.

16. The system of claim 15, wherein the array of fluid dispensing channels corresponds to an array of wells in a microplate.

17. The system of claim 15, wherein the array of fluid dispensing channels corresponds to an array of sites on a biochip.

18. The system of claim 15, wherein the array corresponds to wells in a standard 96-well microplate.

19. The system of claim 15 further comprising a sample holder registration mechanism that alters the position of a sample holder relative to the manifold so that the same array of fluid dispensing channels can be used to deposit fluid into sample holders having varying densities of deposition sites.

20. A fluid dispensing system comprising
an array of at least eight dispense tips, each dispense tip being connected to a separate syringe pump,
a fluid source bank, the fluid source bank having plural fluid reservoirs, and
a changeable fluid conduit network capable of permitting: (a) each of at least eight of the pumps to be connected to a separate fluid reservoir, (b) each of at least eight of the pumps to be connected to the same fluid reservoir, and (c) any subset of pumps to be connected to the same fluid reservoir while one or more other pumps are connected to another fluid reservoir, wherein the dispense tips are configured to dispense droplets in a range of volumes less than about 5 microliters per droplet without contacting the droplets to a surface.

21. The system of claim 20, wherein each dispense tip has a hydrophobic wall defining an orifice having a diameter of less than about 200 microns, the wall having a thickness of less than about 8 thousandths of an inch.

22. The system of claim 20, wherein the dispense tips are made of a material selected from the group consisting of sapphire, PTFE, polypropylene, polyethylene, and FEP.

23. The system of claim 20, wherein each pump includes a linear motor.

24. A device for dispensing fluid to a sample or sample holder, the device comprising
a fluid reservoir,
a syringe pump device connected to the fluid reservoir, and
a dispense element operatively connected to the pump device, wherein the pump device drives fluid incrementally to the dispense element with sufficient velocity and acceleration so that a fluid aliquot of less than about five microliters separates from the dispense element without contacting the sample or the sample holder.

25. The device of claim 24, wherein the dispense element has a hydrophobic tip with a tube-like wall defining an orifice and is configured to reduce the affinity of dispensed fluid for the dispense element, so that dispensed fluid separates from the dispense element.

26. The device of claim 25, wherein the wall of the tip has a thickness of less than about 8 thousandths of an inch.

27. The device of claim 25, wherein the orifice has a diameter of less than about 200 microliters.

28. The device of claim 24, wherein the dispense element has a tip portion made of a material selected from the group consisting of PTFE, polypropylene, polyethylene, and FEP.

* * * * *